(12) United States Patent
Conklin

(10) Patent No.: US 6,518,480 B1
(45) Date of Patent: Feb. 11, 2003

(54) SELECTIVE TARGET CELL ACTIVATION BY EXPRESSION OF A G PROTEIN-COUPLED RECEPTOR ACTIVATED SUPERIORLY BY SYNTHETIC LIGAND

(75) Inventor: Bruce R. Conklin, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/341,446

(22) PCT Filed: Mar. 25, 1997

(86) PCT No.: PCT/US97/05334

§ 371 (c)(1),
(2), (4) Date: Dec. 20, 1999

(87) PCT Pub. No.: WO97/35478

PCT Pub. Date: Oct. 2, 1997

Related U.S. Application Data

(63) Continuation-in-part of application No. 08/622,348, filed on Mar. 26, 1996, now abandoned.

(51) Int. Cl.$^7$ .............................................. G01N 33/00
(52) U.S. Cl. .......................... 800/3; 800/18; 435/320.1; 435/7.1; 435/6; 435/455; 435/325
(58) Field of Search .......................... 536/23.1; 514/44; 800/3, 18; 424/93.2; 435/320.1, 325, 455

(56) References Cited

U.S. PATENT DOCUMENTS

| | | | | |
|---|---|---|---|---|
| 5,364,791 A | 11/1994 | Vegeto et al. | ............ | 435/320.1 |
| 5,464,758 A | 11/1995 | Gossen et al. | ............. | 435/69.1 |

FOREIGN PATENT DOCUMENTS

| | | |
|---|---|---|
| EP | 0 351 921 | 1/1990 |
| EP | 0 453 119 A1 | 10/1991 |

OTHER PUBLICATIONS

Mastrangelo et. al., Gene Therapy for Human Cancer: An Essay for Clinicians, Feb. 1996, Seminars in Oncology, vol. 23, No. 1, pp. 4–21.*
Verma et al., Gene therapy–promises, problems and prospects, Sep. 18, 1997, Nature, vol. 389, pp. 239–242.*
Anderson, Human gene therapy, Apr. 30, 1998, Nature, vol. 392, pp. 25–30.*
Heistad et al., Gene Therapy for Cerbral Vascular Disease, Sep. 1996, Stroke, vol. 27, pp. 1688–1693.*
Bork et al., Predicting functions from protein sequences–whrer are the bottlenecks?, Apr. 1998, Nature Genetics, vol. 18, pp. 313–318.*
Eck et al., Gene–Based Therapy, 1996, Goodman & Gilman's, Ninth Edition, Chapter 5, pp. 77–101.*

Ngo et al., Computational Complexity, Protein Structure Prediction and the Levinthal Paradox, 1994, Birkhauser Boston, pp. 491–495.*

Pauwels et al, "Review: Amino Acids Domains Involved in Constitutive Activation of G–Protein–Coupled Receptors", 1998, Molecular Neurobiology, vol. 17 pp. 109–135.*

Ostrom et al, "Stoichiometry and Compartmentation in G Protein–Coupled Receptor Signaling: . . . Involving Gs", The Journal of pharmacology and Experimental Therapeutics, vol. 294 No. 2, pp. 407–412.*

Kong et al., "Agonists and antagonists bind to different domains of the cloned kappa opioid receptor" Proceedings of the National Academy of Sciences of USA, vol. 91, Aug. 1994.

Strader C D et al., "Structure and function of a G protein–coupled receptors", Annual Review of Biochemistry, vol. 63, 1994.

Wang WW et al., "Studies of mu and delta opioid receptor selectively utilizing chimeric and site–mutagenized receptors", Proceedings of the National Academy of Sciences of USA, vol. 92, Dec. 1995.

Xue, Ji–Chun, et al., "Differential Binding Domains of Peptide and Non–peptide Ligands in the Cloned Rat κ Opioid Receptor," *The Journal of Biological Chemistry*, vol. 269, No. 48, Issue of Dec. 2, 1994, pp. 30195–30199.

Wolff, Gerhard, et al., "Ectopic expression of thyrotropin releasing hormone (TRH) receptors in liver modulates organ function to regulate blood glucose by TRH", *Nature Genetics*, Mar. 1996, vol. 12, pp. 274–279.

Baldwin, Joyce M., "Structure and function of receptors coupled to G proteins," *Cell Biology*, (1994) vol. 6, pp. 180–190.

(List continued on next page.)

*Primary Examiner*—Dave T. Nguyen
(74) *Attorney, Agent, or Firm*—Carol L. Francis; Paula A. Borden; Bozicevic, Field & Francis, LLP

(57) ABSTRACT

The invention provides a method for selectively activating a target cell, where the target cell expresses a receptor activated superiorly by a synthetic ligand (RASSL) having decreased binding affinity for a selected natural ligand and normal or near normal binding affinity for a synthetic small molecule agonist. Thus, RASSL-mediated activation of target cells does not occur to a significant extent in the presence of natural G protein-coupled receptor ligand, but is significantly stimulated upon exposure to a synthetic small molecule. RASSL-expressing target cells are selectively activated by exposing of the cells to an appropriate synthetic small molecule, which in turn binds the RASSL, resulting in G protein activation and triggering of a specific cellular response associated with G protein activation (e.g., cellular proliferation or cellular secretion).

13 Claims, 18 Drawing Sheets

OTHER PUBLICATIONS

Cascieri, Margaret A., et al., "Molecular Characterization of a Common Binding Site for Small Molecules Within the Transmembrane Domain of G–Protein Coupled Receptors," *Journal of Pharmacological and Toxicological Methods*, (Aug. 1995) vol. 33, No. 4, pp. 179–185.

Cheung, Anne H., et al., "Involvement of Specific Hydrophobic, but not Hydrophilic, Amino Acids in the Third Intracellular Loop of the β–Adrenergic Receptor in the Activation of $G_S$," (1992) *Molecular Pharmacology*, vol. 41, pp. 1061–1065.

Conklin, Bruce R., et al., "Structural Elements of Gα Subunits That Interact with Gβγ, Receptors, and Effectors," *Cell*, (May 21, 1993) vol. 73, pp. 631–641.

Coughlin, Shaun R., "Expanding horizons for receptors coupled to G proteins: diversity and disease," *Cell Biology*, (1994) vol. 6, pp. 191–197.

Cunningham, Lee Anna, et al., "Nerve growth factor released by transgenic astrocytes enhances the function of adrenal chromaffin cell grafts in a rat model of Parkinson's disease," *Brain Research*, 658 (1994) pp. 219–231.

Dhanasekaran, N."G Protein–Coupled Receptor Systems Involved in Cell Growth and Oncogenesis," *Endocrine Reviews*, (Jun., 1995) vol. 16, No. 3, pp. 259–270.

Freidinger, Roger M., "Toward peptide receptor ligand drugs: Progress on nonpeptides," *Prog. Drug Res.*, (1993) 40:33–98.

Gossen, Manfred, et al., "Transcriptional Activation by Tetracyclines in Mammalian Cels," *Science*, (Jun. 23, 1995) vol. 268, pp. 1766–1769.

Jiao, Shoushu, et al., "Long–term correction of rat model of Parkinson's disease by gene therapy," *Nature*, (Apr. 1, 1993) vol. 362, pp. 450–453.

Kobayashi, Satoshi, et al., "Grafts of genetically modified fibroblasts expressing neural cell adhesion molecule L1 into transected spinal cord of adult rats," *Neuroscience Letters* 188 (1995) pp. 191–194.

Kobilka, Brian, "Adrenergic Receptors as Models for G Protein–Coupled Receptors," *Annu. Rev. Neurosci.* (1992) vol. 15, pp. 87–114.

Linder, Maurine, E., "G. Proteins," *Scientific American*, (Jul. 1992) pp. 56–61 and 64–65.

Liu, Jie, et al., "Identification of a receptor/G–protein contact site critical for signaling specificity and G–protein activation," *Proc. Natl. Acad. Sci USA*, (Dec. 1995) vol. 92, pp. 11642–11646.

Neer, Eva J., "Heterotrimeric G Proteins: Organizers of Transmembrane Signals," *Cell*, (Jan. 27, 1995) vol. 80, pp. 249–257.

Rosenfeld, Melissa A., et al., "Adenovirus–Mediated Transfer of a Recombinant αl–Antitrypsin Gene to the Lung Epithelium in Vivo," *Reports* Apr. 19, 1991, vol. 252, pp. 431–434.

Schwartz, Thue W., "Locating ligand–binding sites in 7TM receptors by protein engineering," *Current Opinion in Biotechnology* (1994) vol. 5, pp. 434–444.

Shenker, Andrew, "G Protein–coupled receptor structure and function: the impact of disease–causing mutations," *Baillière's Clinical Endocrinology and Metabolism* (Jul. 1995) vol. 9, No. 3, pp. 427–451.

Spencer, David M., "Controlling Signal Transduction with Synthetic Ligands," *Science*, (Nov. 12, 1993) vol. 262, pp. 1019–1024.

Spiegel, Allen M., "G proteins in cellular control," *Current Opinion in Cell Biology*, (1992) vol. 4, pp. 203–211.

Strader, Catherine D., et al., "Allele–specific Activation of Genetically Engineered Receptors," *The Journal of Biological Chemistry* vol. 266, No. 1, Issue of Jan. 5, 1991, pp. 5–8.

Tuszynski, Mark H., et al., "Fibroblasts Genetically Modified to Produce Nerve Growth Factor Induce Robust Neuritic Ingrowth after Grafting to the Spinal Cord," *Experimental Neurology* (1994) 126, pp. 1–14.

Wang, Yaolin, et al., "A regulatory system for use in gene transfer," *Proc. Natl, Acad. Sci. USA* (Aug. 1994) vol. 91, pp. 8180–8184.

\* cited by examiner

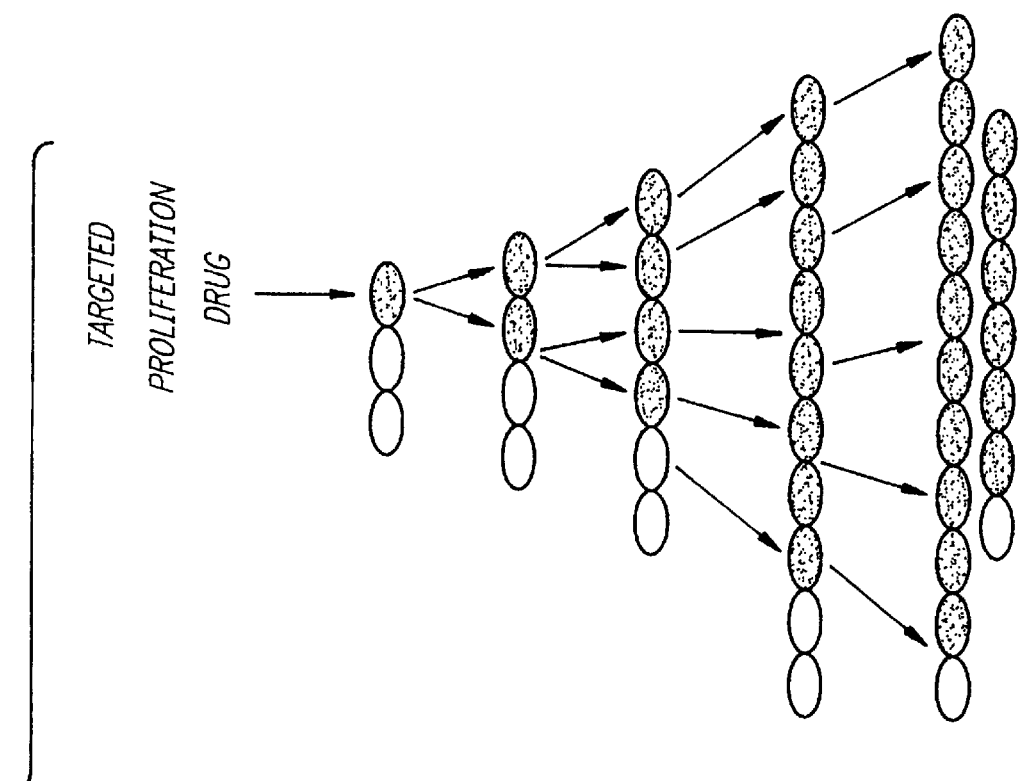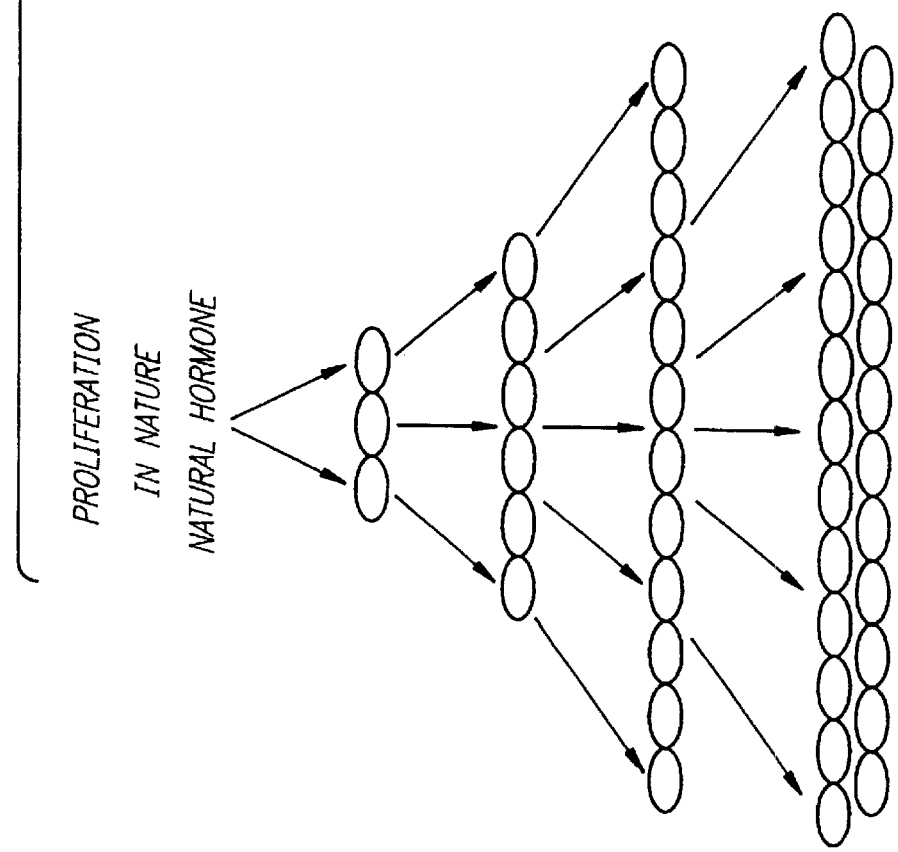
FIG. 2

FIG. 3
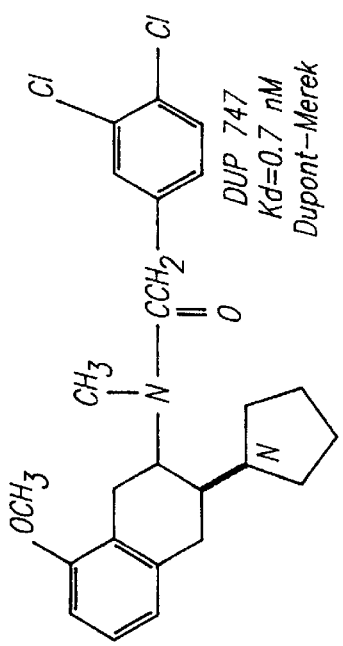
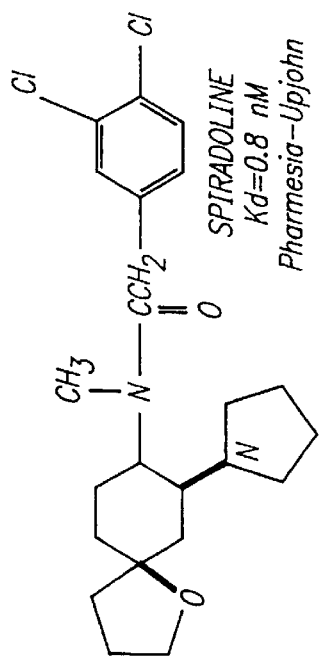
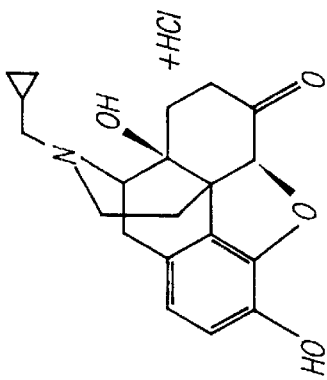
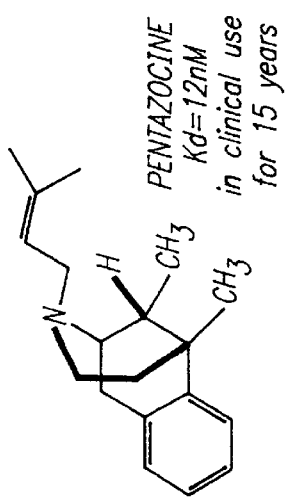
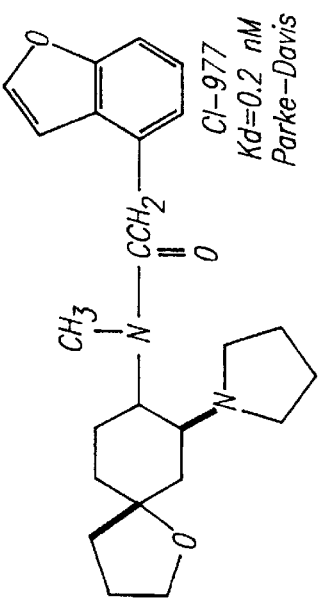

TWO PROTOTYPE RASSLs BASED ON THE KAPPA OPIOID RECEPTOR: OR1 AND OR2

FIG. 7A

Human Wild-type Kappa Opioid receptor with prolactin signal sequence, FLAG epitope and HA epitope.
Upper case = hKappa.  Lower case = non-hKappa

```
1/1                                       31/11
atg gac agc aaa ggt tcg tcg cag aaa ggg   tcc cgc ctg ctc ctg ctg ctg gtg gtg tca
Met asp ser lys gly ser ser gln lys gly   ser arg leu leu leu leu leu val val ser
61/21                                     91/31
aat cta ctc ttg tgc cag ggt gtg gtc tcc   gat tac aaa gat gat gat gat gtc GAC TCC
asn leu leu leu cys gln gly val val ser   asp tyr lys asp asp asp asp val asp ser
121/41                                    151/51
CCG ATC CAG ATC TTC CGC GGG GAG CCG GGC   CCT ACC TGC GCC CCG AGC GCC TGC CTG CCC
pro ile gln ile phe arg gly glu pro gly   pro thr cys ala pro ser ala cys leu pro
181/61                                    211/71
CCC AAC AGC AGC GCC TGG TTT CCC GGC TGG   GCC GAG CCC GAC AGC AAC GGC AGC GCC GGC
pro asn ser ser ala trp phe pro gly trp   ala glu pro asp ser asn gly ser ala gly
241/81                                    271/91
TCG GAG GAC GCG CAG CTG GAG CCC GCG CAC   ATC TCC CCG GCC ATC CCG GTC ATC ATC ACG
ser glu asp ala gln leu glu pro ala his   ile ser pro ala ile pro val ile ile thr
301/101                                   331/111
GCG GTC TAC TCC GTA GTG TTC GTC GTG GGC   TTG GTG GGC AAC TCG CTG GTC ATG TTC GTG
ala val tyr ser val val phe val val gly   leu val gly asn ser leu val met phe val
361/121                                   391/131
ATC ATC CGA TAC ACA AAG ATG AAG ACA GCA   ACC AAC ATT TAC ATA TTT AAC CTG GCT TTG
ile ile arg tyr thr lys met lys thr ala   thr asn ile tyr ile phe asn leu ala leu
421/141                                   451/151
GCA GAT GCT TTA GTT ACT ACA ACC ATG CCC   TTT CAG AGT ACG GTC TAC TTG ATG AAT TCC
ala asp ala leu val thr thr thr met pro   phe gln ser thr val tyr leu met asn ser
481/161                                   511/171
TGG CCT TTT GGG GAT GTG CTG TGC AAG ATA   GTA ATT TCC ATT GAT TAC TAC AAC ATG TTC
trp pro phe gly asp val leu cys lys ile   val ile ser ile asp tyr tyr asn met phe
541/181                                   571/191
ACC AGC ATC TTC ACC TTG ACC ATG ATG AGC   GTG GAC CGC TAC ATT GCC GTG TGC CAC CCC
thr ser ile phe thr leu thr met met ser   val asp arg tyr ile ala val cys his pro
601/201                                   631/211
GTG AAG GCT TTG GAC TTC CGC ACA CCC TTG   AAG GCA AAG ATC ATC AAT ATC TGC ATC TGG
val lys ala leu asp phe arg thr pro leu   lys ala lys ile ile asn ile cys ile trp
661/221                                   691/231
CTG CTG TCG TCA TCT GTT GGC ATC TCT GCA   ATA GTC CTT GGA GGC ACC AAA GTC AGG GAA
leu leu ser ser ser val gly ile ser ala   ile val leu gly gly thr lys val arg glu
721/241                                   751/251
GAC GTC GAT GTC ATT GAG TGC TCC TTG CAG   TTC CCA GAT GAT GAC TAC TCC TGG TGG GAC
asp val asp val ile glu cys ser leu gln   phe pro asp asp asp tyr ser trp trp asp
781/261                                   811/271
CTC TTC ATG AAG ATC TGC GTC TTC ATC TTT   GCC TTC GTG ATC CCT GTC CTC ATC ATC ATC
leu phe met lys ile cys val phe ile phe   ala phe val ile pro val leu ile ile ile
841/281                                   871/291
GTC TGC TAC ACC CTG ATG ATC CTG CGT CTC   AAG AGC GTC CGG CTC CTT TCT GGC TCC CGA
val cys tyr thr leu met ile leu arg leu   lys ser val arg leu leu ser gly ser arg
```

FIG. 7B

```
901/301                              931/311
GAG AAA GAT CGC AAC CTG CGT AGG ATC ACC AGA CTG GTC CTG GTG GTG GTG GCA GTC TTC
glu lys asp arg asn leu arg arg ile thr arg leu val leu val val val ala val phe
961/321                              991/331
GTC GTC TGC TGG ACT CCC ATT CAC ATA TTC ATC CTG GTG GAG GCT CTG GGG AGC ACC TCC
val val cys trp thr pro ile his ile phe ile leu val glu ala leu gly ser thr ser
1021/341                             1051/351
CAC AGC ACA GCT GCT CTC TCC AGC TAT TAC TTC TGC ATC GCC TTA GGC TAT ACC AAC AGT
his ser thr ala ala leu ser ser tyr tyr phe cys ile ala leu gly tyr thr asn ser
1081/361                             1111/371
AGC CTG AAT CCC ATT CTC TAC GCC TTT CTT GAT GAA AAC TTC AAG CGG TGT TTC CGG GAC
ser leu asn pro ile leu tyr ala phe leu asp glu asn phe lys arg cys phe arg asp
1141/381                             1171/391
TTC TGC TTT CCA CTG AAG ATG AGG ATG GAG CGG CAG AGC ACT AGC AGA GTC CGA AAT ACA
phe cys phe pro leu lys met arg met glu arg gln ser thr ser arg val arg asn thr
1201/401                             1231/411
GTT CAG GAT CCT GCT TAC CTG AGG GAC ATC GAT GGG ATG AAT AAA CCA GTA ggt tac ccc
val gln asp pro ala tyr leu arg asp ile asp gly met asn lys pro val gly tyr pro
1261/421
tac gac gtc ccc gac tac gcc tga   SEQ ID No: 3
tyr asp val pro asp tyr ala OPA   SEQ ID No: 4
```

FIG. 8A

OR1, prototype RASSL DNA and amino acid sequence.
Upper case = hKappa. Lower case = non-hKappa
N-term Prolactin signal sequence (1-90), Flag epitope (91-114), rKappa
OR (474-701), rDelta OR (702-787), HA epitope (1243-1275).

```
1/1                                      31/11
atg gac agc aaa ggt tcg tcg cag aaa ggg  tcc cgc ctg ctc ctg ctg ctg gtg gtg tca
Met asp ser lys gly ser ser gln lys gly  ser arg leu leu leu leu leu val val ser
61/21                                    91/31
aat cta ctc ttg tgc cag ggt gtg gtc tcc  gat tac aaa gat gat gat gat gtc GAC TCC
asn leu leu leu cys gln gly val val ser  asp tyr lys asp asp asp asp val asp ser
121/41                                   151/51
CCG ATC CAG ATC TTC CGC GGG GAG CCG GGC  CCT ACC TGC GCC CCG AGC GCC TGC CTG CCC
pro ile gln ile phe arg gly glu pro gly  pro thr cys ala pro ser ala cys leu pro
181/61                                   211/71
CCC AAC AGC AGC GCC TGG TTT CCC GGC TGG  GCC GAG CCC GAC AGC AAC GGC AGC GCC GGC
pro asn ser ser ala trp phe pro gly trp  ala glu pro asp ser asn gly ser ala gly
241/81                                   271/91
TCG GAG GAC GCG CAG CTG GAG CCC GCG CAC  ATC TCC CCG GCC ATC CCG GTC ATC ATC ACG
ser glu asp ala gln leu glu pro ala his  ile ser pro ala ile pro val ile ile thr
301/101                                  331/111
GCG GTC TAC TCC GTA GTG TTC GTC GTG GGC  TTG GTG GGC AAC TCG CTG GTC ATG TTC GTG
ala val tyr ser val val phe val val gly  leu val gly asn ser leu val met phe val
361/121                                  391/131
ATC ATC CGA TAC ACA AAG ATG AAG ACA GCA  ACC AAC ATT TAC ATA TTT AAC CTG GCT TTG
ile ile arg tyr thr lys met lys thr ala  thr asn ile tyr ile phe asn leu ala leu
421/141                                  451/151
GCA GAT GCT TTA GTT ACT ACA ACC ATG CCC  TTT CAG AGT ACG GTC TAC TTG ATg aat tct
ala asp ala leu val thr thr thr met pro  phe gln ser thr val tyr leu met asn ser
481/161                                  511/171
tgg cct ttt gga gat gtt ctg tgc aag att  gtc att tcc att gac tac tac aac atg ttt
trp pro phe gly asp val leu cys lys ile  val ile ser ile asp tyr tyr asn met phe
541/181                                  571/191
acc agc ata ttc acc ttg acc atg atg agt  gtg gac cgt tac att gcc gtg tgc cac cct
thr ser ile phe thr leu thr met met ser  val asp arg tyr ile ala val cys his pro
601/201                                  631/211
gtg aaa gct ttg gat ttc cga aca cct ttg  aaa gca aag atc atc aac atc tgc att tgg
val lys ala leu asp phe arg thr pro leu  lys ala lys ile ile asn ile cys ile trp
661/221                                  691/231
cta ctg gca tca tct gtt ggt ata tca gcg  ata gtc ctt ggg gtg acc caa ccc cgg gat
leu leu ala ser ser val gly ile ser ala  ile val leu gly val thr gln pro arg asp
721/241                                  751/251
gga gca gtg gta tgc acg ctc cag ttc ccc  agc ccc agc tgg tac tgg gac act gtg acc
gly ala val val cys thr leu gln phe pro  ser pro ser trp tyr trp asp thr val thr
781/261                                  811/271
aag atc tGC GTC TTC ATC TTT GCC TTC GTG  ATC CCT GTC CTC ATC ATC ATC GTC TGC TAC
lys ile cys val phe ile phe ala phe val  ile pro val leu ile ile ile val cys tyr
841/281                                  871/291
ACC CTG ATG ATC CTG CGT CTC AAG AGC GTC  CGG CTC CTT TCT GGC TCC CGA GAG AAA GAT
thr leu met ile leu arg leu lys ser val  arg leu leu ser gly ser arg glu lys asp
```

FIG. 8B

```
901/301                                   931/311
CGC AAC CTG CGT AGG ATC ACC AGA CTG GTC   CTG GTG GTG GTG GCA GTC TTC GTC GTC TGC
arg asn leu arg arg ile thr arg leu val   leu val val val ala val phe val val cys
961/321                                   991/331
TGG ACT CCC ATT CAC ATA TTC ATC CTG GTG   GAG GCT CTG GGG AGC ACC TCC CAC AGC ACA
trp thr pro ile his ile phe ile leu val   glu ala leu gly ser thr ser his ser thr
1021/341                                  1051/351
GCT GCT CTC TCC AGC TAT TAC TTC TGC ATC   GCC TTA GGC TAT ACC AAC AGT AGC CTG AAT
ala ala leu ser ser tyr tyr phe cys ile   ala leu gly tyr thr asn ser ser leu asn
1081/361                                  1111/371
CCC ATT CTC TAC GCC TTT CTT GAT GAA AAC   TTC AAG CGG TGT TTC CGG GAC TTC TGC TTT
pro ile leu tyr ala phe leu asp glu asn   phe lys arg cys phe arg asp phe cys phe
1141/381                                  1171/391
CCA CTG AAG ATG AGG ATG GAG CGG CAG AGC   ACT AGC AGA GTC CGA AAT ACA GTT CAG GAT
pro leu lys met arg met glu arg gln ser   thr ser arg val arg asn thr val gln asp
1201/401                                  1231/411
CCT GCT TAC CTG AGG GAC ATC GAT GGG ATG   AAT AAA CCA GTA ggt tac ccc tac gac gtc
pro ala tyr leu arg asp ile asp gly met   asn lys pro val gly tyr pro tyr asp val
1261/421
ccc gac tac gcc tga    SEQ ID NO: 5
pro asp tyr ala OPA    SEQ ID NO: 6
```

FIG. 9A

OR2 Prototype RASSL and amino acid sequence.
Upper case = hKappa. Lower case = non-hKappa
N-term Prolactin signal sequence (1-90), Flag epitope (91-114), rKappa
OR (474-701), rDelta OR (702-787), Glutamic acid to Glutamine mutation
(991-993), HA epitope (1243-1275).

```
1/1                                           31/11
atg gac agc aaa ggt tcg tcg cag aaa ggg tcc cgc ctg ctc ctg ctg ctg gtg gtg tca
Met asp ser lys gly ser ser gln lys gly ser arg leu leu leu leu leu val val ser
61/21                                         91/31
aat cta ctc ttg tgc cag ggt gtg gtc tcc gat tac aaa gat gat gat gat gtc GAC TCC
asn leu leu leu cys gln gly val val ser asp tyr lys asp asp asp asp val asp ser
121/41                                        151/51
CCG ATC CAG ATC TTC CGC GGG GAG CCG GGC CCT ACC TGC GCC CCG AGC GCC TGC CTG CCC
pro ile gln ile phe arg gly glu pro gly pro thr cys ala pro ser ala cys leu pro
181/61                                        211/71
CCC AAC AGC AGC GCC TGG TTT CCC GGC TGG GCC GAG CCC GAC AGC AAC GGC AGC GCC GGC
pro asn ser ser ala trp phe pro gly trp ala glu pro asp ser asn gly ser ala gly
241/81                                        271/91
TCG GAG GAC GCG CAG CTG GAG CCC GCG CAC ATC TCC CCG GCC ATC CCG GTC ATC ATC ACG
ser glu asp ala gln leu glu pro ala his ile ser pro ala ile pro val ile ile thr
301/101                                       331/111
GCG GTC TAC TCC GTA GTG TTC GTC GTG GGC TTG GTG GGC AAC TCG CTG GTC ATG TTC GTG
ala val tyr ser val val phe val val gly leu val gly asn ser leu val met phe val
361/121                                       391/131
ATC ATC CGA TAC ACA AAG ATG AAG ACA GCA ACC AAC ATT TAC ATA TTT AAC CTG GCT TTG
ile ile arg tyr thr lys met lys thr ala thr asn ile tyr ile phe asn leu ala leu
421/141                                       451/151
GCA GAT GCT TTA GTT ACT ACA ACC ATG CCC TTT CAG AGT ACG GTC TAC TTG ATg aat tct
ala asp ala leu val thr thr thr met pro phe gln ser thr val tyr leu met asn ser
481/161                                       511/171
tgg cct ttt gga gat gtt ctg tgc aag att gtc att tcc att gac tac tac aac atg ttt
trp pro phe gly asp val leu cys lys ile val ile ser ile asp tyr tyr asn met phe
541/181                                       571/191
acc agc ata ttc acc ttg acc atg atg agt gtg gac cgt tac att gcc gtg tgc cac cct
thr ser ile phe thr leu thr met met ser val asp arg tyr ile ala val cys his pro
601/201                                       631/211
gtg aaa gct ttg gat ttc cga aca cct ttg aaa gca aag atc atc aac atc tgc att tgg
val lys ala leu asp phe arg thr pro leu lys ala lys ile ile asn ile cys ile trp
661/221                                       691/231
cta ctg gca tca tct gtt ggt ata tca gcg ata gtc ctt ggg gtg acc caa ccc cgg gat
leu leu ala ser ser val gly ile ser ala ile val leu gly val thr gln pro arg asp
721/241                                       751/251
gga gca gtg gta tgc acg ctc cag ttc ccc agc ccc agc tgg tac tgg gac act gtg acc
gly ala val val cys thr leu gln phe pro ser pro ser trp tyr trp asp thr val thr
781/261                                       811/271
aag atc tGC GTC TTC ATC TTT GCC TTC GTG ATC CCT GTC CTC ATC ATC ATC GTC TGC TAC
lys ile cys val phe ile phe ala phe val ile pro val leu ile ile ile val cys tyr
841/281                                       871/291
ACC CTG ATG ATC CTG CGT CTC AAG AGC GTC CGG CTC CTT TCT GGC TCC CGA GAG AAA GAT
thr leu met ile leu arg leu lys ser val arg leu leu ser gly ser arg glu lys asp
```

FIG. 9B

```
901/301                                 931/311
CGC AAC CTG CGT AGG ATC ACC AGA CTG GTC CTG GTG GTG GTG GCA GTC TTC GTC GTC TGC
arg asn leu arg arg ile thr arg leu val leu val val val ala val phe val val cys
961/321                                 991/331
TGG ACT CCC ATT CAC ATA TTC ATC CTa GTt cAG GCT CTG GGG AGC ACC TCC CAC AGC ACA
trp thr pro ile his ile phe ile leu val gln ala leu gly ser thr ser his ser thr
1021/341                                1051/351
GCT GCT CTC TCC AGC TAT TAC TTC TGC ATC GCC TTA GGC TAT ACC AAC AGT AGC CTG AAT
ala ala leu ser ser tyr tyr phe cys ile ala leu gly tyr thr asn ser ser leu asn
1081/361                                1111/371
CCC ATT CTC TAC GCC TTT CTT GAT GAA AAC TTC AAG CGG TGT TTC CGG GAC TTC TGC TTT
pro ile leu tyr ala phe leu asp glu asn phe lys arg cys phe arg asp phe cys phe
1141/381                                1171/391
CCA CTG AAG ATG AGG ATG GAG CGG CAG AGC ACT AGC AGA GTC CGA AAT ACA GTT CAG GAT
pro leu lys met arg met glu arg gln ser thr ser arg val arg asn thr val gln asp
1201/401                                1231/411
CCT GCT TAC CTG AGG GAC ATC GAT GGG ATG AAT AAA CCA GTA ggt tac ccc tac gac gtc
pro ala tyr leu arg asp ile asp gly met asn lys pro val gly tyr pro tyr asp val
1261/421
ccc gac tac gcc tga      SEQ ID NO: 7
pro asp tyr ala OPA      SEQ ID NO: 8
```

FIG. 11-1

Alignment of Three Biogenic Amine Receptors (hβ2-AR, h5HT-1A, h5HT-2C)
"*" indicates the conserved binding site for the biogenic amine (natural ligand)

```
hB2AR                                              MGQPGNGSAFLLAPNRS
5HT-1A-R                                    MDVLSP GQGNNTTSPP APFE
5HT-2C-R                       MVNLRNAVHSFLVHLIGLLVWQCDISVSPVAAIVTDI

------TM1------
hB2AR                                  GMGIVMSLIVLAIVFGNVLVITAIA      KFERLQTVTNYF
5HT-1A-R           HAPDHDVTQQRDEVWVV   ITSLLLGTLIFCAVLGNACVVAAIA      LERSLQNVANYL
                   TGGNTTGISDVTVSYQV
5HT-2C-R           FNTSDGGRFKFPDGVQN   WPALSIVIIIMTIGGNILVIMAVS       MEKKLHNATNYF

------TM2------                                  ---*---TM3------
hB2AR         ITSLACADLVMGLAVVPFGAAHILMK   ARVIILMVWIVSGLTSFLPIQMHWYRA        THQEAINCYANETCCDFF
5HT-1A-R      IGSLAVTDLMVSVLVLPMAALYQVLN   AAALISLTWLIGFLISIPPML GW RT             PEDRSDPDACTIS
5HT-2C-R      LMSLAIADMLVGLLVMPLSLLAILYDY  AIMKIAIVWAISIGVSVPIPVIGL RD            EEKVFVNNTTCVL

------TM4------
hB2AR        AITSPFKYQSLLTKNK
5HT-1A-R     AITDPIDYVNKRTPRR
5HT-2C-R     AIRNPIEHSRFNSRTK

------TM5------
hB2AR         TNQAYAIASSIVSFYVPLVIMVFVY      SRVFQEAKRQLQKIDKSEGRFHVQNL
5HT-1A-R      KDHGYTIYSTFGAFYIPLLLMLVLY      GRIFRAARFRIRKTVKKVEKTGADTRHGASPAPQPKK
5HT-2C-R      NDPNFVLIGSFVAFFIPLTIMVITY      CLTIYVLRRQALMLLHGHTEEPPGLSLDFLKCCKRNTAEEEN
```

FIG. 11-2

```
hB2AR   SQVEQDGRTGHGLRRSSKFCLKEHK
5HT-1A-R SVNGESGSRNWRLGVESKAGGALCANGAVRQGDDGAALEVIEVHRVGNSKEHLPLPSEAGPTPCAPASFERKNERNAEAKRK
5HT-2C-R SANPNQDQNARRRKKERRPRGTMQ

------TM6--*------                      ------TM7------
hB2AR       ALKT      LGIIMGTFTLCWLPFFIVNIVHVI  QDNL  IRKE  VYILLNWIGYVNSGFNPLIYCRSPDFR
5HT-1A-R MALARERKTVKT  LGIIMGTFILCWLPFFIVALVLPF  CESSCHMPTL   LGAIINWLGYSNSLLNPVIYAYFNKDF
5HT-2C-R AINNERKASKV   LGIVFFVFLIMWCPFFITNILSVL  CEKSCNQKLMEK LLNVFVWIGYVCSGINPLVYTLFNKIY hB2AR    IAFQELLCLRRSSLKAYGNGYSSNGNTGEQSGYHVEQEKENKLLCEDLPGTEDFVGHQGTVPSDNIDSQGRNCSTNDSLLEEEYMPMEZ SEQ ID NO: 9
5HT-1A-R QNAFKKIIKCKFCRQ SEQ ID NO: 10                                                           SEQ ID NO: 11
5HT-2C-R RRAFSNYLRCNYKVEKKPPVRQIPRVAATALSGRELNVNIYRHTNEPVIEKASDNEPGIEMQVENLELPVNPSSVVSERISSV
```

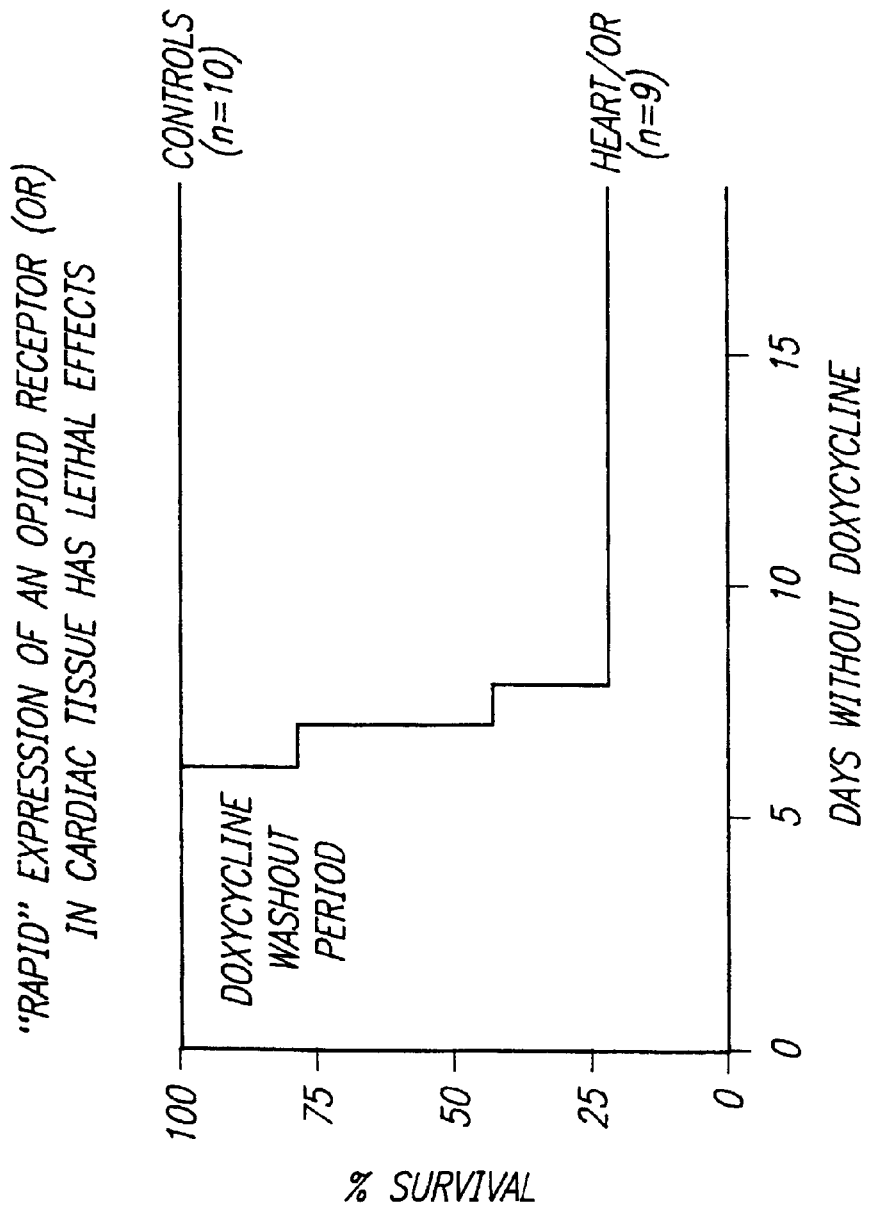

SELECTIVE TARGET CELL ACTIVATION BY EXPRESSION OF A G PROTEIN-COUPLED RECEPTOR ACTIVATED SUPERIORLY BY SYNTHETIC LIGAND

CROSS-REFERENCE TO RELATED APPLICATIONS

This application is a national phase filing under 35 U.S.C. §371 of International Patent Application No. PCT/US97/05334, which is a continuation-in-part of earlier-filed U.S. application Ser. No. 08/622,348, filed Mar. 26, 1996, abandoned, which applications are incorporated herein by reference.

STATEMENT AS TO RIGHTS TO INVENTIONS MADE UNDER FEDERALLY SPONSORED RESEARCH AND DEVELOPMENT

This invention was made with Government support under Grant No. HL-02555 awarded by the National Institutes of Health. The Government may have certain rights in this invention.

FIELD OF THE INVENTION

This invention relates generally to the field of pharmacological control of cells expressing a protein or other molecule of interest.

BACKGROUND OF THE INVENTION

Despite the tremendous advances in the field of genetic engineering and expression of a DNA of interest in a desired cell, few tools exist in the art for the direct, selective manipulation of a specific physiological response in a cell. For example, although cell growth can be facilitated in in vitro culture by inclusion of nutrients in the culture medium, there are few adequate means available to stimulate cell growth directly and selectively.

The problem is further complicated where the cell culture contains a desired cell type as well as a variety of undesired, contaminating cells. While the nutrients in the culture medium may enhance growth of the desired cell type, most often these nutrients also enhance growth of the undesired, contaminating cells, thus interfering with attempts to enrich the culture for the desired cell type. Some of these complicating factors might be overcome by transforming the desired cell type with an antibiotic resistance gene or other selective marker. However, the desired cells may be sensitive to the selective agent and grow more slowly in its presence, or the undesired, contaminating cells may be resistant to the selective agent and grow in the culture despite the presence of the agent.

In addition, there are many settings both in vitro and in vivo in which one wishes to enrich a cell population for a specific target cell, or elicit a specific physiological response in a target cell, without substantially affecting nontarget cells in the population. Gene therapy is an example of this latter situation. The basic concept in gene therapy involves the introduction of a DNA sequence encoding a protein or other molecule that, when expressed, can overcome a genetic defect associated with the disease, or produce some other therapeutic protein or other molecule that will either cure or ameliorate symptoms of the disease. The DNA introduced by gene therapy stably integrates into genome of host target cells, thus producing genetically altered cells expressing the desired therapeutic protein and thus treating the disease.

A critical limitation of current in vivo and ex vivo gene therapy efforts is the inability to amplify the number of transfected cells. In several instances, DNA encoding the therapeutic protein of interest is successfully delivered to and expressed in the target cells, but too few target cells are transformed to provide a measurable therapeutic response. If these few transformed cells could be specifically activated at the cellular level in vivo, e.g., to proliferate or to secrete their therapeutic product, the desired therapeutic effect could be achieved. This invention addresses this problem.

SUMMARY OF THE INVENTION

The invention features methods and compositions for selective cellular activation of a target cell. Targeted, transformed cells expressing a modified G protein-coupled receptor that is activated superiorly by a synthetic ligand (RASSL) are selectively activated by synthetic small molecule binding to the RASSL. A RASSL is a modified G protein-coupled receptor having decreased binding affinity for a selected natural (i.e., endogenous) ligand (relative to binding of the selected ligand by a wild-type G protein-coupled receptor), but having normal, near normal, or enhanced binding affinity for a synthetic small molecule. Thus, RASSL-mediated activation of RASSL-expressing cells does not occur to a significant extent in the presence of the selected natural ligand, but responds significantly upon exposure to a synthetic small molecule.

In one embodiment, the RASSL-encoding DNA is introduced into the target cells to be activated, and can be cotransformed with DNA encoding a therapeutic protein of interest (e.g., cotransformed with a DNA of interest to be used in a gene therapy regimen). Cells expressing a RASSL are selectively activated by administration of an appropriate synthetic small molecule, which in turn binds the RASSL and facilitates activation of the G protein cascade and a selected physiological, cellular response (e.g., cellular proliferation, cellular secretion) in the RASSL-expressing cell.

The invention also features specific G protein-coupled receptors modified such that the receptor retains small molecule binding affinity, but is decreased in binding affinity of a selected natural ligand relative to a native G protein-coupled receptor from which the modified receptor is derived.

The invention further features a cellular implant comprising RASSL-expressing target cells that, upon binding of an appropriate synthetic small molecule ligand, exhibit a desired G protein-mediated cellular response (e.g., cellular proliferation or cellular secretion).

The invention additionally features a transgenic, reversible disease animal model. The transgenic animal expresses a RASSL that upon stimulation causes a disease- or condition-associated symptom in the animal.

A primary object of the invention is to provide a method to activate target cells selectively, particularly target cells expressing a desired protein or other molecule of interest. The desired protein or other molecule of interest can be encoded by genetic material that is either endogenous (e.g., naturally occurring) or heterologous (e.g., introduced by transformation or transfection) to the target cell genome.

Another object of the invention is to selectively activate target cells by amplifying cellular proliferation and/or cellular secretion.

Another object of the invention is to provide a method for enhancing the efficacy of gene therapy techniques by allowing controlled, targeted activation of cells transformed with a DNA of interest.

An advantage of the present invention is that targeted cellular activation can be controlled by exposing the target cells to varying amounts of the synthetic small molecule RASSL agonist.

Another advantage of the present invention is that, where the target cells are present in a mammalian host, the synthetic small molecule used to elicit a response in RASSL-expressing cells can be administered systemically (orally or intravenously), and need not be administered directly to the target cell site(s).

Yet another advantage of the invention is that the synthetic small molecules can cross the blood-brain barrier of a mammalian subject, thus allowing for activation of RASSL-expressing cells located in the mammalian host's brain tissue by oral or intravenous administration of the drug.

Another advantage of the invention is that RASSLs can be designed from G protein-coupled receptors which bind synthetic small molecule that have been developed previously for use in mammalian subjects (e.g., for uses as such as pain relief, reduction of depression and weight reduction).

These and other objects, advantages and features of the present invention will become apparent to those persons skilled in the art upon reading the details of the vectors, cell lines and methodology as more fully set forth below.

BRIEF DESCRIPTION OF THE DRAWINGS

FIG. 2 is a schematic contrasting cell proliferation in nature and targeted proliferation accomplished by the method of the invention.

FIG. 3 is a schematic showing the structural formulae of the exemplary synthetic small molecule agonists of the kappa opioid receptor (KOR) (Pentazocine, DUP 747, CI-977, and Spiradoline), as well as exemplary synthetic small molecules that act as antagonists to a wild-type KOR, but can act as an agonist of a RASSL generated by a point mutation of the KOR (naltrexone and naloxone).

FIGS. 7A and 7B are schematics showing the amino acid and nucleotide sequences of wild-type human kappa opioid receptor having an N-terminal Prolactin signal, a FLAG epitope, and an HA tag. Sequences derived from the wild-type human kappa opioid receptor are shown as upper case letters.

FIGS. 8A and 8B are schematics showing the amino acid and nucleotide sequences of OR1, a RASSL of the invention, having an N-terminal Prolactin signal, a FLAG epitope, and an HA tag. Sequences derived from the wild-type human kappa opioid receptor are shown as upper case letters.

FIGS. 9A and 9B are schematics showing the nucleotide sequence of OR2, a RASSL of the invention, having an N-terminal Prolactin signal, a FLAG epitope, and an HA tag. Sequences derived from the wild-type human kappa opioid receptor are shown as upper case letters.

FIGS. 11-1 and 11-2 is a schematic showing an alignment of the amino acid sequences of the human receptors beta-2 adrenergic receptor (h$\beta_2$AR) (SEQ ID NO:9), the serotonin-1A receptor (h5HT-1A-R) (SEQ ID NO:10), and the serotonin-2C receptor (SEQ ID NO:11). Asterisks indicates the conserved binding site for the natural biogenic amine ligand.

FIG. 12 is a graph showing the lethal effects of rapid expression of a KOR RASSL in the heart tissue of transgenic mice.

DESCRIPTION OF THE PREFERRED EMBODIMENTS

Figure 1A:
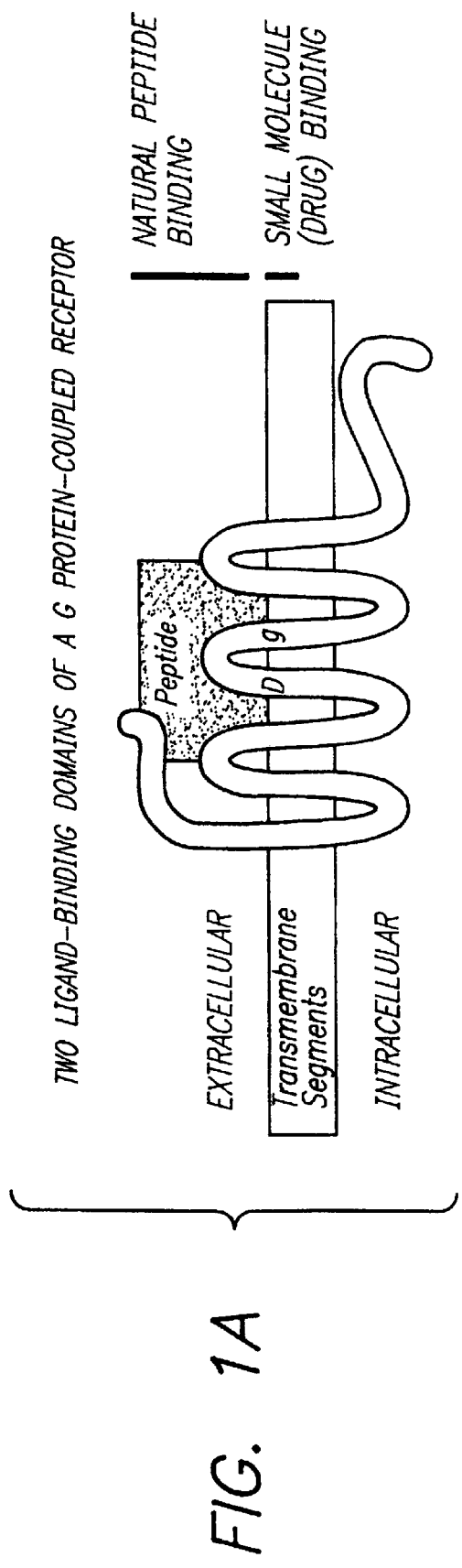
FIG. 1A is a schematic showing the structure of G protein-coupled receptors and the position of their natural ligand and synthetic small molecule domains.

Before the present method and compositions for the pharmacological control of target cell activation, and application of this method is described, it is to be understood that this invention is not limited to the particular methodology, protocols, cell lines, tissues, vectors and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "and," and "the" include plural referents unless the context clearly dictates otherwise. Thus, for example, reference to "a transformed cell" includes a plurality of such cells and reference to "the synthetic small molecule" includes reference to one or more synthetic small molecules and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the cell lines, vectors, and methodologies which are described in the publications which might be used in connection with the presently described invention. The publications discussed above are provided solely for this disclosure prior to the filing date of the present application. Nothing herein is to be construed as an admission that the inventors are not entitled to antedate such disclosure by virtue of prior invention.

Definitions

"G protein-coupled receptor" means a receptor that, upon binding of its natural peptide or nonpeptide ligand and activation of the receptor, transduces a G protein-mediated signal(s) that results in a physiological, cellular response (e.g., cell proliferation or secretion). G protein-coupled receptors form a large family of evolutionarily related proteins (see Table 1, infra). Proteins that are members of the G protein-coupled receptor family are generally composed of seven putative transmembrane domains, and thus exhibit a structure similar to that shown in FIG. 1A. G protein-coupled receptors are also known in the art as "seven transmembrane segment (7TM) receptors" and as "heptahelical receptors" (see, e.g., Schwartz, 1994, *Curr. Opin. Biotechnol.* 5:434–444).

"G protein" means a protein belonging to a large family of proteins that interact with G protein-coupled receptors to facilitate cellular responses (e.g., directly or via cellular second messengers). G proteins are composed of a heterotrimer of three separate amino acid chains (Gα, Gβ, and Gγ). Although only the Gα subunit binds GTP, "G protein" refers to the complete heterotrimer.

"G protein-coupled cellular response" means a cellular response that occurs upon ligand binding by a G protein-coupled receptor. Such G protein-coupled cellular responses include, but are not limited to, cellular proliferation, cellular secretion, cell migration, cell contraction, neurotransmission, pigment production, and apoptosis. The G protein-coupled responses of cellular proliferation and cellular secretion are of particular interest in the present invention.

"Receptor-ligand binding," "ligand binding," and "binding" are used interchangeably herein to mean physical interaction between a receptor (e.g., a G protein-coupled receptor) and a ligand (e.g., a natural ligand, (e.g., peptide ligand) or synthetic ligand (e.g., synthetic small molecule ligand)). Ligand binding can be measured by a variety of methods known in the art (e.g., detection of association with a radioactively labeled ligand).

"Signaling" means the generation of a biochemical or physiological response as a result of ligand binding (e.g., as a result of synthetic ligand binding to a G protein-coupled receptor).

"Receptor activation," "RASSL activation," and "G protein-coupled receptor activation" are used interchangeably herein to mean binding of a ligand (e.g., a natural or synthetic ligand) to a receptor in a manner that elicits G protein-mediated signaling, and a physiological or biochemical response associated with G protein-mediated signaling. Activation can be measured by measuring a biological signal associated with G protein-related signals (e.g., cell proliferation), or measurement of a second messenger affected by such signals (e.g., cAMP, calcium flux).

"Targeted cellular activation" and "target cell activation" are used interchangeably herein to mean RASSL-mediated activation of a specific G protein-mediated physiological response in a target cell, where RASSL-mediated activation occurs by binding of a synthetic small molecule to the RASSL. As used herein, cellular activation includes any of a variety of physiological processes such as cell proliferation, cell secretion, cell migration, cell contraction, pigment production and apoptosis. Activation of cell proliferation and/or secretion are of particular interest in the targeted cellular activation method of the invention.

Figure 1B:
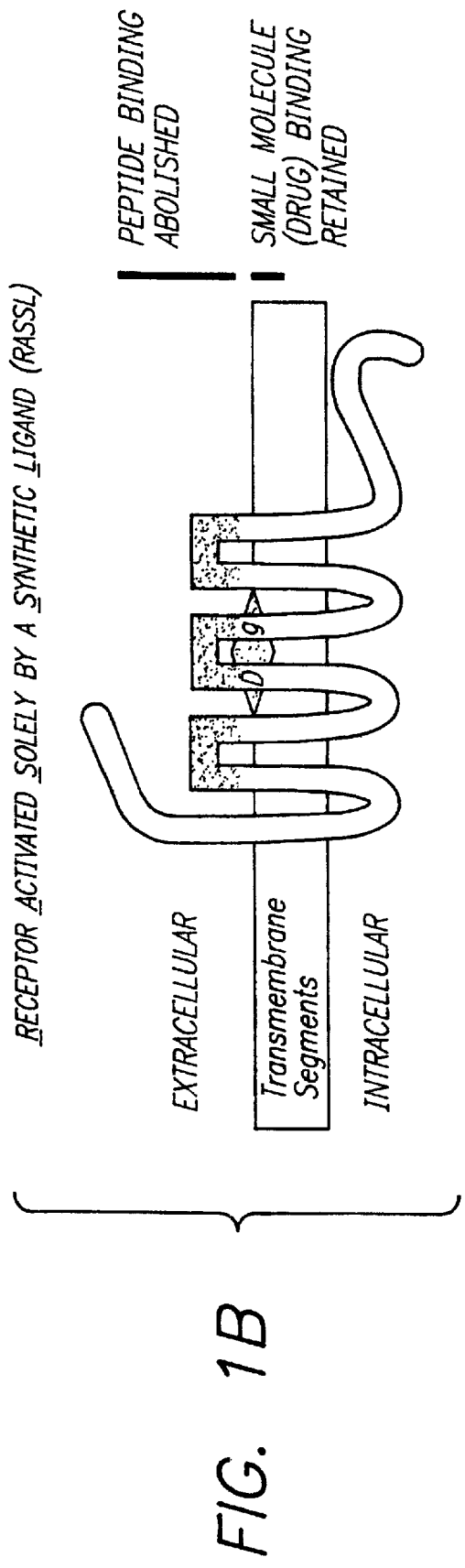
FIG. 1B is a schematic showing the structure of a RASSL appropriate for use in the present invention.

"Receptor activated superiorly by synthetic ligand," "RASSL," and "modified G protein-coupled receptor" are used interchangeably herein to mean a modified G protein-coupled receptor that 1) retains binding affinity for a synthetic small molecule and 2) has decreased binding affinity for a selected natural ligand (e.g., an endogenous, or naturally occurring, peptide or nonpeptide ligand) relative to binding by its corresponding wild-type G protein-coupled receptor. Binding of the small molecule ligand to the RASSL elicits (or suppresses) a G protein-pharmacological response in the RASSL-expressing cell. RASSLs also include modified G protein-coupled receptors that bind both a selected naturally occurring peptide or nonpeptide ligand as well as a synthetic small molecule, but have a higher affinity for small molecule binding, or are only significantly activated by binding of the synthetic small molecule. A schematic of an exemplary RASSL of the invention is shown in FIG. 1B.

"Natural ligand" and "naturally occurring ligand" of a native G protein-coupled receptor are used interchangeably herein to mean a biomolecule endogenous to a mammalian host, which biomolecule binds to a native G protein-coupled receptor to elicit (or suppress) a G protein-coupled cellular response. "Natural peptide ligand" means a natural ligand that is a polypeptide. The peptide generally binds to the native G protein-coupled receptor by interaction with an extracellular receptor domain(s) (e.g., the N-terminus, e1, e2, and/or e3) of the G protein-coupled receptor. "Natural biogenic amine ligand" means a natural ligand that is a biogenic amine (e.g., acetylcholine, serotonin, adrenaline, histamine, dopamine). Biogenic amines bind to the G protein-coupled receptors at a common binding site that involves three conserved residues on the receptor.

"Synthetic small molecule, "synthetic small molecule ligand," and "synthetic ligand" are used interchangeably herein to mean any compound made exogenously by natural or chemical means that can bind within the transmembrane domains of a G protein-coupled receptor or modified G protein-coupled receptor (i.e., RASSL) and facilitate activation (or suppression) of the receptor and concomitant activation (or suppression) of a desired. family of G proteins. In general, synthetic small molecule ligands of use in the present invention have a molecular weight of from about 100 Da to 1000 Da, and can range from about 40 Da (e.g., calcium) to about 4000 Da.

"Cellular implant" means a cell population comprising target cells expressing a RASSL of interest. Cellular implants are preferably primarily composed of RASSL-expressing target cells, but may include nontarget cells that do not express a RASSL, providing that the presence of such cells does not substantially interfere with the desired cellular response associated with ligand binding to the RASSL of the target cells. Cellular implants of the invention are suitable for introduction into a mammalian host for treatment of a disease or condition of the mammalian host (e.g., for secretion of a therapeutic product and/or growth of target cells to replace or supplement cells of similar origin in the mammalian host).

"Cell population" means a collection of living cells that can be grown in vitro and/or in vivo. Cell populations can be either homogenous or heterogenous with respect to cell type and RASSL expression.

"Therapeutic cellular product" means a cellular product useful in the treatment of a disease or condition of a mammalian host. "Therapeutic cellular products" include, but are not limited to, polypeptides, hormones, steroids, and other biological molecules that can be produced by a mammalian cell (e.g., by expression of nucleic acid either endogenous or heterologous to the mammalian cell). Nucleic acid encoding a therapeutic cellular product that is heterologous to the mammalian cell can be introduced into the cell by a variety of transformation or transfection techniques.

"Transformation" means a permanent genetic change induced in a cell following incorporation of new DNA (i.e., DNA exogenous to the cell). Where the cell is a mammalian cell, the permanent genetic change is generally achieved by introduction of the DNA into the genome of the cell.

"Transformed cell" means a cell into which (or into an ancestor of which) has been introduced, by means of recombinant DNA techniques, a DNA molecule encoding a molecule (e.g., RNA and/or protein) of interest (e.g., nucleic acid encoding a RASSL or a therapeutic cellular product).

"DNA of interest" means any DNA sequence that encodes a protein or other molecule which is desirable for expression in a target cell (e.g., for production of the protein or other biological molecule (e.g., a therapeutic cellular product) by the target cell in vitro or in vivo). The sequence encoding a DNA of interest is generally operatively linked to other sequences which are needed for its expression, e.g., a promoter.

"Promoter" means a minimal DNA sequence sufficient to direct transcription of a DNA sequence to which it is operably linked. "Promoter" is also meant to encompass those promoter elements sufficient for promoter-dependent gene expression controllable for cell-type specific, tissue-specific or inducible by external signals or agents; such elements may be located in the 5' or 3' regions of the native gene.

"Mammalian host," "mammalian subject" and "mammalian patient" are used interchangeably herein to mean any mammal in which targeted cellular activation according to the invention is desired, including human, bovine, equine, canine, and feline subjects.

"Transgenic organism" means a nonhuman organism (e.g., single-cell organisms (e.g., yeast), mammal, nonmammal (e.g., nematode or Drosophila)) having a nonendogenous (i.e., heterologous) nucleic acid sequence stably integrated into its germ line DNA (e.g., in the genomic sequence of most or all of its cells, or at least a number of cells sufficient to achieve a desired effect in the present invention).

"Transgenic animal" means a nonhuman animal, usually a mammal, having a nonendogenous (i.e., heterologous) nucleic acid sequence stably integrated into its germ line DNA (i.e., in the genomic sequence of most or all of its cells, or at least a number of cells sufficient to achieve a desired effect in the present invention). Heterologous nucleic acid is introduced into the germ line of such transgenic animals by genetic manipulation of, for example, embryos or embryonic stem cells of the host animal.

"Reversible disease transgenic animal model" and "reversible condition transgenic animal model" are used interchangeably herein to mean a RASSL-expressing transgenic animal that exhibits a symptom(s) associated with a disease or condition. In one embodiment, the transgenic animal of such reversible disease or conditions models does not exhibit the disease or condition symptom(s) in the absence of the small molecule ligand.

The invention will now be described in further detail.

Overview of Targeted Proliferation Method of the Invention

The present invention provides a method of targeted activation (or inactivation) of a response of a selected cell population by virtue of the expression of a modified G protein-coupled receptor. A modified G protein-coupled receptor is genetically engineered so that it 1) retains binding affinity for a synthetic small molecule and 2) has decreased binding affinity for a selected naturally occurring peptide or nonpeptide ligand relative to binding by its corresponding wild-type G protein-coupled receptor (e.g., the G protein-coupled receptor from which the modified G protein-coupled receptor was derived). Synthetic small molecule binding to the modified receptor induces the target cell to respond with a specific physiological response (e.g., cellular proliferation, cellular secretion, cell migration, cell contraction, or pigment production). Such modified G protein-coupled receptors are referred to herein as "Receptors Activated Superiorly by a Synthetic Ligand," or RASSLs.

The method of the invention exploits the RASSL characteristics described above to facilitate responses of RASSL-expressing target cells selectively. For example, when RASSL-expressing cells are present in a cell population that expresses neither a RASSL nor the wild-type G protein-coupled receptor from which the RASSL was derived, exposure of the cell population to the appropriate synthetic ligand that selectively binds to RASSL-expressing cells results in selective proliferation of the RASSL-expressing cells. This method, broadly referred to herein as targeted cellular activation, provides a method to amplify selectively a desired cell type in a cell population, thereby providing greater numbers of the desired target cell relative to that afforded by natural proliferation processes (FIG. 2). Furthermore, because other cells in the population do not express the RASSL (or the native G protein-coupled receptor from which the RASSL was derived), or because the wild-type G protein-coupled receptor is expressed in cells where the cellular response is benign or distinguishable from the response in the target cell, exposure to the synthetic small molecule does not result in activation of nontarget cells (i.e., the desired physiological or biochemical response is not elicited in the nontarget cells upon exposure to synthetic ligand). The presence of natural ligand generally does not substantially affect the ability of the small molecule to bind the RASSL as natural ligand binding to G protein-coupled receptors is usually transient.

RASSLs are useful to facilitate targeted cellular activation (or suppression) in a variety of in vitro and in vivo settings. For example, RASSLs can be used to induce targeted, proliferative amplification of transfected cells in in vitro culture, e.g., as a means for selecting for cells that express a RASSL and respond with a desired physiological response upon RASSL stimulation, and/or as a means for expanding a desired cell type from a primary cell culture. In addition, RASSL stimulation is useful in increasing secretion of a cellular product of interest by cells in vitro or in vivo, to elicit proliferation of cells transformed during gene therapy and to gain pharmacological control in vivo of transformed cells expressing therapeutic genes. Additional uses of the method and compositions of the invention are described in detail below (see "Utilities")

G protein-coupled Receptors (Background)

G protein-coupled receptors, which form a large family of evolutionarily related proteins, are encoded by over 600 different, currently described genes from diverse species (see Table 1 for exemplary G protein-coupled receptors families). By some estimates, there are over 1000 separate genes encoding G protein-coupled receptors in the human genome alone, accounting for 1–2% of all human genes. G protein-coupled receptors are classified according to the type of ligand bound by the receptor (e.g., peptide receptors, natural nonpeptide small molecule receptors, and orphan receptors (i.e., receptors for which the natural ligand is not presently known)). For a complete list of currently known G protein-coupled receptors, see the following sites on the world wide web:

receptor.mgh.harvard.edu/GCRDBHOME.html
swift.embl-heidelberg.de/7tm/
mgddkl.niddk.nih.gov:8000/GPCR.html expasy.hcuge.ch/cgi-bin/ProMod-GPCR.pl
expasy.hcuge.ch/cgi-bin/lists?7tmrlist.txt.
Each ligand-binding receptor subclass shown in Table 1 represents a G protein-coupled receptor subfamily comprising up to 50 genes. G protein-coupled receptors facilitate regulation of cell growth in a wide variety of tissues.

TABLE 1

G protein-coupled Receptors

| | Synthetic Small Mol Agonist |
|---|---|
| G protein-coupled receptor families having peptide natural ligands | |
| Angiotensin receptors | + |
| Bombesin receptors | |
| Bradykinin receptors | |
| Calcitonin, parathyroid hormone, secretin receptors | |
| Chemokine receptors | |
| Chemotactic peptide receptors (fMLP) | |
| CSA receptor | + |
| Cholecystokinin/gastrin receptors | + |
| Corticotropin (ACTH) receptor | |
| Endothelin receptors | |
| Glycoprotein hormones receptors (TSH, FSH, LH) | |
| Melanocortins receptors | |
| Neuropeptide Y receptors | |
| Neurotensin receptors | |
| Opioid receptors: | |
| mu opioid receptor | + |
| delta opioid receptor | + |
| kappa opioid receptor | + |
| nociceptin, opioid receptor | + |
| Releasing hormone receptors (LHRH, GHRH) | |
| Somatostatin receptors | |
| Tachykinin receptors | |
| Thrombin/protease receptors | |
| Vasopressin/oxytocin receptors | |
| G protein-coupled receptor families having small molecule natural ligands (biogenic Amines) | |
| Acetylcholine (muscarinic) receptors | + |
| Adrenergic receptors | + |
| Dopamine receptors | + |
| Histamine receptors | + |
| Serotonin receptors | + |
| G protein-coupled receptor families having natural small molecule agonist ligands: lipids and other nonamines | |
| Adenosine and other adenine nucleotide receptors | + |
| Cannabinoids receptors | + |
| Prostanoids and PAF receptors | + |
| Metabotropic glutamate | + |
| Calcium receptor | + |
| Other Receptor Families | |
| Odorant/olfactory and gustatory receptors | |
| Opsins | |
| Viral receptors | |
| Orphan receptors | |

G protein-coupled receptors share a high degree of structural and functional homology. For example, G protein-coupled receptors that bind peptides as their natural ligands are composed of seven transmembrane helices (TMHs) separated by three intracellular loops (i1, i2, and i3), the N-terminus, and three extracellular loops (e1, e2, e3) (FIG. 1A). Peptides bind the receptor's extracellular loops, while small molecules bind the receptor's transmembrane domains (see, e.g., Schwartz, supra; Cascieri et al., 1995, *J. Pharmacol. Toxicol. Meth.* 33:179–185). The intracellular domains of the receptor interact with G proteins and are responsible for generating specific intracellular signals associated with cell growth. The structure and function of G protein-coupled receptors are the subjects of several recent reviews (Conklin et al., 1993, *Cell* 73:631–41; Schwartz, 1994, supra; Cascieri et al., supra). Because peptide binding, small molecule binding, and G protein interaction are mediated by distinct regions of G protein-coupled receptors (the extracellular loops, TMH region, and intracellular loops, respectively), G protein-coupled receptors can be modified to decrease or even completely eliminate binding of a selected natural ligand without substantially affecting either small molecule binding or interaction of the receptor with G proteins.

In contrast to G protein-coupled receptors, G proteins have a somewhat more limited repertoire. The same essential 4 major classes of G proteins ($G_s$, $G_i$, $G_q$ and $G_{12}$) are expressed in all mammalian cell types (e.g., in every cell type of the human body). Furthermore, the cellular response elicited by activation of these different G protein classes varies from cell type to cell type. Stated differently, the signals transmitted to the cell by activation of these 4 different G protein families have different meanings within the various cellular environments. For example, proliferation of blood-forming cells is associated with $G_i$ activation, while $G_i$ activation is also associated with neurotransmission in the brain or slowing of the heart rate. $G_q$ activation is associated with proliferation of hepatic cells, and certain secretory cells of the lung, breast and stomach (Dhanasekaran et al., 1995, *Endocrine Rev.* 16:259–270). Table 2 provides several examples of the relationship between a stimulus (e.g., natural G protein-coupled receptor ligand), the cell type affected, the G protein subfamily activated, the effector (e.g., second messenger) molecule that mediates the response, and the cellular response. The various G protein families and the various G protein-mediated physiological responses are the subjects of several reviews (see, e.g., Dhanasekaran et al., 1995, *Endocrine Rev.* 16:259–270; Linder et al., July 1992, *Sci. Amer.* 267:56–61; Shenker, 1995, *Baillière's Clin. Endocrinol. Metab.* 9:427–451; Spiegel, 1992, *Curr. Opin. Cell Biol.* 4:203–211; Coughlin, 1995, *Curr. Opin. Cell Biol.* 6:191–197).

The specificity of G protein activation is mediated at the level of the G protein-coupled receptor. Each G protein-coupled receptor activates a distinct G protein subset (class) which elicits different physiologic effects depending on the cell type. Of the four major classes of G proteins ($G_s$, $G_i$, $G_q$ and $G_{12}$), each class is associated with cell proliferation in a different cell type. Through selective stimulation of members of this limited set of G proteins, the body thus efficiently regulates many different signals and cellular responses.

TABLE 2

Relationship Between Stimulus. G protein Families, and Physiological or Biochemical Effect

| Stimulus | Affected Cell Type | G Protein | Effector | Effect |
|---|---|---|---|---|
| Epinephrine, glucagon | Liver cells | $G_s$ | Adenylyl cyclase | Breakdown of glycogen |
| Epinephrine, glucagon | Fat cells | $G_s$ | Adenylyl cyclase | Breakdown of fat |
| Luteinizing hormone | Ovarian follicles | $G_s$ | Adenylyl cyclase | Increased estrogen and progesterone |
| Thyroid stimulating hormone | Thyroid cells | $G_s$ | Adenylyl cyclase | Proliferation of thyroid cells |
| Chemokines | Lymphocytes | $G_i$ | Adenylyl cyclase | Chemotaxis; proliferation |

TABLE 2-continued

Relationship Between Stimulus, G protein Families, and Physiological or Biochemical Effect

| Stimulus | Affected Cell Type | G Protein | Effector | Effect |
|---|---|---|---|---|
| Acetylcholine | Heart muscle cells | Gi | Calcium and potassium channels, adenylyl cyclase | Slowed heart rate and decreased pumping force |
| Enkephalins, endorphins, opioids | Brain neurons | Gi/Go | Calcium and potassium channels, adenylyl cyclase | Changed electrical activity of neurons |
| Angiotensin | Smooth muscle cells in blood vessels | Gq | Phospholipase C | Muscle contraction; elevation of blood pressure |
| Vasopressin | Liver cells (hepatocytes) | Gq | Phospholipase C | Proliferation |
| Odorants | Nose neuro-epithelial cells | Golf | Adenylyl cyclase | Detection of odorants |
| Light | Rod and cone cells of the retina | Gt | Cyclic GMP phosphodiesterase | Detection of visual signals |
| Pheromone | Baker's yeast | GPA1 | Unknown | Mating of cells |

Construction of RASSLs

Any G protein-coupled receptor having separable domains for: 1) natural ligand (e.g., peptide ligand or biogenic amine) binding; 2) synthetic small molecule binding; and 3) G protein interaction can be modified to produce a RASSL for use in the method of the invention. In general, any G protein-coupled receptor that is a member of the G protein-coupled receptor family may be used to generate a RASSL of the invention. Exemplary G protein-coupled receptors having these characteristics include, but are not limited to, those receptors listed in Table 1.

Of particular interest are those G protein-coupled receptors having a peptide as its natural ligand, such as those G protein-coupled receptors under the subheading "Peptide Ligands" in Table 1. G protein-coupled receptors that bind peptide as their natural ligand, and are of particular interest for modification to produce a RASSL of the invention, include, but are not limited to: Type-1 Angiotensin II, Type-1a Angiotensin II, Type-1B Angiotensin II, Type-1C Angiotensin II, Type-2 Angiotensin II Receptor, Neuromedin-B, Gastrin-releasing Peptide, Bombesin Subtype-3, B1 Bradykinin, B2 Bradykinin, Interleukin-8 A, Interleukin-8 B, FMet-Leu-Phe, Monocyte Chemoattractant Protein 1, C—C Chemokine Receptor Type 1, C5a Anaphylatoxin, Cholecystokinin Type A, Gastrin/cholecystokinin Type B, Endothelin-1, Endothelin B, Follicle Stimulating Hormone (FSH-R), Lutropin-choriogonadotropic Hormone (LH/CG-R), Adrenocorticotropic Hormone (ACTH-R), Melanocyte Stimulating Hormone (MSH-R), Melanocortin-3, Melanocortin-4, Melanocortin-5, Melatonin Type 1A, Melatonin Type 1B, Melatonin Type 1C, Neuropeptide Y Type 1, Neuropeptide Y Type 2, Neurotensin, Delta-type Opioid, Kappa-type Opioid, Mu-type Opioid, Probable Opioid Receptor (now called Opioid-like or Nociceptin Receptor), Gonadotropin-releasing Hormone, Somatostatin Type 1, Somatostatin Type 2, Somatostatin Type 3, Somatostatin Type 4, Somatostatin Type 5, Substance-P, Substance-K, Neuromedin K, Vasopressin V1a, Vasopressin V1B, Vasopressin V2, Oxytocin, Galanin, Calcitonin, Calcitonin A, Calcitonin B, Growth Hormone-releasing Hormone, Parathyroid Hormone/parathyroid Hormone-related Peptide, Pituitary Adenylate Cyclase Activating Polypeptide Type I, Secretin, Vasoactive Intestinal Polypeptide 1, and Vasoactive Intestinal Polypeptide 2. Biogenic amine receptors, especially the serotonin receptors, are also of particular interest for production of RASSLs according to the invention. Exemplary biogenic amine receptors are provided in Table 1.

Modification of native G protein-coupled receptors to produce RASSLs of the invention can be accomplished using a variety of recombinant techniques well known in the art (see, e.g., Sambrook et al. *Molecular Cloning: A Laboratory Manual,* 2nd Ed., 1989, Cold Spring Harbor Laboratory Press, Cold Spring Harbor, N.Y.). In general, RASSLs are generated by first cloning cDNA encoding a native G protein-coupled receptor in an expression vector according to methods well known in the art. For example, G protein-coupled receptor-encoding DNA can be isolated by PCR amplification from a cDNA library and the PCR product subsequently subcloned into a mammalian expression vector using standard techniques. Several G protein-coupled receptors have been cloned and sequenced.

The amino acid sequence of the G protein-coupled receptors is determined using standard sequencing and/or DNA manipulation software (e.g., DNA Strider, MacVector, Geneworks, GCG, Eugene). The amino acid sequence is analyzed to determine the position of the seven transmembrane segments characteristic of G protein-coupled receptors. Due to the structural homology of G protein-coupled receptors, the position of these segments can be determined by comparison to the amino acid sequences and three-dimensional structures of other G protein-coupled receptors. Predicted transmembrane domains of several G protein-coupled receptors are known in the art, and are available in several public domain World Wide Web sites. See, for example the following sites on the world wide web:
receptor.mgh.harvard.edu/GCRDBHOME.html
swift.embl-heidelberg.de/7tm/
mgddkl.niddk.nih.gov:8000/GPCR.html
expasy.hcuge.ch/cgi-bin/ProMod-GPCR.pl
expasy.hcuge.ch/cgi-bin/lists?7tmrlist.txt.
Additional predictions about the structural domains of the native G protein-coupled receptors are available publicly on the SWISS-PROT database, which can be accessed on the above sites. Methods for predicting three-dimensional structures of any G protein-coupled receptor are known in the art. In general, these methods predict G protein-coupled receptor structure by identification of the position of specific residues shared by subfamilies of G protein-coupled receptors. In addition, these methods analyze the amino acid sequence to identify stretches of hydrophobicity predictive of the characteristic seven transmembrane segments. For a review, see Baldwin, 1994, *Curr. Opin. Cell Biol.* 6:180–190.

G protein-coupled receptors are generally composed of seven transmembrane helices (TMHs) separated by three intracellular loops (i1, i2, and i3), the N-terminus, and three extracellular loops (e1, e2, e3) (FIG. 1A). The four extracellular segments of the receptor (e1, e2, e3, and the N-terminus) contain the sequences that facilitate natural ligand binding, but are generally not involved directly in small molecule binding (Schwartz, supra). These four extracellular segments are characterized as follows: 1) The "N-terminus," which includes all residues before the first transmembrane segment, and is usually about 10–600 residues in length; 2) the "first extracellular loop" (e1), which is defined by the residues between the second and third transmembrane domains and is usually from about 7 to 20 amino acid residues in length; 3) the "second extracellular loop" (e2), which is defined by the residues between the fourth and fifth transmembrane domains and is usually between 10–35 residues in length; 4) the "third extracellular loop" (e3), which is defined by the residues between the sixth and seventh transmembrane domains and is usually between 7–20 residues in length.

RASSLs are generated from the native G protein-coupled peptide receptor by mutation of one or more residues in at least one of the extracellular segments (e1, e2, e3, and/or the N-terminus) of the receptor. Mutations include, but are not limited to, nucleotide substitutions, additions, deletions, and/or modification so as to produce an amino acid alteration (e.g., a conservative or nonconservative amino acid substitution, preferably nonconservative).

Where the RASSL is made from a peptide receptor, mutagenesis is targeted to the extracellular loops of the receptor. Where the RASSL is made from a biogenic amine receptor, mutagenesis is targeted at the known binding sites of the biogenic amines located at three discrete sites in the transmembrane domains of the receptor (see, e.g., Schwartz, supra; Strader et al., 1991, *J. Biol. Chem.* 266(1):5–8; Strader et al., 1994, *Ann. Rev. Biochem.* 63:101–32; Cascieri et al., 1995, *J. Pharmacol. Toxicol. Meth.* 33:179–185; Schwartz, 1994, *Curr. Opin. in Biotech.* 5:434–444; Baldwin, 1994, *Curr. Opin. in Cell Biol.* 6:180–190). Mutations at these discrete sites dramatically decrease binding by the natural biogenic amines, while preserving binding and activation by synthetic small molecule drugs (Strader et al. 1991 *J. Biol. Chem.* 266:5–8).

Alternatively, or in addition, RASSLs can be generated by the production of chimeric proteins composed of sequences encoding two different G protein-coupled receptors, each having distinct natural ligand binding and/or small molecule binding characteristics (e.g., bind natural ligand with different affinities, bind different natural ligands, bind the same or different small molecule ligands). Methods for nucleic acid manipulation are well known in the art (see, e.g., Sambrook et al., supra).

Changes and/or modifications in the amino acid sequence of a native G protein-coupled receptor can comprise a single amino acid change and may comprise deletion and/or substitution of over 600 residues in receptors with large extracellular domains such as the TSH receptor. In general, the RASSL mutants contain at least one amino acid change, usually at least 2 to 5 amino acid changes, generally about 5 to 10 amino acid changes, and normally 10 to 20 amino acid changes and can contain 50 amino acid changes or more. Preferably, the number of amino acids altered in the RASSL relative to the native G protein-coupled receptor from which it is derived is a number sufficient to provide the desired RASSL characteristics (e.g., decreased natural ligand binding relative to small molecule binding) without significantly adversely affecting the ability of the RASSL to bind synthetic small molecule ligand and elicit the desired cellular response.

Synthetic small molecule ligands that stimulate the native G protein-coupled receptor, and thus can be used to activate the RASSL derived from that native. receptor, are well known in the art (see, e.g., Freidinger, 1993, *Prog. Drug Res.* 40:33–98), or can be identified using the exemplary screening assays as described below. Preferably, the small molecule ligand is a high affinity agonist or antagonist, more preferably agonist, for the RASSL.

Preferably, a RASSL is modified with respect to its corresponding native G protein-coupled receptor in that the RASSL exhibits binding for a selected natural ligand that is decreased, preferably substantially decreased, more preferably substantially eliminated, relative to binding of the ligand by its corresponding native G protein-coupled receptor. Therefore, RASSL activity is relatively unaffected by natural fluctuations of the selected natural ligand (e.g., natural hormones). RASSL binding of the selected natural ligand is decreased by at least 5-fold, preferably 10-fold, more preferably 50-fold, still more preferably 75-fold, and may be decreased 100-fold or more relative to binding by the RASSL's corresponding native G protein-coupled receptor.

Alternatively, RASSLs suitable for use in the invention may retain binding to the selected natural ligand, but exhibit reduced activation upon such natural ligand binding. Such RASSLs may have decreased responsiveness to the selected natural ligand, yet still retain superior responsiveness to binding of appropriate synthetic small molecule ligand. Alternatively, the RASSL can be modified such that a small molecule ligand that acts as an antagonist for the corresponding native G protein-coupled receptor instead acts as an agonist upon binding the RASSL.

The RASSL binds the appropriate synthetic small molecule with the same, increased, or similar affinity relative to the native G protein-coupled receptor. Preferably, a RASSL binds its synthetic small molecule with equivalent, nearly equivalent, or greater affinity than its corresponding native G protein-coupled receptor. Most importantly, the RASSL is superiorly activated by the small molecule drugs as compared to the natural ligand (i.e., activated to a greater or more significant extent by binding of the small molecule ligand than by binding to a selected natural ligand at a similar concentration. Preferably, RASSL binding to the selected natural ligand is decreased relative to selected natural ligand binding by the native G protein-coupled receptor from which the RASSL is derived, and RASSL small molecule binding is relatively unchanged relative to small molecule binding by the native G protein-coupled receptor.

In general, the RASSL expressed in the target cell is a derived from a native G protein-coupled receptor that is not normally expressed in the target cell. The RASSL thus provides a means to elicit a response (e.g., activation or suppression) in a desired subfamily of G proteins without affecting activity of other G protein-coupled receptors. For example, while nontarget cells in the cell population may express other G protein-coupled receptors capable of activating the desired G protein subfamily, these endogenous G protein-family receptors are not activated by the small molecule ligand that activates the RASSL expressed in the target cells. Alternatively, the native G protein-coupled receptors capable of binding the small molecule ligand activate a G protein subfamily that in turn elicits a physiological or biochemical response distinguishable from the response desired in the target cells (e.g., exposure to the small molecule may cause pain relief (or some benign response) in nontarget cells, but elicit the desired cellular response in the target cell type). Because there are many synthetic small molecule drugs that can be used as RASSL ligands, it is possible to choose a small molecule drug that is known to have benign effects on people or animals when acting on native G protein-coupled receptors. The G protein-mediated responses that result from activation of introduced RASSLs are the responses of interest in the present invention.

RASSLs can also be characterized by the ratio of synthetic ligand binding affinity to binding affinity of a selected natural ligand. Preferably, RASSLs of the invention exhibit a high small molecule ligand binding to selected natural ligand binding ratio, and exhibit small molecule ligand:selected natural ligand binding ratios of at least 0.8, preferably at least 1.0, more preferably at least 5, even more preferably 10, still more preferably 100 or higher. Preferably, RASSLs exhibit binding ratios that are 2-fold greater, preferably 5-fold greater, more preferably 10-fold greater, even more preferably 50- to 100-fold greater than the small molecule ligand:selected natural ligand binding ratio of a native G protein-coupled receptor.

RASSLs can also be characterized by the ratios of the level of activation by exposure to synthetic ligand to the level of activation by exposure to a selected natural ligand ("activation ratio"). Activation levels can be measured by measuring a biochemical or physiological signal (e.g., cell proliferation), or a second messenger molecule associated with such a signal (e.g., cAMP). Preferably, RASSLs of the invention exhibit a high small molecule ligand activation to selected natural ligand activation ratio, and exhibit small molecule ligand:selected natural ligand activation ratios of at least 0.8, preferably at least 1.0, more preferably at least 5, even more preferably 10, still more preferably 100 or higher. Preferably, RASSLs exhibit activation ratios that are 2-fold greater, preferably 5-fold greater, more preferably 10-fold greater, even more preferably 50- to 100-fold greater than the small molecule ligand:selected natural ligand activation ratio of a native G protein-coupled receptor.

RASSLs appropriate for use in the method of invention may interact with either the same or different G proteins as the native G protein-coupled receptor from which the RASSLs are derived. Because G protein interaction is facilitated by a receptor domain distinct from that of small molecule binding, G protein-coupled receptors can be modified to alter G protein coupling via alteration of the intracellular domains without affecting the peptide and small molecule binding domains of the receptor. Therefore, a single ligand/RASSL combination can be used to control the G protein-mediated response of the native G protein-coupled receptor from which the RASSL was derived, or the RASSL can be modified for use in activation of any of a wide variety of G protein responses.

The preferred G protein(s) with which a desired RASSL interacts is determined by a variety of factors, including the cell type to be activated by the RASSL, and the desired type, kind, or extent of the cellular response to be activated by RASSL activation. For example, in cells where $G_i$ protein family activation facilitates blood-forming cell proliferation, the RASSL used in the method of the invention is derived from a native G protein-coupled receptor that interacts with the $G_i$ protein family, or is modified so that it interacts with the $G_i$ protein family. In contrast, if the RASSL is derived from a G protein-coupled receptor that normally interacts with $G_i$ protein, and this RASSL is to be used to facilitate proliferation of lung or stomach secretory cells, the RASSL is modified so that it interacts with $G_q$ protein, the G protein that facilitates proliferation of lung and stomach secretory cells. Examples of G protein-coupled receptors that are modified with respect to G protein interaction have been described (see, e.g., Liu et al., 1995, *Proc. Natl. Acad. Sci. USA* 92:11642–11646; Kobilka, 1992, *Ann. Rev. Neurosci.* 15:87–114).

RASSLs derived from G protein-coupled receptors that bind nontoxic synthetic small molecule ligands (e.g., which can be safely and effectively administered to a mammalian host by oral and/or intravenous administration) are of particular interest. The kappa opioid receptor (KOR) and serotonin receptors are examples of G protein-coupled receptors that are activated by binding of specific synthetic small molecule drugs suitable for human use.

The native KOR activates $G_i$ protein in neural cells, while the serotonin receptors activate the $G_q$, $G_i$ and $G_s$ family of G proteins in many tissues. The KOR and serotonin receptors do not facilitate proliferation through activation of their respective G proteins in their native cell types (i.e., KOR activation does not result in cell proliferation in neural cells, and serotonin receptor activation does not result in cell proliferation in liver cells). However, the same signaling pathways activated by KOR and serotonin receptors in their native cell types ($G_i$ pathway and $G_q$ pathway, respectively) can be proliferative if activated in a different cell type.

Because $G_q$, $G_s$ and $G_i$ trigger proliferation in different tissues, KOR- or serotonin receptor-derived RASSLs are useful in selectively targeting proliferation in tissues in which $G_i$, $G_s$ or $G_q$ signals facilitate proliferation. For example, KOR-derived RASSLs can be designed to retain activity in $G_i$ protein activation and facilitate targeted proliferation in blood-forming cells, while serotonin-receptor-derived RASSLs can be designed to retain activity in $G_q$, $G_i$ or $G_s$ protein activation and facilitate targeted proliferation in hepatic cells and certain secretory cells of the lung, breast and stomach.

Alternatively, KOR and serotonin receptor RASSLs can be designed so that the RASSL retains the ability to bind the synthetic small molecule bound by native KOR or native serotonin receptors, but altered with respect to the G protein family activated by the RASSL. For example, a KOR-derived RASSL can be designed to interact with G proteins other than those of the $G_i$ protein family, and thus facilitate proliferation in cell type(s) that proliferate in response to activation of other G proteins. Alteration of G protein interaction can be accomplished by alteration of the native receptor's intracellular domain without substantially affecting the ligand-binding portion of the receptor.

Kappa Opioid Receptor-derived RASSLs

The KOR is a member of the opioid receptor family, which also includes the mu and delta opioid receptors. The KOR is implicated in neurotransmission in its native cell type. In contrast to KOR, mu receptor activation is associated respiratory depression, and addictive effects of opiates. KOR has distinct binding domains for its synthetic small molecule ligands, and for its natural ligand dynorphin, which is found endogenously in the nervous system, including the peripheral nerves that penetrate most organs (Xue et al., 1994, *J. Biol. Chem.* 269:30195–30199). Thus, KOR-derived RASSLs retain small molecule binding activity and are preferably substantially unresponsive to dynorphin binding or substantially reduced in dynorphin binding activity.

Several KOR-specific synthetic small molecule agonists have been developed including, pentazocine (TALWIN™), Spiradoline, U-62066E, U-62066, and U50488H (Pharmacia-Upjohn), ICI-204,488 (Zeneca), DUP 747 (Dupont-Merck), and CI-977 (Parke-Davis). The structural formulas for pentazocine, DUP 747, CI-977, and Spiradoline are shown in FIG. 3. Several of these compounds (e.g., pentazocine and Spiradoline) are orally available, and are safe (in humans and primates) and nonaddictive (in rats and primates). Any of these synthetic compounds are suitable for activation of KOR-derived RASSLs in the targeted activation method of the invention, and are likely to have relatively few side effects. For example, pentazocine, a mixed KOR agonist/mu receptor antagonist, is an orally available, weakly analgesic drug with low addictive potential, that has been used safely by thousands of people for over 15 years.

In addition, two opioid antagonists, Naloxone™ (available generically as Naracn™) and Naltrexone™ (available generically as Trexan™, DuPont-Merck) have been used clinically for many years and are thus of particular interest for use in the present invention. Both of these compounds are safe and nonaddictive when given to people. Both of these drugs can be used as agonists of the opioid receptors (including the KOR) if those receptors have been mutated at a conserved position in each of these receptors (Claude et al., 1996, *PNAS*, 93:5715–5719).

Serotonin Receptor-derived RASSLs

Figure 4:
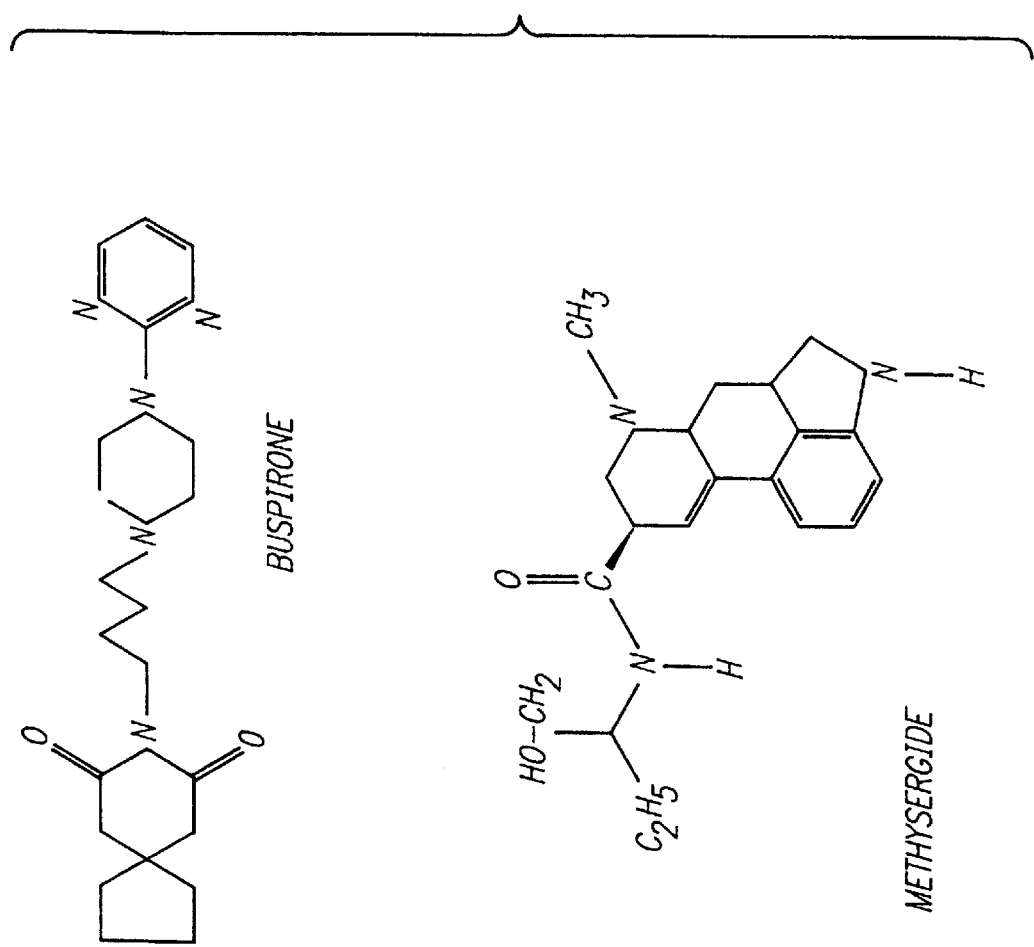
FIG. 4 is a schematic of the structural formulas of buspirone and methysergide, exemplary synthetic small molecule antagonists of the serotonin receptor.

Serotonin receptor-derived RASSLs are also of particular interest for use in the targeted cellular response method of the invention. The biogenic amine serotonin, a neurotransmitter and hormone widely utilized in the body, is the natural ligand for serotonin receptors. Synthetic small molecule ligands which bind and activate serotonin receptors are widely used to treat clinical depression (e.g., Buspirone, known as Buspar™, Mead Johnson). In addition, orally available serotonin receptor antagonists are used clinically to treat headaches (e.g., methysergide, known commercially as Sansert™, Novartis). The structural formulas for Buspar™ and Sansert™ are shown on FIG. 4. By analogy to opioid receptor mutants, proper mutation of serotonin receptors may allow use of these serotonin antagonists as agonists.

Synthetic Small Molecules

Any small molecule, preferably a synthetic small molecule, that can bind within the transmembrane domains of a RASSL and facilitate RASSL-mediated activation of a desired family of G proteins is suitable for use in the method of targeted activation method of the invention. In contrast to the natural peptide ligands of G protein-coupled receptors which typically have molecular weights of 2000–6000 Da, synthetic small molecule ligands of G protein-coupled receptors have molecular weights of 100–1000 Da. In general, any synthetic drug is suitable for use in the invention if it binds the RASSL in a unique manner distinguishable from natural ligand binding.

Synthetic small molecules useful in the present invention include synthetic small molecules generated by either a natural (e.g., isolated from a recombinant cell line) or chemical means (e.g., using organic or inorganic chemical processes).

Where the RASSL-expressing target cells are present in the brain of the subject, the synthetic small molecule is preferably of a molecular weight and net ionic charge that permits it to cross the blood-brain barrier following oral or parenteral (e.g., intravenous) administration. Typically molecules that cross the blood brain barrier are less charged than peptide molecules. Synthetic drugs can be made that do, or do not cross the blood-brain barrier depending on the number of charged groups on the molecule (see, e.g., Freidinger, 1993, *Prog. Drug Res.* 40:33–98). Smaller molecules, e.g., less than 4000 Da, are also more likely to cross the blood-brain barrier.

Several synthetic small molecules that bind and activate native G protein-coupled receptors are known in the art and are useful in the present invention. Additional synthetic small molecules suitable for use in the present invention can be identified by screening candidate compounds for binding to native G protein-coupled receptors or to RASSLs. For example, a cell line expressing a RASSL of interest is exposed to varying concentrations of a compound to be tested for RASSL binding. RASSL binding is detected by induction of a cellular response (e.g., cellular growth, secretion, etc.) upon exposure to the test compound, but not in the presence of a control compound that does not bind the RASSL and/or does not induce cellular activation. The cellular response can be detected by a variety of methods known in the art, and will vary according to the type of cellular response elicited by synthetic small molecule binding. For example, the cellular response of proliferation can be detected by cellular incorporation of a radioactive DNA component (e.g., $^3$H-thymidine). Where the cellular response is secretion, detection of the amount of a secreted protein in the cell supernatant is indicative of activation of the receptor. RASSL activation can also be detected by measuring intracellular cAMP or calcium levels (calcium flux).

Synthetic small molecule drugs have several advantages over peptide drugs. Small molecule drugs can be more economically produced, administered orally without substantial activity loss, and have long biological half-lives relative to peptide drugs. Numerous synthetic small molecule drugs have been developed, or are currently under development, for specific G protein-coupled receptors, including the receptors for angiotensin II, neurokinins, oxytocin, vasopressin, somatostatin, bombesin, thyrotropin-releasing hormone, endothelin, C5a, luteinizing hormone-releasing hormone, motilin and neuropeptide Y (see Table 1, and recent review by Freidinger, 1993, *Prog. Drug Res.* 40:33–98). RASSLs that do not bind a selected natural ligand, but bind and respond to synthetic drugs, can be used in the method of the invention to control a variety of physiological processes such as proliferation, secretion, cell migration, cell contraction, pigment production and apoptosis, depending on the cell type expressing the RASSL.

Screening for RASSLs and RASSL Activation

RASSLs of the invention can be identified by screening compounds for their ability to bind and activate the RASSL-expressing cells. Methods for detection of receptor binding and detection of G protein-mediated responses are well known in the art. Binding studies can be accomplished using competitive binding assays using radioactively labeled ligand. The binding properties of the selected natural ligand, and the small molecule ligand are compared to the binding properties of the wild-type receptor.

RASSLs can also be screened on the basis of the receptor's activation ratio (level of activation in response to small molecule binding relative to level of activation in response to exposure to a selected natural ligand). Activation levels can be determined using standard biochemical measurements associated with G protein-coupled receptor activation. For example, RASSL activation can be determined by measuring the changes in intracellular cAMP levels, inhibition of cAMP accumulation (e.g., as in RASSLs derived from the KOR), accumulation of inositol phosphates (e.g., as in RASSLs derived from serotonin receptors), or calcium mobilization (e.g., as in RASSLs derived from the serotonin receptor). Methods for detecting these and other G protein-mediated activation signals are well known in the art (see, e.g., Conklin et al., 1993, *Nature* 363:274–276; Wong et al., 1992, *Science* 255;339–342; Federman et al., 1992, *Nature* 354:159–161.)

RASSLs can also be further screened for their ability to mediate the desired physiological or biochemical response in the target cell. For example, the ability of a RASSL to mediate cell proliferation can be detected by incorporation of the $^3$H-thymidine in the target cells (see, e.g., Conklin et al., 1988, *Proc. Natl. Acad. Sci. USA* 85:8698–8702).

Alternatively, RASSL-mediated cell proliferation can be detected by co-culturing in vitro RASSL-expressing cells with cells that do not express the RASSL. Preferably, the RASSL-expressing target cells compose only about lo or less of the total cell population. The cells are then cultured in the presence of the RASSL small molecule agonist for several hours, days, or weeks. The number of RASSL positive cells in the cell population is then detected by fluorescence-activated cell sorting (FACS). RASSLs that promote a significant increase in the number of target cells over time are suitable for use in the invention.

RASSL Selection

The RASSL selected for expression in a mammalian host will vary with a variety of factors including, but not limited to, the physiological response to be activated (e.g., the G protein subfamily that must be activated in the selected target cell type in order to elicit the desired physiological response), and the cell type(s) or tissues in which targeted cellular activation is desired. Where the selected natural ligand is endogenous to the tissue in which the target cells are present, the RASSL preferably has a higher binding affinity for synthetic small molecule ligand in the presence of the selected natural ligand. Preferably, the RASSL expressed by the target cells binds and is activated by a synthetic small molecule that is not bound by endogenous G protein-coupled receptors expressed by the RASSL-expressing target cell itself and/or by nontarget cells present in the cell population (e.g., surrounding cells or tissue) surrounding the RASSL-expressing target cell.

Vectors and Constructs

Any of a variety of vectors (e.g., viral vectors, bacterial vectors, or vectors capable of replication in eukaryotic and prokaryotic hosts) can be used in accordance with the invention to produce RASSL-expressing cells Preferably, the vector is capable of replication in both eukaryotic and prokaryotic hosts in order to facilitate efficient production of RASSL-encoding DNA for use in the method of the invention. Numerous vectors that can replicate in eukaryotic and prokaryotic hosts are known in the art and are commercially available.

The vector selected will vary according to whether the target cells to be activated are present in an in vitro culture, or are transformed for use in ex vivo or in vivo gene therapy protocols. For example, where the target cells are to be transformed in vivo, the preferred vector may be a stable integrating vector or a stable nonintegrating vector. Examples of such vectors include viral vectors and artificial chromosomes (e.g., human artificial chromosomes).

Preferably, the DNA construct contains a promoter to facilitate expression of the RASSL-encoding DNA within the target cell. Preferably the promoter is a strong, eukaryotic promoter. Exemplary eukaryotic promoters include promoters from cytomegalovirus (CMV), mouse mammary tumor virus (MMTV), Rous sarcoma virus (RSV), and adenovirus. More specifically, exemplary promoters include the promoter from the immediate early gene of human CMV (Boshart et al., 1985, *Cell* 41:521–530) and the promoter from the long terminal repeat (LTR) of RSV (Gorman et al., 1982, *Proc. Natl. Acad. Sci. USA* 79:6777–6781). Of these two promoters, the CMV promoter is preferred as it provides for higher levels of expression than the RSV promoter.

Other components of vectors suitable for use include a marker(s) (e.g., an antibiotic resistance gene (such as an ampicillin resistance gene) or β-galactosidase) to aid in selection of cells containing the construct, an origin of replication for stable replication of the construct in a bacterial cell (preferably, a high copy number origin of replication), a nuclear localization signal, or other elements which facilitate production of the DNA construct, the protein encoded thereby, or both. Such selective markers can be used instead of or in addition to selection of the RASSL-expressing target cells by detection or selection of a RASSL-stimulated cellular response (e.g., for selection of cells having both RASSL-encoding DNA and DNA encoding a therapeutic cellular product of interest).

For eukaryotic expression, the construct should contain at a minimum a eukaryotic promoter operably linked to RASSL-encoding DNA, which is in turn operably linked to a polyadenylation sequence. The polyadenylation signal sequence may be selected from any of a variety of polyadenylation signal sequences known in the art. Preferably, the polyadenylation signal sequence is the SV40 early polyadenylation signal sequence. The construct may also include one or more introns, which can increase levels of expression of the RASSL-encoding DNA. Any of a variety of introns known in the art may be used. Preferably, the intron is the human β-globin intron and inserted in the construct at a position 5' to the RASSL-encoding DNA.

Transformation

Any method of transformation can be used to obtain transformed cells containing RASSL-encoding nucleic acid and/or expressing a RASSL of the invention. Thus, the RASSLs of the invention and methods of the invention using RASSLs can be used in combination with any number of vectors or gene delivery systems. In general, methods for transforming and obtaining expression of exogenous DNA or RNA sequences in a mammalian cell are well known in the art (see, for example, Kormal et al., 1987, *Proc. Natl. Acad. Sci. USA,* 84:2150–2154; Sambrook et al. *Molecular Cloning: A Laboratory Manual,* 2nd Ed., 1989, Cold Spring Harbor Laboratory Press, Cold Spring Harbor, N.Y.; each of which are hereby incorporated by reference with respect to methods and compositions for eukaryotic expression of an exogenous nucleic acid sequence). The method selected will generally vary with whether target cell transformation is accomplished in an in vitro cell culture, by administering the RASSL-encoding DNA directly to the mammalian host (in vivo gene therapy), or by introduction of nucleic acid into to target cells in vitro and subsequent transplantation of the transformed cells into a mammalian host (ex vivo gene therapy). The following illustrations are examples of various formulations that can be used to obtain transformed target cells expressing a RASSL of the invention and are not meant to be limiting.

RASSL-encoding DNA can be delivered to the target cells in a variety of different formulations. For example, purified DNA, in a viral vector (e.g., adenovirus, retrovirus), a DNA- or RNA-liposome complex, or by utilizing cell-mediated gene transfer. DNA- or RNA-liposome complex formulations suitable for transformation of the target cells comprise a mixture of lipids that bind to genetic material (DNA or RNA), providing a hydrophobic coat which allows the genetic material to be delivered into cells (see, e.g., Felgner et al., 1987, *Proc. Natl. Acad. Sci. U.S.A.* 84:7413–7417). Exemplary liposome formulations suitable for use in target cell transformation include DOPE (dioleyl phosphatidyl ethanol amine), CUDMEDA (N-(5-cholestrum-3-β-ol 3-urethanyl)-N',N'-dimethylethylene diamine).

Alternatively, the RASSL-encoding nucleic acid can be administered as a DNA or RNA sequence-containing chemical formulation coupled to a carrier molecule which facilitates delivery to the host cell. Such carrier molecules can include, for example, an antibody specific to an antigen expressed on the surface of the target cells, or some other molecule capable of interaction with a receptor associated with the target cells. Such formulations that target a specific cell type for delivery of RASSL-encoding nucleic acid are particularly useful in in vivo transformation.

The form of the DNA preparation for transformation of the target cells will depend upon several factors such as the cell type targeted for gene transfer, the route of administration (e.g., in gene therapy), and whether a biological or nonbiological transforming formulation of nucleic acid (e.g., viral or chemical) is used.

In Vivo and Ex Vivo Gene Therapy

The RASSLs, RASSL-expressing cells, and methods of the invention may be used in combination with any gene therapy method or gene delivery protocol. However, the use of RASSLs is largely independent of the method of gene transfer into the cell. Because RASSLs can be designed to selectively induce proliferation in RASSL-expressing target cells, transformation of one cell with RASSL-encoding DNA, preferably at least 5 cells to 10 cells, more preferably 100 to 1,000 cells, would be sufficient since the proliferative effect could be exploited to expand the cells in vivo to achieve a desired therapeutic effect. Current gene delivery (gene insertion) techniques can stably introduce a gene into cells at an efficiency rate of approximately 1 in 100,000 to 1 in 100 cells. The RASSLs of the invention can be used alone or in combination (e.g., a proliferation-inducing RASSL coexpressed with a RASSL that induces some other desired effect). RASSL-encoding DNA can also be delivered in conjunction with DNA encoding a therapeutic polypeptide of interest to provide for selective expansion of such therapeutic protein-expressing cells (e.g., in vitro for delivery via ex vivo gene therapy or via in vivo gene therapy). The following illustrations are examples of various methods to achieve in vivo gene therapy using RASSL-encoding nucleic acid and the methods of RASSL-mediated, targeted cellular activation of the invention, and are not meant to be limiting.

In Vivo Gene Therapy

In general, in vivo transformation of target cells is accomplished by either mechanical means (e.g., direct injection of a RASSL-encoding nucleic acid formulation near or into the tissue containing the target cells (Fynan et al., 1993, *Proc. Natl. Acad. Sci. USA* 90:11478–11482; Yang et al., 1990, *Proc. Natl. Acad. Sci. USA*. 87:1568–9572; Wolff, et al., 1990, *Science* 247:1465–1468)), or by biological means (e.g., infection of tissue containing the target cells with a nonpathogenic virus, preferably a nonreplicative virus, containing RASSL-encoding DNA). A review of the various techniques available for human gene therapy has been recently reviewed (see Morsy, et al., 1993, *JAMA* 270(19): 2338–2345; Orkin, et al., 1995, "Report and Recommendations of the Panel to Assess the NIH Investment in Research on Gene Therapy," at the following site on the world wide web:

nih.gov/news/panelrep.htm1/.

In vivo gene transfer can be accomplished by administering a RASSL-encoding DNA formulation to the mammalian host either orally or by injection depending upon the site of the cells to be targeted for gene transfer and the formulation of the RASSL-encoding nucleic acid. Where RASSL-encoding nucleic acid is administered by injection, the nucleic acid may be administered to the mammalian host either locally or systemically. Systemic administration can be carried out by, for example, intramuscular injection of a viral vector containing the RASSL-encoding DNA. The amount of DNA and/or the number of infectious viral particles effective to infect and transform a sufficient number of target cells (e.g., a number of cells sufficient to allow for subsequent targeted activation) can be readily determined based upon such factors as the efficiency of in vitro transformation, and the susceptibility of the targeted cells to transformation.

The amount of DNA administered will vary greatly according to a number of factors including the susceptibility of the target cells to transformation, and the size and weight of the host. Generally, the amounts of DNA for human gene therapy can be extrapolated from the amounts of DNA effective for gene therapy in an animal model. For example, the amount of DNA for gene therapy in a human is roughly 100 times the amount of DNA effective in gene therapy in a rat. The amount of DNA necessary to accomplish target cell transformation will decrease with an increase in the efficiency of the transformation method used.

Ex Vivo Gene Therapy

In general, ex vivo gene therapy is accomplished by obtaining target cells from the mammalian host to be treated (e.g., biopsy of tissue containing the target cells, isolation of a desired target cell from circulating lymphocytes and other immune cells) and establishing a primary culture of these target cells according to methods well known in the art. Alternatively, a cell line heterologous to the tissue in which the target cells are to be implanted can be cultured and transformed with RASSL-encoding DNA in vitro. For example, microglia can be cultured in vitro, transformed with RASSL-encoding DNA (where the RASSL provides for enhanced secretion) and DNA encoding a therapeutic protein of interest, and implanted in the mammalian host. Upon activation with RASSL-binding small molecule ligand, the transformed, RASSL-expressing microglia secretes the therapeutic protein from secretory granules. Use of microglia for expression of exogenous nucleic acid, and transplantation of these cells, is well known in the art (Cunningham et al., 1994, *Brain Res.* 658:219–231).

In a preferred embodiment, transformed target cells expressing the RASSL-encoding DNA are selected using the targeted activation method of the invention. Briefly, the transformed cells are exposed to an appropriate synthetic small molecule that binds the RASSL. Upon RASSL binding of the synthetic small molecule, transformed cells expressing the RASSL are activated, and activated cells are selected from the non-RASSL-expressing, nonactivated cells in the population. For example, where the cellular response associated with binding of the synthetic small molecule to the RASSL is cellular proliferation, cells expressing the RASSL are selected by virtue of their selective growth relative to those cells that do not express or properly express the RASSL. Continued culture and exposure of the transformed cells to the synthetic small molecule will result in the expansion of the RASSL-expressing cells to provide a cell population primarily composed of RASSL-expressing target cells. This method of selection of RASSL-expressing target cells avoids exposure of the target cells to any substances that may be toxic or otherwise undesirably present in a cell population that is to be used in therapy in a mammalian host, e.g., implanted in a mammalian host to provide expression of a desired cellular product.

Transgenic Animals Expressing a RASSL of the Invention: Reversible Disease Models and Means of Improved Productivity The methods and compositions of the invention are also useful in generating transgenic reversible disease models. In one embodiment, the transgenic, nonhuman animals express a selected RASSL that, upon binding of a synthetic small molecule ligand, elicits a cellular, G protein-coupled physiological response associated with a disease or condition. However, in the absence of the synthetic small molecule ligand, the RASSL-expressing transgenic animal preferably appears substantially normal, and does not exhibit symptoms of the RASSL-induced condition to a significant extent. Transgenic animals expressing RASSLs are advantageous in that the health and reproductive capacity of the animals are not significantly affected, since the animals exhibit pathology only when the RASSL is stimulated.

For example, RASSL-expressing transgenic animals are useful as models of cardiac arrhythmia. Electrical conduction by heart pace maker cells is mediated by $G_i$ protein signaling. A RASSL is expressed in all or a portion of the transgenic animal's heart pacemaker cells so that, upon exposure to the appropriate synthetic small molecule ligand, $G_i$ signaling is altered. RASSL activation thus provides a means to cause asynchronous conduction in the transgenic animal's heart (e.g., the conduction signal in the RASSL-expressing cells is continuously or erratically activated relative to the conduction of the signal in normal, non-RASSL-expressing cells). The asynchronous conduction by the nontarget and target (RASSL-expressing) cells results in cardiac arrhythmia in the transgenic animal. The efficacy of candidate drugs for treatment of cardiac arrhythmia can be tested in the transgenic cardiac arrhythmia model. Because KOR interacts with the $G_i$ protein family, RASSLs derived from KOR are suitable for use in this reversible cardiac arrhythmia disease model. RASSLs derived from other receptors that interact with other G proteins may also have pathological effects on the heart.

Transgenic, RASSL-expressing animals are also useful in generating models of brain seizures. Electrical short circuits in brain cells (neurotransmission) are associated with G protein activity. Thus, similar to the cardiac arrhythmia model discussed above, brain cells expressing RASSLs are induced by small molecule binding to conduct an "asynchronous" electrical signal, resulting in a brain seizure in the transgenic animal. The efficacy of drug candidates for the prevention or control of seizures could then be tested in this animal model.

RASSL-expressing transgenic animals are also useful models of dementia or neurodegenerative diseases. Abnormal G protein signaling has been correlated with various dementias including Alzheimer's disease. Therefore, RASSL expression and activation could be used to mimic some aspects of dementia, which in turn could be used as an animal model for testing compounds for treatment of dementia and symptoms associated therewith.

RASSL-expressing transgenic animals are also useful as models of osteoporosis. G protein signaling is involved in regulating the activity of osteoclasts and osteoblasts; PTH and calcitonin (the two major calcium regulating hormones) are both G protein-coupled receptors. Transgenic models of osteoporosis are generated by, for example, expressing a RASSL in the animal's osteoclasts and/or osteoblasts. Preferably, the RASSL does not bind the natural ligand of the native PTH or calcitonin receptor, but is activated by exposure to a synthetic small molecule. The activation of the RASSL would override the native PTH, or calcitonin, causing abnormal bone metabolism.

RASSL-expressing transgenic animals are also useful in the study of vasospasm, the phenomenon associated with stroke, migraine, cardiac ischemia, dementia and peripheral vessel vasospasm. Smooth muscle contraction in vessels, which is associated with these various types of vasospasm-induced phenomena, is activated by $G_q$ protein activation. RASSL-mediated stimulation of contraction in, for example, vessels of the brain is thus useful in mimicking stroke or migraines in the transgenic animal model. Further, RASSL-mediated stimulation of contraction of muscle cells in peripheral limbs is useful in mimicking Raynaud Syndrome. RASSL-mediated smooth muscle contraction is also useful in mimicking cardiac vasospasm by induction of contraction of smooth muscle of the heart by RASSL binding of synthetic small molecule. Because serotonin receptors are $G_q$-coupled, RASSLs derived from serotonin receptors are preferred RASSLs for use in transgenic animal models of disease or conditions associated with vasospasm.

The compositions and method of the invention are also useful in generating transgenic animal models having a reversible immune dysfunction. G protein signaling is involved in homing, chemotaxis, and/or activation of leukocytes and is thus implicated in the development of a variety of immune disorders. For example, a transgenic mouse having an inactivated $G_{i\alpha}$ protein develops a Crohn's disease-like syndrome. RASSL expression in leukocytes is thus useful in mimicking hyper- or hypo-immune functions associated with arthritis, Lupus, Crohn's disease, and other autoimmune disorders. Such animal models are useful in, for example, screening candidate drugs for the alleviation or amelioration of symptoms associated with these diseases.

RASSL-expressing transgenic animals can also be used to increase their usefulness or productivity in food production. Calcium metabolism is regulated by G protein-coupled receptors, and thus can be regulated by RASSLs. Calcium content of food is important for the nutritional value as well as the preservation of food. For example, the egg shell is primarily made of calcium. RASSL stimulation could be used to increase the calcium in an egg shell by mobilizing calcium stores, thereby increasing the strength of the eggs, and decreasing the loss of eggs due to handling. In another example, G protein-coupled receptors also control the fat and muscle content of meat. RASSLs could be used to adjust the fat and muscle content of animals, which could enhance the nutritional value of the animals.

RASSLs may also be used to regulate many aspects of reproduction that are naturally regulated by G protein coupled receptors. For instance, ovulation and testicular maturity are controlled by the luteinizing hormone receptor (LH-R; a $G_s$-coupled receptor) while uterine contractions and the onset of labor are controlled by the oxytocin receptor (a $G_q$-coupled receptor). RASSLs of the invention may be designed from these receptors to replace or enhance these receptors' functions. Regulation of reproduction is vital to many animal breeding programs (e.g., breeding for food production, transgenic animals, or other scientifically or commercially valuable animals).

For instance, the oxytocin receptor may be replaced with a $G_q$-coupled RASSL to regulate the timing of labor, thereby ensuring that labor occurred at a time that was best for the pregnant animal. For example, if the pregnant animal were ill, the administration of the RASSL agonist would be delayed until the pregnant animal had recovered from the illness. Labor and delivery could also be regulated to ensure that the animal care staff was best prepared to attend to the animal; this is particularly important when dealing with large animals such as sheep, cows, or horses which require a considerable amount of care. Regulation of labor could increase efficiency and lower costs of an animal breeding program.

RASSL-mediated regulation of reproduction may also be used to limit or control distribution of transgenic animals. For instance, a RASSL replacing the LH-R or the oxytocin receptor would allow regulation of reproductive processes such that the animal would only be fertile (LH-R replacement), or go into labor (oxytocin receptor replacement) upon administration of the appropriate RASSL agonist. If the RASSL agonist were a proprietary compound (with limited availability), only companies or individuals with access to the RASSL agonist would be able to breed the animals, thereby allowing a company to sell its transgenic animals without heightened concerns about unauthorized breeding.

RASSL-dependent fertility may also address problems associated with breeding of transgenic animals in the wild, a considerable environmental concern. For instance, hatchery bred salmon released into the wild can breed with wild salmon, thereby diluting the genetic pool of wild salmon. Replacement of the hatchery salmon's G protein coupled receptor(s) with RASSLs of the invention may aid in fish breeding and decrease the possibility of the hatchery salmon breeding with wild salmon, since the hatchery salmon would be fertile (e.g., due to ovulation or sperm production) when the appropriate RASSL is stimulated. In addition, the timing of fertility and egg laying of the RASSL-regulated fish may increase the productivity of the fish hatchery by, for example, inducing egg laying only under ideal conditions. Similar scenarios may be applied to any animals that are uses commercially or scientifically and could mix with the wild populations of animals (e.g., chickens, sheep, cows, horses, rabbits, rodents, shrimp, bees, and the like).

Transgenic animals can be generated according to a variety of methods well known in the art. In general, transgenic animals are generated by introducing the desired nucleic acid (e.g., RASSL-encoding nucleic acid and/or nucleic acid encoding a therapeutic cellular product) into the germline DNA of a host animal. Introduction of the desired nucleic acid into the germline DNA of the host animal can be accomplished by a variety of methods. For example, introduction of the desired nucleic acid into the animal's germline DNA can be accomplished by microinjection into a fertilized egg of the host animal, followed by transfer of viable eggs into the oviducts of the pseudopregnant mice (see, e.g., Gordon et al., 1980, *Proc. Natl. Acad. Sci.* 77:7380–7384, herein specifically incorporated by reference for methods of genetically transforming embryos by microinjection of DNA; and Hogan et al., 1986, *Manipulation of the Mouse Embryo: A Laboratory Manual,* Cold Spring Harbor Laboratory, NY, herein specifically incorporated by reference for methods of generating transgenic animals). Alternatively, the embryonic transduction can be accomplished with a retroviral vector containing the desired transgene.

Alternatively, the constructs containing the desired transgene can be introduced into embryonic stem (ES) cells obtained from preimplantation embryos cultured in vitro (U.S. Pat. No. 5,464,764; Evans et al., 1981, *Nature* 292:154–156; Bradley et al., 1984, *Nature* 309:255–258; Gossler et al., 1986, *Proc. Natl. Acad. Sci.* 83:9065–9069; Robertson et al., 1986, *Nature* 322:445–448). An appropriate vector containing the desired construct can be introduced into the ES cells by methods known in the art, including electroporation or microinjection. Transformed ES cells are combined with blastocysts from a nonhuman animal. The transformed ES cells thereafter colonize the embryo, contributing to the germ line of the resulting transgenic animal. For a review, see, Jaenisch, 1988, *Science* 240:1468–1474, herein specifically incorporated by reference.

Administration of Small Molecule Ligands to Induce In Vivo RASSL-mediated Targeted Cellular Activation Once the RASSL-expressing target cell(s) are present within the mammalian host, activation of these target cells is induced by administration of a synthetic small molecule(s) (also referred to herein as drug(s)) that can bind the RASSL and facilitate G protein activation and activation of the desired cellular response (e.g., proliferation and/or secretion). The route of administration and amount of the drug will vary with a variety of factors such as the condition to be treated (e.g., in gene therapy), the location of the RASSL-expressing cells within the host to be treated (e.g., within brain tissue, liver tissue, lung tissue, etc.), various patient-dependent or host-dependent (e.g., transgenic animal) factors (e.g., size, weight, age, health, disease severity, responsiveness to therapy, responsiveness to administration of the small molecule ligand, etc.), and various drug-dependent factors (e.g., oral availability, molecular weight, toxicity, RASSL-specific affinity, etc.) Where the synthetic small molecule drug has been previously developed for activation of a native G protein-coupled receptor, guidance for dosages and routes of administration can be found in the *Physician's Desk Reference* (1995, 49th Ed., Arky et al., eds., Medical Economics Data Production Company, Montvale, N.J.).

In general, despite any guidance available for administration of the small molecule ligand, the appropriate route of administration and dosage are generally determined on a case-by-case basis by the attending physician. Such determinations are routine to one of ordinary skill in the art (see, for example, *Remington's Pharmaceutical Sciences,* 18th Ed., 1990, Gennaro et al., eds., Mack Publishing Co., Easton, Pa.). Synthetic small molecule drugs of particular interest are those that can be safely and effectively administered orally or by transdermal delivery by injection (e.g., parenteral injection including subcutaneous, intramuscular, and intravenous injection), but preferably by oral administration.

The specific dosage appropriate for administration is readily determined by one of ordinary skill in the art according to the factors discussed above (see, for example, *Remington's Pharmaceutical Sciences,* supra). In addition, the estimates for appropriate dosages in humans may be extrapolated from determinations of synthetic small molecule required to activate RASSL-expressing target cells in vitro and/or in animal studies (e.g., in a transgenic animal having a RASSL-expressing target cell population). For example, appropriate dosages of KOR-binding drugs for an average 70 kg human range from about 10–50 mg, up to about 600 mg or more per day. For example, pentazocine dosages recommended in the Physician's Desk Reference (supra) are about 50 mg every 3 hrs, up to 600 mg per day or more.

The appropriate formulation of the synthetic small molecule will vary with a variety of factors including the drug used and the route of administration. For example, where the small molecule drug is injected intravenously, the drug is generally formulated in a 0.15 M saline solution containing a desired concentration of drug. Guidance for specific drug formulations can be found in the Physician's Desk Reference, supra, as well as in the literature supplied by the manufacturer.

Assessment of Efficacy of RASSL-mediated Targeted Cellular Activation

The effects of RASSL-mediated, targeted cellular activation can be assessed in various ways. The means of assessing targeted cellular activation will vary with the cell type targeted, the therapeutic goal of targeted cell activation, and the disease or condition to be treated. For example, where the therapeutic goal of targeted cell activation is to increase the overall amount of a protein or other molecule expressed by the target cell (e.g., a natural secretion product of the target cell or a protein or other molecule expressed by the target cell from a heterologous sequence introduced by transformation), the effects of targeted cell activation can be assessed by measuring levels of the protein or other molecule present in the mammalian host (e.g., in the bloodstream, saliva, or other bodily fluid of the host). Such assays can be performed either qualitatively or quantitatively. The ELISA assay, as well as other immunological assays for detecting a protein in a sample, are described in *Antibodies: A Laboratory Manual* (1988, Harlow and Lane, eds., Cold Spring Harbor Laboratory, Cold Spring Harbor, N.Y.).

Alternatively, or in addition, the efficacy of RASSL-mediated targeted cell activation can be assessed by testing for the level of an activity associated with the therapeutic protein (e.g., an enzymatic activity). Furthermore, the efficacy of RASSL-mediated targeted cell activation can be assessed by monitoring the condition of the mammalian host for improvement. For example, where the therapeutic proteins are blood clotting factors, the subject's blood is examined for blood clotting activity or other parameters associated with hemophilia. Where the RASSLs are expressed in a transgenic, nonhuman animal to provide a reversible disease model, the physiology of the animal RASSL-activation is monitored by the production in the animal of symptoms of the disease or condition to be simulated (e.g., cardiac arrhythmia, osteoporosis, seizures, vasospasm, or alterations in fat or calcium metabolism).

Utilities

The composition and method of the invention are useful in a variety of in vitro and in vivo applications. Targeted, RASSL-mediated cellular activation is useful in various in vitro and in vivo applications in cell selection and culture. For example, the targeted cellular activation method of the invention is useful in the selective amplification of a RASSL-expressing cell line of interest. Cells to be cultured in vitro and subsequently implanted into a mammalian host can be transformed with DNA encoding a RASSL that facilitates cellular proliferation. Proliferation of the RASSL-expressing, transformed cells is induced by exposure to the appropriate synthetic small molecule ligand, thereby facilitating controlled, efficient amplification of the cell line of interest. Cells amplified in this manner may then be implanted into the mammalian host. Use of the RASSL-mediated, targeted cellular proliferation method of the invention allows for selective expansion of a selected cell line in a shorter period of time, and without the use of a selective agent (e.g., antibiotics, methotrexate, metallothionein) which may be undesirable for use in selection of cells for subsequent implantation into a mammalian host (e.g., human, murine, bovine, equine, etc.) Furthermore, since a RASSL is less responsive to a selected endogenous ligand than the native receptor, using a RASSL would pose less risk than using a native receptor for the same purpose.

The compositions and method of the invention are also useful in facilitating growth and selectively expanding a desired cell type in a primary cell culture in vitro. For example, an in vitro culture of rare or difficult to culture cells can be transformed with RASSL-encoding DNA, thus allowing enhancement of cell culture growth by exposing the cells to the appropriate synthetic small molecule ligand. FIG. 2 schematically illustrates expansion of RASSL-expressing target cells (i.e., by RASSL-mediated triggering of a G protein-mediated proliferative cellular response), relative to proliferation in nature. Thus, the method of the invention is useful in promoting target cell growth at a rate faster than growth of nontarget cells, thereby enriching for target cells in a mixed cell population.

The RASSL-mediated, targeted cellular activation method of the invention is also useful in regulation of secretion by an in vitro culture of secretory cells. For example, secretory cells of interest are transformed with DNA encoding a RASSL associated with induction of the secretory response. Upon exposure to the appropriate small molecule ligand, the transformed secretory cells are induced to secrete the cellular product of interest. Thus, the method of the invention allows for increased and/or regulated secretion by such cultured cell lines.

RASSLs are also useful in the production of transgenic, nonhuman animals that can serve as reversible disease models. RASSL activation can confer a new biological, cellular response upon administration of the agonist synthetic small molecule ligand to the transgenic animal (e.g., change of heart rate or biochemical changes).

The method of the invention using RASSL-mediated targeted cellular activation can be used to overcome the present limitations of in vitro transformation efficiency, primary cell isolation and culture, gene therapy efforts, and various other settings in which it is desirable to amplify the number of eukaryotic cells present in a cell population.

The method of the invention is additionally useful in providing a method to administer a controlled amount of a therapeutic cellular product to a mammalian subject. RASSL-encoding DNA is used to transform cells of an in vivo implant designed to provide a reservoir of cells that secrete a desired protein or other molecule for therapeutic purposes. Secretion of the therapeutic product of such RASSL-expressing cellular implants can be amplified by exposure of the cellular implant to the synthetic small molecule that activates the RASSL.

Figure 5:
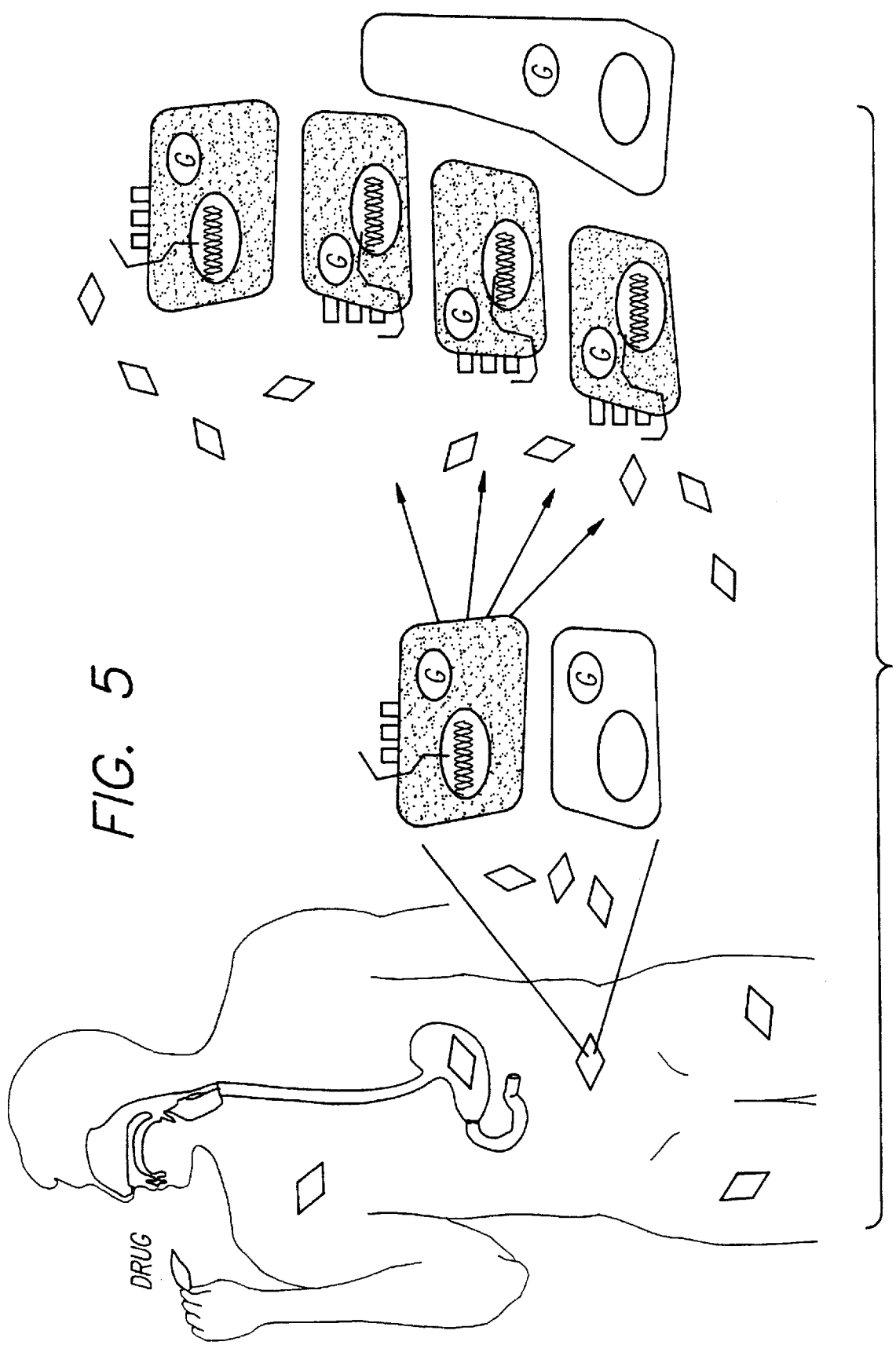
FIG. 5 is a schematic illustrating RASSL-mediated targeted cellular proliferation in vivo.

Furthermore, targeted cellular activation is useful in combination with in vivo or ex vivo gene therapy. RASSL-encoding nucleic acid is cotransfected with a DNA of interest encoding a gene product to be delivered by gene therapy. The DNA of interest may encode any cellular product desirable for delivery to the mammalian host (e.g., secreted into the host's blood stream or into the host's gastrointestinal tract). For example, the mammalian host may have a disease or condition that is amenable to treatment by expression or over-expression of a protein which is either normally present in a healthy mammalian subject or is foreign to the mammalian host (e.g., a protein having an antibiotic activity, or a protein that is absent or defective in the mammalian host (e.g., protein replacement therapy)). Administration of the appropriate synthetic small molecule activates the RASSL-expressing target cells (e.g., by inducing a proliferative response in the target cells) thereby increasing the number of transformed cells expressing the RASSL and the therapeutic DNA of interest (FIG. 5).

Thus, where the targeted cellular activation method of the invention results in targeted proliferation of RASSL-expressing cells, the acceptable transformation efficiency for gene therapy is lowered, since transformed cells can be selectively amplified to provide a therapeutically effective dosage of the gene therapy product. Likewise, where the targeted cellular activation method of the invention results in increased cellular secretion, the acceptable level of transformation efficiency for gene therapy is likewise lowered, since fewer transformed cells can provide a higher level of secretion of the therapeutic product of interest. Once the clinical effect is achieved (e.g., a desired dosage of therapeutic cellular product is delivered to the subject), the drug is removed to prevent unwanted proliferation or secretion.

Exemplary applications of the targeted activation method (e.g., by proliferation or secretion) of the invention are provided in Table 3.

TABLE 3

Exemplary Applications of Targeted Proliferation in Gene Therapy

| Tissues for targeted activation | Therapeutic gene product | Disease target |
|---|---|---|
| Liver cells | LDL-receptor | Atherosclerosis |
|  | Lipoproteins | Atherosclerosis |
|  | Blood clotting factors | Hemophilia |
| Cells of | ApoE to vascular wall | Atherosclerosis |
| Hematopoietic | Hirudin/antithrombotics | Atherosclerosis |
| Lineage | ApoE/growth factors to brain | Alzheimer's |
| Macrophages |  |  |
| T cells | Dominate negative HIV proteins | AIDS |
| B cells | Deficient genes in SCID | Immune deficiencies |

RASSL-mediated, targeted activation is also useful in facilitating and regulating delivery of therapeutic, bioactive proteins in the brain or any other part of the body where it is advantageous to gain pharmacological control of a population of cells. The delivery of bioactive proteins to the brain by conventional methods has proven difficult since the blood-brain barrier blocks the entry of most peripherally administered therapeutic proteins (e.g., therapeutic proteins administered orally or by intravenous injection). Since many synthetic small molecules are small enough and of appropriate ionic charge to cross the blood-brain barrier, the RASSL-mediated targeted activation method of the invention overcomes this problem.

For example, the targeted activation method of the invention is useful in facilitating intracranial delivery of nerve growth factor (NGF), which is currently proposed for administration to Alzheimer's patients in clinical trials by direct intracranial injection. First, a cell line that secretes NGF or that can he engineered to secrete NGF (e.g., adrenal chromaffin cells, myoblasts, myotubes, fibroblasts) is transformed with RASSL-encoding nucleic acid to provide a RASSL-expressing, NGF-secreting target cell. For example, glial cells, which package and secrete foreign proteins from secretory granules, can be transformed with NGF-encoding DNA and RASSL-encoding DNA (Tuszynski et al., 1994, Experim. Neurol. 126:1–14; Cunningham et al., 1994, Brain Res. 658:219–231). A reservoir of RASSL-expressing, NGF-secreting target cells are transplanted in the brain.

When increased NGF secretion is desired, the patient simply takes an oral or intravenous dose of the appropriate synthetic small molecule, which subsequently crosses the blood-brain barrier, binds the RASSLs and activates NGF secretion and/or target cell growth. This system provides a simple method for stimulation, as well as regulation, of secretion of protein in the brain. Delivery of growth factors such as NGF by the method of the invention can similarly be used to treat various other neurological disorders including, but not limited to, Parkinson's disease and amyotropic lateral sclerosis (ALS, also known as Lou Gehrig's disease).

The method of the invention further provides a method for regulated release (e.g., timed release) growth factor secretion. Because many growth factors have natural diurnal rhythms, it thus may be preferable to trigger growth factor secretion while the subject is asleep. For example, a patient having a RASSL-expressing, NGF-secreting target cell implant simply takes a dose of the RASSL agonist before bedtime. The small molecule agonist crosses the blood-brain barrier and facilitates increased NGF secretion while the patient sleeps. By morning the drug is metabolized, resulting in decreased RASSL activation and decreased secretion of NGF.

Similarly, the method of the invention can be used to treat and/or prevent development of Alzheimer's disease by delivery of specific isoforms of ApoE to the patient's brain Patients who are homozygous for the ApoE e4 allele (which accounts for about 2% of the U.S. population) are at an 85% risk of developing Alzheimer's disease. Patients who are at risk of developing Alzheimer's disease, or who have already developed Alzheimer's symptoms, can be treated by delivery of the ApoE isoforms (e.g., e2 or e3) that are not associated with Alzheimer's disease. RASSL-encoding nucleic acid and ApoE e2- or e3-encoding nucleic acid is used to transform microglia cells of the brain either in vivo or ex vivo. Alternatively, cells heterologous to the brain may be transformed in vitro with the RASSL-encoding and ApoE e2- or e3-encoding nucleic acid, cultured in vitro and subsequently used in a cellular implant that expresses the RASSL and the desired ApoE isoform. Alternatively, because microglia are of hematopoietic origin, stem cells of the patient can be transformed with the RASSL-encoding and ApoE e2- or e3-encoding nucleic acid using either in vivo or ex vivo gene therapy techniques. Since $G_i$ and $G_q$ signals are implicated in proliferative response of hematopoietic cells, the RASSL used in to facilitate microglial proliferation can be derived from either the native KOR or native serotonin receptors, respectively.

Once the RASSL-expressing, ApoE e2- or e3-expressing cells are in place in the patient's brain, proliferation (and thus production of ApoE e2 or e3) can be induced by administration of the appropriate synthetic small molecule drug to the patient. Expression of the desired ApoE isoform, and the balance of ApoE e4 and ApoE e2 or e3 in the patient, can be monitored by examining the patient's central spinal fluid (CSF) for the presence of these proteins using methods known in the art. The presence of the e2 or e3 isoform in an amount greater than that of the e4 isoform is indicative of treatment and/or prevention of Alzheimer's disease.

EXAMPLES

The following examples are put forth so as to provide those of ordinary skill in the art with a complete disclosure and description of how to carry out the invention and is not intended to limit the scope of what the inventors regard as their invention. Efforts have been made to ensure accuracy with respect to numbers used (e.g., amounts, temperatures, etc.), but some experimental error and deviation should be accounted for. Unless indicated otherwise, parts are parts by weight, molecular weight is weight average molecular weight, temperature is in degrees Centigrade, and pressure is at or near atmospheric.

Example 1

Generation and Characterization of Kappa Opioid Receptor (KOR) RASSLs: OR1

The general strategy for making a RASSL based on a G protein-coupled receptor that binds a peptide ligand is to mutate the extracellular loops of the receptor. The extracellular loops are the putative binding sites of peptide ligands (but not small molecule ligands). The extracellular loops can be identified for any G protein-coupled receptor by locating the transmembrane region. The mutations can be chosen by substitution residues from related receptors, or by insertion of randomly chosen residues (e.g., saturation mutagenesis).

To ease the detection of the recombinant RASSL the N-terminus of this modified RASSL with the epitope for the FLAG monoclonal antibody (commercially available from Kodak-IBI, New Haven Conn.). This epitope does not affect binding or signaling by agonist drugs. The FLAG epitope allows for immunological detection by western blotting, immunohistochemistry, and FACS sorting. In addition, the RASSL-encoding sequence can include a sequence encoding an epitope (YPYDVPDYA SEQ ID NO:12) for the anti-HA monoclonal antibody (referred to hereafter as the HA tag; Boehringer Mannheim) for ease in detection and purification of the product. The RASSL-encoding sequence may also include a Prolactin signal sequence to facilitate post-translational processing and delivery to the cell surface.

The amino acid (SEQ ID NO:2) and nucleotide (SEQ ID NO:1) sequences of human KOR are provided in the sequence listing below. The nucleotide sequence (SEQ ID NO:3) of wild-type human KOR having an N-terminal Prolactin signal sequence (nucleotides 1–90; lower case letters), a FLAG epitope tag (nucleotides 91–114; lower case letters), and an HA tag (nucleotides 1252–1284; lower case letters) is shown in FIGS. 7A and 7B.

A RASSL derived from the human kappa opioid receptor (KOR) was generated by mutation of specific KOR codons encoding selected amino acids of the extracellular loops. Briefly, cDNA encoding human KOR was inserted into a mammalian expression vector. The amino acid and nucleotide sequences of both the human KOR and DOR (delta opioid receptor) are known (see Zhu et al., 1995, *Life Sci.* 56: 201–207 (KOR sequence); Evans et al., 1992, *Science* 258:1952–1955; Kieffer et al., 1992, *Proc. Natl. Acad. Sci. USA* 89:12048–12052 (cloning and sequence of DOR)). The specific amino acids associated with each structural domain are shown in Table 4 (from SWISS-PROT):

TABLE 4

Structural Domains of KOR

| Domain | Amino Acid Residue | Position | |
|---|---|---|---|
| N-Terminus | 1 | 58 | EXTRACELLULAR |
| TMH1 | 59 | 85 | TRANSMEMBRANE |
| i1 | 86 | 95 | CYTOPLASMIC |
| TMH2 | 96 | 117 | TRANSMEMBRANE |
| e1 | 118 | 132 | EXTRACELLULAR |
| TMH3 | 133 | 154 | TRANSMEMBRANE |
| i2 | 155 | 173 | CYTOPLASMIC |
| TMH4 | 174 | 196 | TRANSMEMBRANE |
| e2 | 197 | 222 | EXTRACELLULAR |
| TMH5 | 223 | 247 | TRANSMEMBRANE |
| i3 | 248 | 275 | CYTOPLASMIC |
| TMH6 | 276 | 299 | TRANSMEMBRANE |
| e3 | 300 | 311 | EXTRACELLULAR |
| TMH7 | 312 | 333 | TRANSMEMBRANE |
| C-Terminus | 334 | 380 | CYTOPLASMIC |
| Disulfide bond | 131 | 210 | |
| LIPID | 345 | 345 | PALMITATE |
| CARBOHYDRATE | 25 | 25 | POTENTIAL |
| CARBOHYDRATE | 39 | 39 | POTENTIAL |

Figure 6:
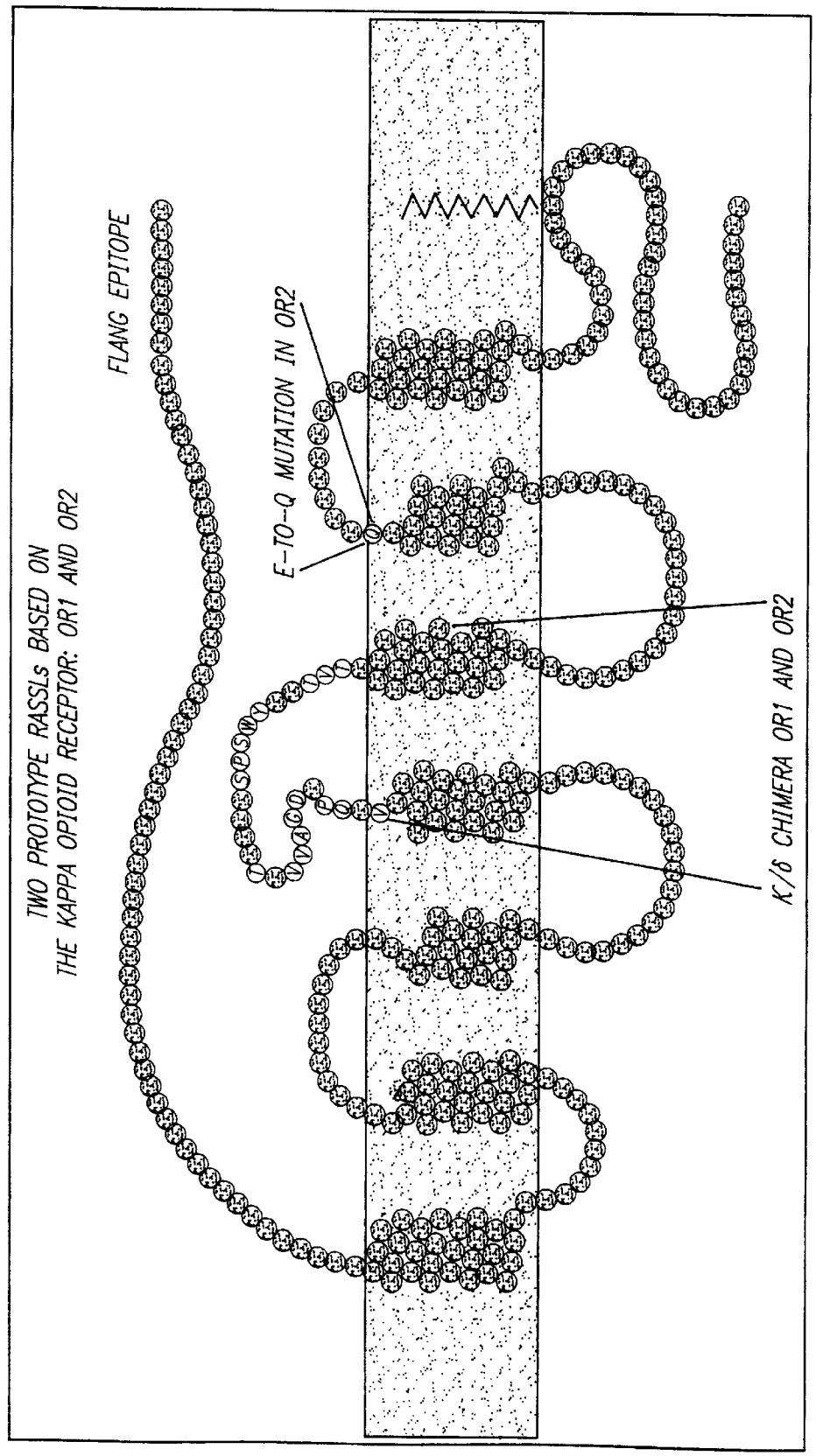
FIG. 6 is a schematic showing the two-dimensional structure of, and specific amino acid alterations in, a RASSL derived from the kappa opioid receptor.

A site-specific human KOR mutant, termed OR1, was generated by site-specific mutation of the human KOR receptor sequence to generate a human KOR mutant nucleotide sequence having 17 specific amino acid substitutions. Each of the amino acids changed in the human OR1 mutant were changed to the amino acid residue at the corresponding position in the DOR amino acid sequence. FIG. 6 is a schematic of this human KOR mutant showing the two-dimensional structure, amino acid sequence, and the position of the amino acid changes in OR1. The nucleotide (SEQ ID NO:5) and amino acid sequences (SEQ ID NO:6) of the RASSL OR1 having an N-terminal prolactin signal sequence (nucleotides 1–90; lower case letters), a FLAG epitope tag (nucleotides 91–114; lower case letters), and an HA epitope tag (nucleotides 1243–1275; lower case letters) are shown in FIGS. 8A and 8B. The nucleotide sequence of OR1 corresponding to human KOR sequences (nucleotides 474–701) are in upper case; sequences corresponding to non-human KOR sequences (nucleotides 702–787) are in lower case.

OR1 was expressed in COS-7 and CHO-KI cells, and characterized for dynorphin binding, bremazocine binding, spiradoline binding, and activation of G protein-mediated signals as previously described (Conklin et al., 1993, *Nature* 363:274–276; Wong et al., 1992, *Science* 255;339–342; Federman et al., 1992, *Nature* 354:159–161). The results of the binding experiments and the signaling experiments are summarized in Tables 5 and 6, respectively. Table 7 summarizes the results of these studies. OR1 exhibited a 200-fold decrease in dynorphin binding (Ki=14.6 nM) relative to dynorphin binding by native human KOR (Ki=0.064 nM). In contrast, OR1 exhibited no significant change in bremazocine binding affinity (OR1 Ki=0.064 nM; native human KOR Ki=0.038 nM), and a relatively small change in spiradoline binding (OR1 Ki=6.29; human KOR Ki=1.132). Signaling studies showed that OR1 inhibits adenylyl cyclase (the expected biochemical effect) in response to bremazocine and other small molecule drugs and high concentrations of dynorphin. Thus, OR1 is especially suitable for use as a RASSL in the present invention.

TABLE 5

Binding of Dynorphin, Bremazoaine and Spiradoline to Wild-type KOR, OR1, and OR2

| | Wild-type KOR | | OR1 | | OR2 | |
|---|---|---|---|---|---|---|
| Ligand | Ki (in nM) | Fold decrease* | Ki (in nM) | Fold decrease* | Ki (in nM) | Fold decrease* |
| DynorphinA | 0.064 ± 0.043 | 1 | 14.64 ± 2.99 | 229 | 124.52 ± 19.38 | 1946 |
| Bremazocine | 0.038 ± 0.012 | 1 | 6.29 ± 1.92 | 1.7 | 5.65 ± 1.19 | 1.2 |
| Spiradoline | 1.32 ± 0.38 | 1 | 6.29 ± 1.92 | 4.8 | 5.65 ± 1.19 | 4.3 |

*Fold decrease in binding is relative to binding to wild-type KOR (Ki for wild-type KOR divided by Ki for OR1 or OR2)

TABLE 6

Signaling by Wild-type KOR, OR1, or OR2 in the Presence of Dynorphin A or Bremazocine to Wild-type KOR, OR1, and OR2 ($EC_{50}$ in nM)

| | Wild-type KOR | | OR1 | | OR2 | |
|---|---|---|---|---|---|---|
| Ligand | $EC_{50}$ | Fold decrease* | $EC_{50}$ | Fold decrease* | $EC_{50}$ | Fold decrease* |
| DynorphinA | 0.66 ± 0.62 | 1 | 61.03 ± 20.56 | 92.8 | 1083.73 ± 367.24 | 1648.8 |
| Bremazocine | 0.067 ± 0.05 | 1 | 0.068 ± 0.039 | 1 | 0.34 ± 0.21 | 5.17 |

*Fold decrease in signaling is relative to signal detected with wild-type KOR (for wild-type KOR divided by Ki for OR1 or OR2)

TABLE 6

The RASSLs OR1 and OR2

| | Binding | | Biochemical Signal | | Growth Signal | |
|---|---------|--------|--------------------|------|---------------|------|
| | Peptide | Drug 1 | Peptide | Drug 1 | Peptide | Drug 2 |
| OR1 | ↓200x | NC | ↓95x | NC | | |
| OR2 | ↓2,000x | NC | ↓1,600x | ↓5x | ↓2,000x | NC |

NC = No Change; Peptide = dynorphin; Drug 1 = bremazocine; Drug 2 = spiradoline

Example 2
Generation and Characterization of the Kappa Opioid Receptor (KOR) RASSL OR2

Another RASSL derived from the human kappa opioic receptor (KOR), OR2, was generated in a manner similar to that described in Example 1. OR2 was generated by site-specific mutation of the human KOR receptor sequence to generate a human KOR mutant nucleotide sequence having the same 17 specific amino acid substitutions as in OR1, as well as an glutamic acid-to-glutamine (E-to-Q, see FIG. 6). FIG. 6 provides a schematic of the OR2 RASSL. FIGS. 9A and 9B show the amino acid (SEQ ID NO:8) and DNA sequences (SEQ ID NO:7) of OR2, and indicate the position of the N-terminal prolactin signal sequence (nucleotides 1–90; lowercase), the FLAG tag (nucleotides 91–114), the C-terminal HA taq (nucleotides 1243–1275), the sequences derived from the wild-type human KOR (nucleotides 474–701; upper case), the non-human KOR sequences (nucleotides 702–787; lower case), and the position of the glutamic acid-to-glutamine mutation (nucleotides 987–991).

OR2 was expressed in COS-7 and CHO-KI cells, and characterized for dynorphin binding, bremazocine binding, spiradoline binding, and activation of G protein-mediated signals as described in Example 1. OR2's binding affinity and ability to elicit a biochemical signal upon binding are summarized in Table 5. The binding affinity of OR2 for dynorphin was reduced by 2,000-fold. In contrast, OR2 exhibited no change in bremazocine binding affinity (OR2 Ki=0.046 nM; native human KOR Ki=0.038 nM), and a relatively small change in spiradoline binding (OR2 Ki=5.65; human KOR Ki=1.32). The differing binding affinities of OR2 for dynorphin and bremazocine were reflected in the signaling assays; activation of the biochemical signal required about 1,600 times more dynorphin to have the same effect has compared to dynorphin acting on the wild type KOR.

The small molecule drug bremazocine activated the OR2 receptor with high affinity. However, activation of the biochemical signal required about 5 times more bremazocine compared to the amount required to activate the wild-type KOR. Because OR2 binds and is activated by a small molecule drug (bremazocine) superiorly to a selected natural ligand (dynorphin), OR2 is especially suitable as RASSL for use in the invention.

Example 3
In Vitro Proliferation of Target Cells Expressing the RASSL OR2

Nucleic acid encoding the RASSL derived from the RASSL OR2 was introduced into rat 1a fibroblasts and cultured in vitro. Briefly, the cells were made quiescent (i.e., were synchronized so that all cells wherein a low growth state) by first seeding 5×10$^5$ cells per well of a 24-well plate in Dulbecco's Modified Eagles (DME) medium with 10% calf serum. After incubating for 12–24 hours, the medium was removed, the cells rinsed with serum-free media, and 1 ml of serum-free media. The cells were than incubated for an additional 24 hours. The ability of the OR2 RASSL to facilitate cell proliferation was tested by adding spiradoline (OR2 agonist) or dynorphin (selected natural ligand; negative control) at various amounts. After incubating for 16 hours, 1 microcurie of $^3$H-thymidine (NEN #NET-027Z) (1 µl diluted with 24 µl of media) was added to each well, and the cells incubated for an additional 8 hours.

Cell proliferation was measured by incorporation of the $^3$H-thymidine as previously described (Conklin et al., 1988, Proc. Natl. Acad. Sci. USA 85:8698–8702). Briefly, the $^3$H-thymidine labeled DNA was extracted by first aspirating the media, and washing the cells carefully with 1 ml ice cold PBS. The PBS was aspirated away and 1 ml of ice cold 5% TCA was added. After incubation at 4° C. for 30 minutes, the TCA was aspirated away, the cells washed once with PBS, and 0.5 ml 0.5N NaOH/0.5% SDS was added at room temperature. The samples were then collected and added to scintillation vials for detection of the amount of radiation present in the sample.

Figure 10:
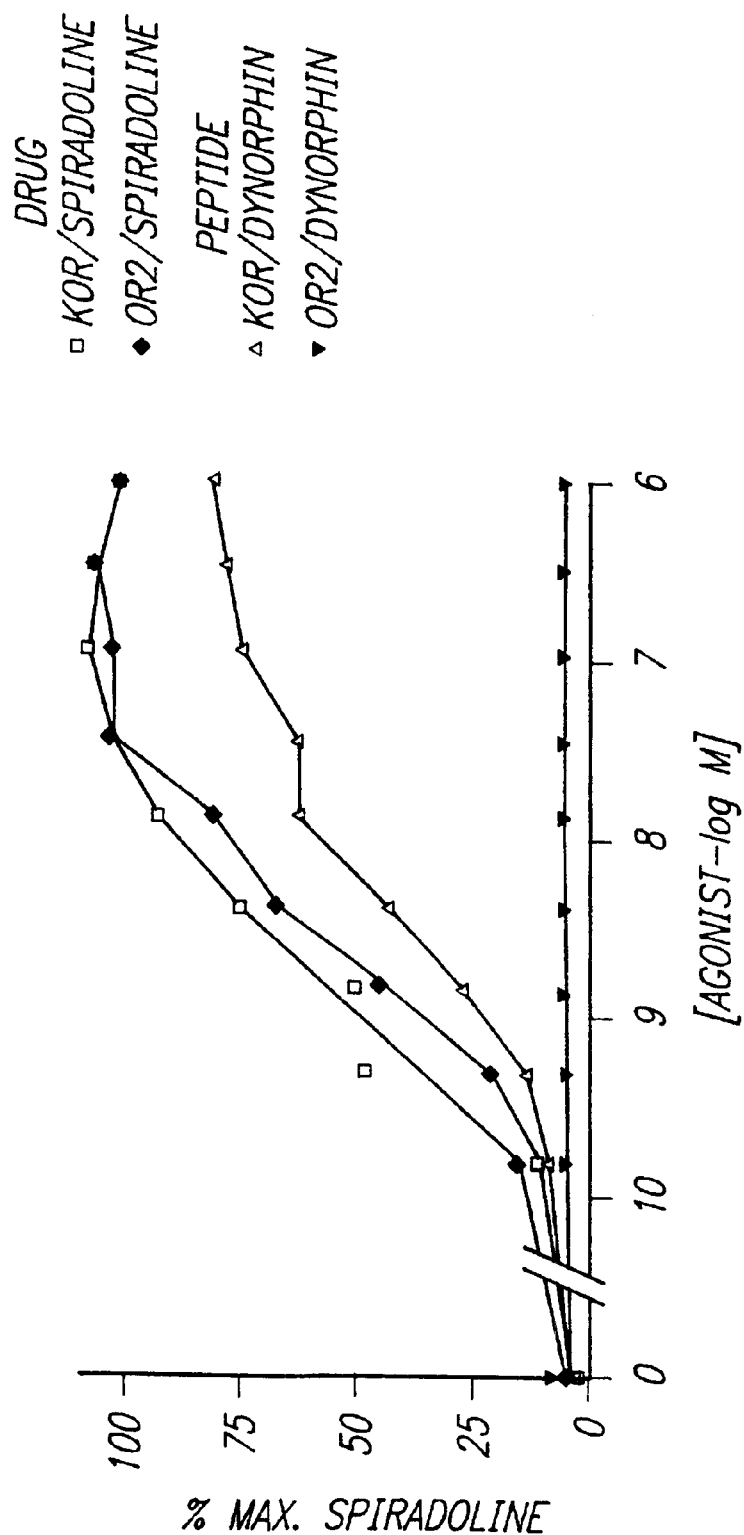
FIG. 10 is a graph showing proliferation of a RASSL-expressing cell in vitro. Open triangles wild-type kappa opioid receptor in the presence of dynorphin; closed triangles, the RASSL OR2 in the presence of dynorphin; open squares, wild-type kappa opioid receptors in the presence of spiradoline; closed squares, the RASSL OR2 in the presence of spiradoline.

The results of the targeted proliferation assay are shown in the graph of FIG. 10. Exposure of the OR2-expressing rat 1a fibroblasts to the synthetic ligand spiradoline resulted in a 20–50 fold increase in cell proliferation over exposure of the cells to the selected natural ligand dynorphin. Thus, the OR2 RASSL can be used to facilitate selective growth of OR2-expressing cells.

Example 4
Targeted In Vitro Proliferation of RASSL-expressing Cells

The ability of a RASSL to facilitate cell proliferation in a mixed cell population is tested by culturing RASSL-expressing cells with cells of the same cell type that do not express the RASSL (nontarget cells). The mixed cell population is seeded in the culture flask such that the RASSL-expressing cells comprise only about 1% of the total cell population. The cells are then cultured in the presence of spiradoline for 5 to 7 days. The cells are then removed from the culture flask, and RASSL-expressing cells counted by FACS sorting using a fluorescently-labeled, anti-RASSL antibody.

Example 5
Generation of KOR RASSL-expressing Transgenic Mice

The DNA encoding the OR1 RASSL described in Example 1 was inserted into a mammalian expression construct so that expression of the OR1-encoding DNA was driven by a MMTV-LTR promoter according to the expression system developed by Gossen and Bujard (1992, PNAS 89:5547–5551; Gossen et al. 1992, J. Cell Biochem. 59:463–472). OR1 expression construct was then microinjected into fertilized mouse eggs, and the microinjected eggs implanted into pseudopregnant mothers according to methods well known in the art. White blood cells were isolated from the resulting transgenic OR1 mice, and expression of OR1 examined in these cells by FACS using the FLAG monoclonal epitope. Approximately 20% of the white blood cells of the transgenic mice expressed OR1.

Example 6
In Vivo Targeted Proliferation of Cells Expressing a KOR RASSL

Spiradoline or other small molecule KOR drug is administered to a KOR RASSL-expressing transgenic mice (e.g., generated according to the method described in Example 5) with 1 mg/liter in water (oral), or 5 mg/day by injection for up to one year. On weekly intervals, white blood cells are isolated from both KOR RASSL-expressing mice that received the spiradoline, as well as from KOR RASSL-expressing mice that received no drug (control). The percentage of KOR RASSL-expressing white blood cells in each cell sample is determined by FACS.

Example 7
Transplantation of KOR RASSL-expressing Bone Marrow Cells into Nontransgenic Mice and Expansion of KOR RASSL-expressing Cells In Vivo KOR RASSL-expressing bone marrow cells are isolated from transgenic mice generated with RASSL-encoding DNA according to the method described in Example 6. The bone marrow cells are then injected into normal mice. A sample of bone marrow from the KOR RASSL-expressing mice is analyzed by FACS to determine the percentage of KOR RASSL-expressing cells in the population. Spiradoline (or other KOR agonist) is administered to the mice. After 6 months of treatment with the KOR agonist, peripheral cells and/or bone marrow cells are isolated from mice that received the bone marrow transplant (test group), and from mice that received spiradoline, but did not receive the transplant (control group), and from mice that received the transplant, but did not receive spiradoline. The percentage of KOR RASSL-expressing cells is analyzed by FACS as described above and compared to the percentage of KOR RASSL-expressing cells present in the control mice.

Example 8
Production and Characterization of a Serotonin-Receptor RASSL

Serotonin is a biogenic amine. As shown in Table 1, all receptors for biogenic amines bind to their natural ligand via a common mechanism that involves specific residues in the transmembrane helixes: $TM^{-III}$, $TM^{-V}$, $TM^{VI}$ (corresponding to AspII:08, SerV:09, SerV:12, PheVI:17 of the $B_2$-adrenergic receptor; see Schwartz, 1994, supra). Thus, mutations at one or more of these sites would decrease binding to a selected biogenic amine natural ligand, but not the structurally unrelated small molecule ligands.

For example, a RASSL can be generated from the $B_2$-Adrenergic receptor ($\beta_2AR$) by changing the AspIII:08 to a serine. This new receptor no longer binds its natural ligand, yet it will bind, and be activated by, several synthetic small molecule ligands (Strader et al., 1991, *J. Biol. Chem.* 266(1):5–8). FIGS. 11-1 and 11-2 shows an alignment of three exemplary biogenic amine receptors (the human $\beta_2AR$), the human serotonin 1A-receptor (h5HT-1A-R), and the human serotonin-2C-receptor (h5HT-2C-R)) demonstrating the identity of the transmembrane domains (indicated by TM), and the candidate amino acid residues that can be altered to generate a RASSL of the invention.

Example 9
Targeted Proliferation of Microglia Expressing a RASSL and ApoE Variant Isoforms to Treat Alzheimer's Disease Variants of Apolipoprotein E (ApoE) account for a majority of late-onset Alzheimer's disease (for recent reviews see Reiman et al., 1996, *New Engl. J. Med.* 334:752–758; Campion, 1996, *New Engl. J. Med.* 334:791–792). Two percent of the US population is homozygous, and 300 heterozygous, for the ApoE e4 allele, which is associated with development of Alzheimer's. Delivery to the brain of ApoE variants (e2 or e3) may be beneficial for the treatment of Alzheimer's disease.

Delivery of ApoE e2 or e3 can be accomplished using the present invention by transfecting microglia (a major source of ApoE in the brain) with nucleic acid encoding ApoE of the e2 or e3 isoform, and nucleic acid encoding a RASSL of the invention. Alternatively, since microglia are of hematopoietic origin, hematopoietic stem cells (from either bone marrow or peripheral blood of the patient) are transfected with nucleic acid encoding a RASSL and the ApoE e2 or e3 isoform. Since $G_i$ and $G_q$ signals are implicated in proliferative responses of hematopoietic cells, either KOR-based or serotonin receptor-based RASSLs, respectively, are appropriate for inducing a proliferative response in these cells.

The transfected cells are infused back into the patient, and the RASSL agonist is administered (e.g., as a pill taken several times a day). The transfected cells may constitute less than 0.01% of all the patient's stem cells, but RASSL stimulation by administration of the RASSL agonist confers a proliferative advantage upon the RASSL-expressing transfected cells, thereby facilitating a gradual increase in the percent of transfected cells present in the patient up to several percent or even a majority of the cells. The percentage of transfected RASSL-expressing, ApoE-expressing cells is monitored over time by analyzing the peripheral blood for the presence of the RASSL. Gradually, the RASSL containing cells colonize the brain in the form of microglia, which are derived from macrophages and monocytes. Treatment with the RASSL agonist can be continued for months or years to provide for expansion of the RASSL- and ApoE e2- or e3-expressing cells in the patient.

After a period of several months or years the central spinal fluid (CSF) of the patient is analyzed for the Apolipoprotein E isoform(s) to detect a change in the balance of the ApoE isoforms from the Alzheimer's promoting ApoE e4 isoform to another variant such as ApoE e2 or e3. This change in ApoE isoforms can delay or prevent the onset of Alzheimer's disease.

Example 10
Targeted Proliferation of Microglia Expressing a RASSL and Neural Growth Factors to Treat Neurological Disorders Many neurological disorders such as Alzheimer's disease, Parkinson's disease, and Amyotrophic lateral Sclerosis (ALS), are targets for treatment with neural growth factors such as Nerve Growth Factor (NGF). Although these growth factors can be produced in recombinant techniques in large quantities, they are difficult to deliver to the brain because they do not cross the blood-brain barrier.

To accomplish regulated, intracranial delivery using the compositions and methods of the invention, microglia are transformed with DNA encoding NGF (or other desired growth factor) according to methods well known in the art, methods for RASSL medicated expansion of transfected microglia described above in Example 9 could be used. Methods for expression of NGF in transformed cells are known in the art (see, e.g., Cunningham et al., 1994, *Brain Res.* 658:219–231; Tuszynski et al., 1994, *Exper. Neurol.* 126:1–14). Alternatively, the glial cells can be transformed directly using in vivo gene therapy techniques.

Where an ex vivo a gene therapy protocols is used, glial cells expressing both NGF and the RASSL are cultured in vitro, and those RASSL-expressing cells that proliferate and secrete NGF in response to exposure to a synthetic small molecule ligand are used in a cellular implant. After the RASSL-expressing, NGF-producing cellular implant is in place, the synthetic small molecule ligand that binds and activates the RASSL is administered. The synthetic small molecule is of a molecular weight and ionic charge that allows the drug to cross the blood-brain barrier and bind to the RASSLs of RASSL-expressing cellular implant, thus activating the RASSL and facilitating cell proliferation and NGF secretion.

A RASSL agonist that can cross the blood-brain barrier to facilitate delivery of NGF to brain tissue is administered to the patient for several months to years. Therapeutic endpoints may require only a small percentage of microglia to secrete the neural growth factors since these growth factors are quite potent at low concentrations. Many RASSL agonists can cross the blood brain barrier to facilitate the delivery of proteins that can not cross the blood-brain barrier.

Example 11
Regulation of Heart Rate in a Transgenic Animal Expressing the RASSL OR1: An Animal Model of Cardiomyopathy The OR1-expressing transgenic mouse described in Example 5 was used as the basis of an animal model for cardiomyopathy. When activated, the OR1 RASSL results in activation of the $G_i$ protein signaling system. The $G_i$ protein signaling system of cardiac myocytes has been implicated in regulation of heart rate. For example, several investigators have shown a positive correlation between the presence of antibodies that stimulate the $G_i$-coupled muscarinic acetylcholine receptor and several cardiomyopathies (e.g., idiopathic dilated cardiomyopathy, and Chagas disease-associated cardiomyopathy) (see, e.g., Goin et al., 1994, *Neuroimmunomodulation* 1:284–291; Fu, 1995, *Euro. Heart J.* 16(Suppl O):89–91; Fu et al., 1992, *Cardio. Res.* 26:950–955; Fu, 1993, *J. Clin. Invest.* 91:1964–1968; Matsui et al., 1995, *Autoimmunity* 21:85–88). However, this hypothesis has been difficult to prove because the patients have antibodies to many other surface proteins on the heart.

Two transgenic mice were generated: one expressing myosin heavy chain alpha promoter (MHCα) during tTA expression (MHCα-tTA) (to provide cardiac expression of tTA see Yu et al., 1996, *Circulation Res.* 79:691–697; for description of the tTA system, see Gossen et al., 1992, *Proc. Natl. Acad. Sci. USA* 89:5547–5551; and Gossen et al., 1995, *Science* 268:1766–1769) and TRE-OR1 (OR1 RASSL linked to the tetracycline response element (TRE)). The mice were the cross-bred to provide a double transgenic mice. The expression system used allowed for regulated OR1 expression, since the TRE promoter will not be transcribed in the presence of doxycycline. Doxycycline (200 mg/ml in water), which passes efficiently to the fetus and through mother's milk to the newborns, was administered during breeding and continued after weaning. This dose of doxycycline has no known adverse effects on development, and may increase liter size. Doxycycline was replaced with regular water 3 weeks after weaning (day "0" on X-axis of FIG. 12); our previous work has indicated that at least 10 days is required to wash out this high dose of doxycycline. These experiments are referred to as "rapid" induction of OR1 gene expression to differentiate them from studies in which the dose of doxycycline is decreased gradually over 3 months. The control mice were littermates having only one of the transgenes (either MHCα-tTA or TRE-OR).

The results of withdrawal of doxycycline are shown in FIG. 12. As long as the mice were fed doxycycline, they were completely healthy; however, about 75–60% of the mice die 10 days after the start date of a doxycycline-free diet. In contrast, double-transgenic mice continuously fed doxycycline are healthy for at least 3 months. Although the OR1 receptor is reduced in binding to the selected natural liqand dynorphin, activation of OR1 in the double-transgenic mice may have occurred by binding of a nonselected natural liqand (i.e., a natural ligand other than dynorphin).

Despite the apparent existence of another endogenous ligand for OR1 binding, OR1 still meets the definition of a RASSL of the invention since it is still reduced for binding of, and activation by, the selected ligand, dynorphin; and retains binding for a synthetic small molecule (e.g, spiradoline). The nonselected natural ligand in the heart associated with OR1 activation may be a derivative of Met-enkephalin (Met-Enkephalin-Arg-Phe), which has been found in the heart (Barron et al., 1995, *Peptides*, 16:1221–1227; Mansour et al., 1995, *Brain Res.* 700:89–98) and may bind the transgenic KOR RASSL.

Because activation of the endogenous $G_i$-coupled receptor of the heart (cardiac muscarinic) slows heart rate, the $G_i$-protein-coupled RASSL ORl would be expected to reduce heart rate in the transgenic mice. Further while OR1 apparently has a low level of basal activity (as suggested by the data in FIG. 12 described above), supra-activation of the OR1 RASSL with synthetic agonist would further enhance this phenomenon.

This hypothesis was tested by performing electrocardiograms (EKG) on the double transgenic mice. Double-transgenic mice that survived the experiment immediately above were anesthetized with phenobarbital, intubated, and connected to a mouse respiratory ventilator. EKGs were obtained with a standard clinical EKG machine attached to a GRASS physiologic recorder. The control animal in this experiment was a littermate that carried only the MHCα-tTA transgene. After taking baseline recordings, 2 mg of the opioid agonist spiradoline (Pharmacia-Upjohn Kalamazoo, Miss.) was injected intraperitoneallly (IP).

Figure 13:
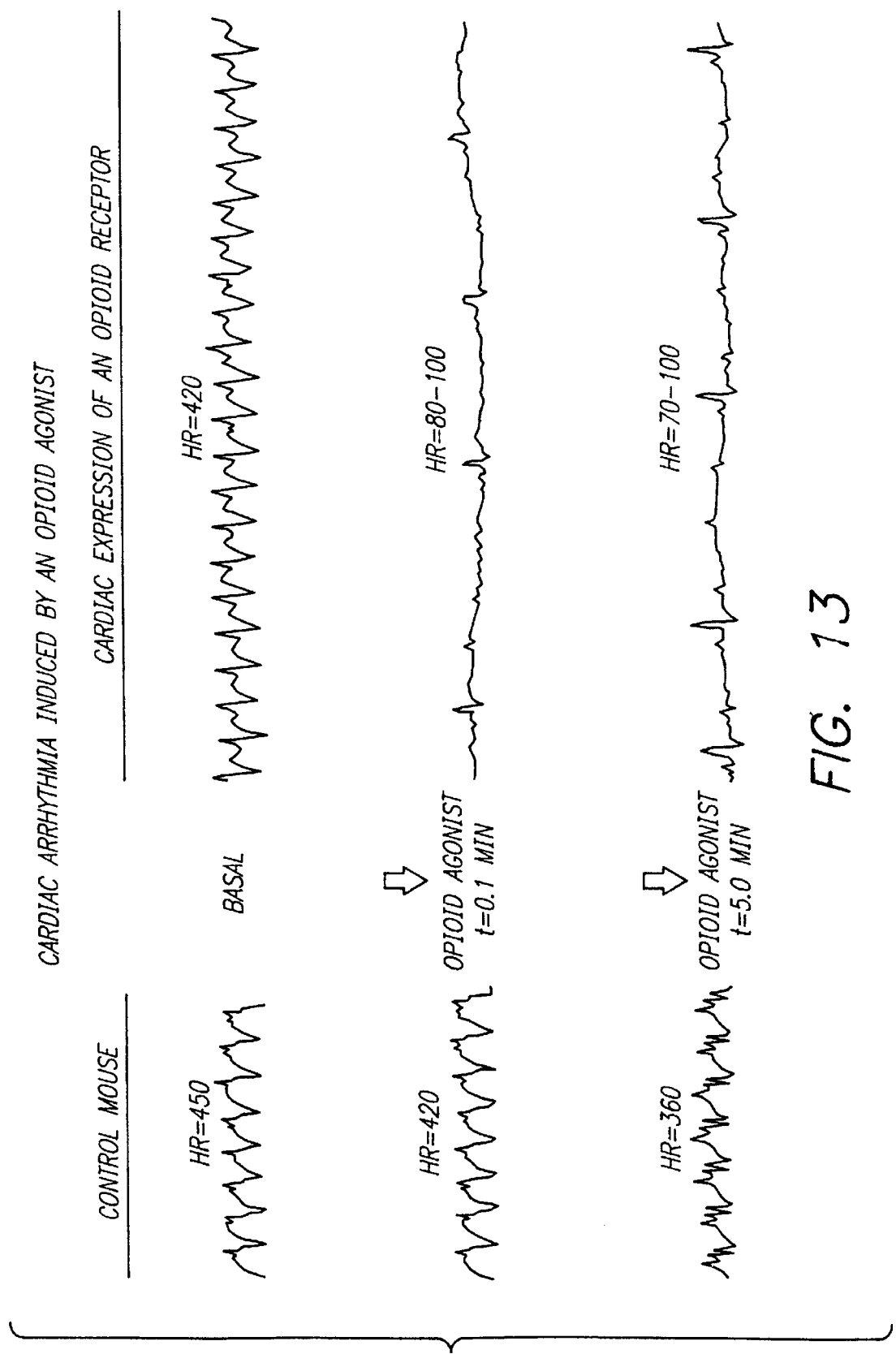
FIG. 13 is an EKG showing induction of cardiac arrhythmia by an opioid agonist in KOR RASSL-expressing transgenic mice.

The results of this experiment are shown in FIG. 13. Recordings obtained a few seconds after the injection show markedly decreased heart rate and an apparent conduction defect consistent with atrioventricular heart block (more apparent in the 5-minute recordings). Similar results have been obtained in two other sets of experiments. The change in the EKG wave form of the control mouse in this experiment may result from a change in the mouse position during the EKG; atrioventricular block or other changes in EKG wave form were not observed in control mice following spiradoline injection.

These data demonstrate that the opioid agonist immediately induced heart block in the OR1-expressing mice consistent with an atrioventricular node disturbance. The rhythm disturbance in the agonist-treated, OR1-expressing mice was similar to the finding in patients with cardiomyopathies associated with muscarinic receptor antibodies (see, e.g., Goin et al., 1994, *Neuroimmunomodulation* 1:284–291; Fu, 1995, *Euro. Heart J.* 16(Suppl O):89–91; Fu, 1993, *J. Clin. Invest.* 91:1964–1968; Matsui et al., 1995, *Autoimmunity* 21:85–88). This experiment also demonstrates that the opioid receptor can still be supraactivated from its baseline state, despite a basal level of activation by a nonselected endogenous ligand.

Figure 14:
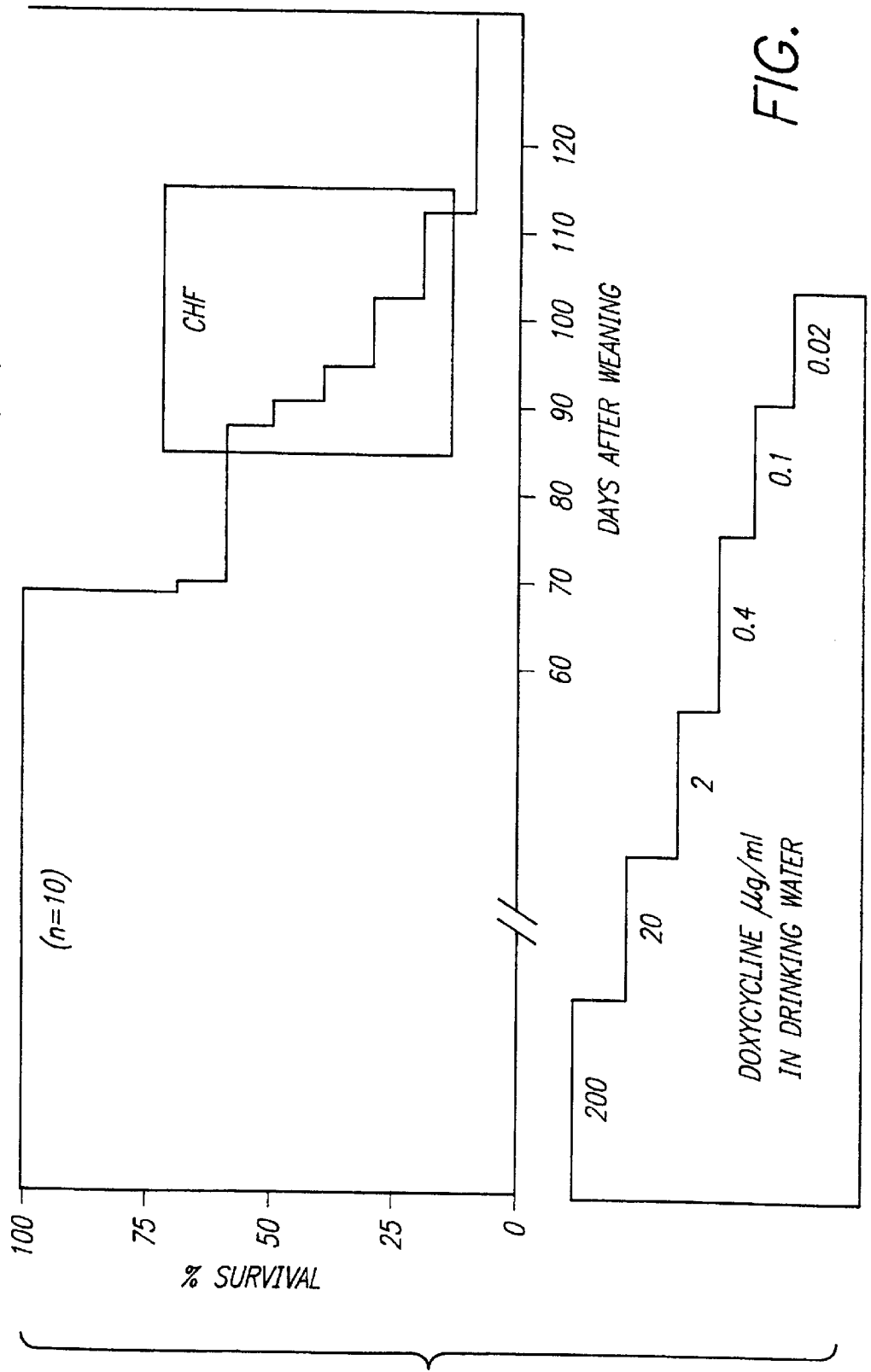
FIG. 14 is a graph showing the development of signs of congestive heart failure upon gradual reduction of doxycycline in RASSL-expressing transgenic mice.

Example 12
OR1-Expressing Transgenic Mice as an Animal Model of Congestive Heart Failure Congestive heart failure (CHF) was mimicked by slowly decreasing, over the course of 3 months, the amount of doxycycline administered to the double transgenic mice described in Example 11, thereby allowing gradual (rather than "rapid") expression of OR1 in heart tissue (see FIG. 14). The CHF syndrome in mice was defined as (1) greater that 20% increase in weight in one week, (2) decreased motor activity of mice, (3) eventual death, (4) fluid accumulatior in the mice, and (5) normal blood chemistries (ruling out other noncardiac forms of fluid retention).

The results are shown in FIG. 14. Following reduction of doxycycline, 5 of the 10 mice developed swelling of soft tissues (interstitial edema), weight gain (20–70% increase from baseline), ascites, and pleural effusions similar to severe CHF within the time period (several weeks) that the animals were on less than 2 mg/ml of doxycycline in their water supply.

In one representative double-transgenic OR1-expressing mouse, the mouse was normal until its dose of doxycycline was lowered from 0.4 mcg/ml to 0.1 mcg/ml. One week after this dose change, the mouse developed rapid weight gain and died 6 days after first developing obvious symptoms of heart failure. The mouse's estimated weight gain was over 50% in one week. At autopsy, this mouse had over 3 ml of clear fluid in its abdominal cavity (no fluid is normal) and a large clear gelatinous subcutaneous accumulation, consistent with interstitial edema (often seen in humans with anasarca). None of the control mice (mice with only one of the two transgenes) showed any deleterious effect of having doxycycline removed from their water supply.

These data show that the OR1-expressing mice provide a model of receptor-induced CHF, useful in the dissection the molecular events that lead to CHF, as well as a mean to screen drugs that may be useful in the treatment of CHF or its symptoms.

The invention now being fully described, it will be apparent to one of ordinary skill in the art that many changes and modifications can be made thereto without departing from the spirit or scope of the appended claims.

What is claimed is:

1. A method for eliciting a G protein-coupled response in a eukaryotic cell in vitro, the method comprising the steps of:

introducing into a eukaryotic cell in vitro a nucleic acid sequence encoding a modified kappa opioid receptor (KOR) comprising an amino acid sequence selected from the group consisting of amino acids 39–414 of SEQ ID NO:6 and amino acids 39–414 of SEQ ID NO:8, wherein the modified KOR is characterized by:
  a) an at least 5-fold decreased binding affinity for a selected naturally occurring ligand of a native KOR,
  b) binding affinity for a synthetic small molecule, and
  c) G protein-coupled activation of a cellular response upon binding of the synthetic small molecule to the modified KOR, said activation being sufficient to obtain a desired cellular response in the eukaryotic cell, said introducing producing a eukaryotic cell expressing the modified KOR; and contacting the eukaryotic cell expressing the modified KOR with the synthetic small molecule;

wherein the synthetic small molecule binds the modified KOR of the eukaryotic cell expressing the modified KOR, thereby activating the modified KOR and inducing the G protein-coupled cellular response activated by the modified KOR.

2. The method of claim 1, wherein the G protein-coupled cellular response is cellular proliferation.

3. The method of claim 1, wherein the G protein-coupled cellular response is cellular secretion of a cellular product.

4. The method of claim 3, wherein the eukaryotic cell contains a nucleic acid sequence encoding a cellular product heterologous to the eukaryotic cell, and the G protein-coupled response is secretion of the heterologous cellular product.

5. A method for eliciting a G protein-mediated response in a cell of a transgenic murine model in vivo, the method comprising:

contacting a cell of a transgenic murine model with synthetic ligand, wherein the transgenic murine comprises a transgene integrated into its genome, said transgene comprising a nucleic acid sequence encoding a modified kappa opioid receptor (KOR) comprising an amino acid sequence selected from the group consisting of amino acids 39–414 of SEQ ID NO:6 and amino acids 39–414 of SEQ ID NO:8, wherein the cell produces the modified KOR, and wherein the modified KOR is characterized by:
  a) an at least 5-fold decreased binding affinity for a selected naturally occurring ligand of a native KOR,
  b) binding affinity for a synthetic ligand, and
  c) G protein-coupled activation of a cellular response upon binding of the synthetic ligand to the modified KOR, said activation being sufficient to obtain a desired cellular response in the eukaryotic cell, wherein the synthetic ligand binds the modified KOR of the cell producing the modified kappa opioid receptor, thereby activating the modified KOR and inducing the G protein-coupled cellular response activated by the modified KOR.

6. The method of claim 5, wherein the G protein-coupled cellular response is cellular proliferation.

7. The method of claim 5, wherein the G protein-coupled cellular response is cellular secretion of a cellular product.

8. The method of claim 7, wherein the eukaryotic cell contains a nucleic acid sequence encoding a cellular product heterologous to the eukaryotic cell, and the G protein-coupled response is secretion of the heterologous cellular product.

9. The method of claim 5, wherein the synthetic ligand is spiradoline.

10. The method of claim 5, wherein the response is decreased heart rate.

11. A method for eliciting a G protein-coupled response in a eukaryotic cell in vitro, the method comprising:

contacting a eukaryotic cell in vitro with a synthetic ligand, wherein the eukaryotic cell produces a modified kappa opioid receptor (KOR), wherein said modified KOR is encoded by a nucleic acid sequence encoding a modified KOR comprising an amino acid sequence selected from the group consisting of amino acids 39–414 of SEQ ID NO:6 and amino acids 39–414 of SEQ ID NO:8, and wherein the modified KOR is characterized by:
  a) an at least 5-fold decreased binding affinity for a selected naturally occurring ligand of a native KOR,
  b) binding affinity for a synthetic ligand, and
  c) G protein-coupled activation of a cellular response upon binding of the synthetic ligand to the modified KOR, said activation being sufficient to obtain a desired cellular response in the eukaryotic cell, wherein the synthetic ligand binds the modified KOR of the eukaryotic cell producing the modified KOR, thereby activating the modified KOR and inducing the G protein-coupled cellular response activated by the modified KOR.

12. The method of claim 11, wherein the G protein-coupled cellular response is cellular proliferation.

13. The method of claim 11, wherein the G protein-coupled cellular response is cellular secretion of a cellular product.

* * * * *

UNITED STATES PATENT AND TRADEMARK OFFICE
CERTIFICATE OF CORRECTION

PATENT NO. : 6,518,480 B1
APPLICATION NO. : 09/341446
DATED : February 11, 2003
INVENTOR(S) : Conklin Page 1 of 1

It is certified that error appears in the above-identified patent and that said Letters Patent is hereby corrected as shown below:

Please replace the Statement as to Rights to Inventors Made Under Federally Sponsored Research and Development beginning on column 1, line 20, with the following revised statement:

STATEMENT AS TO RIGHTS TO INVENTORS MADE UNDER FEDERALLY SPONSORED RESEARCH AND DEVELOPMENT

--This invention was made with Government support under Grant No. HL-02555 awarded by the National Institutes of Health. The Government has certain rights in this invention.--

Signed and Sealed this

Twenty-fourth Day of November, 2009

David J. Kappos
*Director of the United States Patent and Trademark Office*

```
                          SEQUENCE LISTING

<160> NUMBER OF SEQ ID NOS: 12

<210> SEQ ID NO 1
<211> LENGTH: 1143
<212> TYPE: DNA
<213> ORGANISM: Homo sapiens

<400> SEQUENCE: 1
atggactccc cgatccagat cttccgcggg gagccgggcc ctacctgcgc cccgagcgcc      60
tgcctgcccc ccaacagcag cgcctggttt cccggctggg ccgagcccga cagcaacggc     120
agcgccggct cggaggacgc gcagctggag cccgcgcaca tctccccggc catcccggtc     180
atcatcacgg cggtctactc cgtagtgttc gtcgtgggct tggtgggcaa ctcgctggtc     240
atgttcgtga tcatccgata cacaaagatg aagacagcaa ccaacattta catatttaac     300
ctggctttgg cagatgcttt agttactaca accatgccct ttcagagtac ggtctacttg     360
atgaattcct ggcctttggg ggatgtgctg tgcaagatag taatttccat tgattactac     420
aacatgttca ccagcatctt caccttgacc atgatgagcg tggaccgcta cattgccgtg     480
tgccaccccg tgaaggcttt ggacttccgc acacccttga aggcaaagat catcaatatc     540
tgcatctggc tgctgtcgtc atctgttggc atctctgcaa tagtccttgg aggcaccaaa     600
gtcagggaag acgtcgatgt cattgagtgc tccttgcagt tcccagatga tgactactcc     660
tggtgggacc tcttcatgaa gatctgcgtc ttcatctttg ccttcgtgat ccctgtcctc     720
atcatcatcg tctgctacac cctgatgatc ctgcgtctca agagcgtccg gctcctttct     780
ggctcccgag agaaagatcg caacctgcgt aggatcacca gactggtcct ggtggtggtg     840
gcagtcttcg tcgtctgctg gactcccatt cacatattca tcctggtgga ggctctgggg     900
agcacctccc acagcacagc tgctctctcc agctattact tctgcatcgc cttaggctat     960
accaacagta gcctgaatcc cattctctac gcctttcttg atgaaaactt caagcggtgt    1020
ttccgggact tctgctttcc actgaagatg aggatggagc ggcagagcac tagcagagtc    1080
cgaaatacag ttcaggatcc tgcttacctg agggacatcg atgggatgaa taaaccagta    1140
tga                                                                 1143

<210> SEQ ID NO 2
<211> LENGTH: 380
<212> TYPE: PRT
<213> ORGANISM: Homo sapiens

<400> SEQUENCE: 2
```

```
Met Asp Ser Pro Ile Gln Ile Phe Arg Gly Glu Pro Gly Pro Thr Cys
 1               5                  10                 15

Ala Pro Ser Ala Cys Leu Pro Pro Asn Ser Ser Ala Trp Phe Pro Gly
            20                  25                  30

Trp Ala Glu Pro Asp Ser Asn Gly Ser Ala Gly Ser Glu Asp Ala Gln
        35                  40                  45

Leu Glu Pro Ala His Ile Ser Pro Ala Ile Pro Val Ile Ile Thr Ala
    50                  55                  60

Val Tyr Ser Val Val Phe Val Val Gly Leu Val Gly Asn Ser Leu Val
 65                  70                  75                  80

Met Phe Val Ile Ile Arg Tyr Thr Lys Met Lys Thr Ala Thr Asn Ile
                 85                  90                  95

Tyr Ile Phe Asn Leu Ala Leu Ala Asp Ala Leu Val Thr Thr Thr Met
                100                 105                 110

Pro Phe Gln Ser Thr Val Tyr Leu Met Asn Ser Trp Pro Phe Gly Asp
                115                 120                 125

Val Leu Cys Lys Ile Val Ile Ser Ile Asp Tyr Tyr Asn Met Phe Thr
130                 135                 140

Ser Ile Phe Thr Leu Thr Met Met Ser Val Asp Arg Tyr Ile Ala Val
145                 150                 155                 160

Cys His Pro Val Lys Ala Leu Asp Phe Arg Thr Pro Leu Lys Ala Lys
                165                 170                 175

Ile Ile Asn Ile Cys Ile Trp Leu Leu Ser Ser Ser Val Gly Ile Ser
                180                 185                 190

Ala Ile Val Leu Gly Gly Thr Lys Val Arg Glu Asp Val Asp Val Ile
                195                 200                 205

Glu Cys Ser Leu Gln Phe Pro Asp Asp Tyr Ser Trp Trp Asp Leu
210                 215                 220

Phe Met Lys Ile Cys Val Phe Ile Phe Ala Phe Val Ile Pro Val Leu
225                 230                 235                 240

Ile Ile Ile Val Cys Tyr Thr Leu Met Ile Leu Arg Leu Lys Ser Val
                245                 250                 255

Arg Leu Leu Ser Gly Ser Arg Glu Lys Asp Arg Asn Leu Arg Arg Ile
                260                 265                 270

Thr Arg Leu Val Leu Val Val Val Ala Val Phe Val Val Cys Trp Thr
                275                 280                 285

Pro Ile His Ile Phe Ile Leu Val Glu Ala Leu Gly Ser Thr Ser His
                290                 295                 300

Ser Thr Ala Ala Leu Ser Ser Tyr Tyr Phe Cys Ile Ala Leu Gly Tyr
305                 310                 315                 320

Thr Asn Ser Ser Leu Asn Pro Ile Leu Tyr Ala Phe Leu Asp Glu Asn
                325                 330                 335

Phe Lys Arg Cys Phe Arg Asp Phe Cys Phe Pro Leu Lys Met Arg Met
                340                 345                 350

Glu Arg Gln Ser Thr Ser Arg Val Arg Asn Thr Val Gln Asp Pro Ala
                355                 360                 365

Tyr Leu Arg Asp Ile Asp Gly Met Asn Lys Pro Val
                370                 375                 380

<210> SEQ ID NO 3
<211> LENGTH: 1284
<212> TYPE: DNA
<213> ORGANISM: Artificial Sequence
<220> FEATURE:
<223> OTHER INFORMATION: modified KOR
```

-continued

```
<400> SEQUENCE: 3
atggacagca aaggttcgtc gcagaaaggg tcccgcctgc tcctgctgct ggtggtgtca      60
aatctactct tgtgccaggg tgtggtctcc gattacaaag atgatgatga tgtcgactcc     120
ccgatccaga tcttccgcgg ggagccgggc cctacctgcg ccccgagcgc ctgcctgccc     180
cccaacagca gcgcctggtt tcccggctgg gccgagcccg acagcaacgg cagcgccggc     240
tcggaggacg cgcagctgga gcccgcgcac atctccccgg ccatcccggt catcatcacg     300
gcggtctact ccgtagtgtt cgtcgtgggc ttggtgggca actcgctggt catgttcgtg     360
atcatccgat acacaaagat gaagacagca accaacattt acatatttaa cctggctttg     420
gcagatgctt tagttactac aaccatgccc tttcagagta cggtctactt gatgaattcc     480
tggccttttg gggatgtgct gtgcaagata gtaatttcca ttgattacta caacatgttc     540
accagcatct tcaccttgac catgatgagc gtggaccgct acattgccgt gtgccacccc     600
gtgaaggctt tggacttccg cacacccttg aaggcaaaga tcatcaatat ctgcatctgg     660
ctgctgtcgt catctgttgg catctctgca atagtccttg gaggcaccaa agtcagggaa     720
gacgtcgatg tcattgagtg ctccttgcag ttcccagatg atgactactc tggtgggac     780
ctcttcatga agatctgcgt cttcatcttt gccttcgtga tccctgtcct catcatcatc     840
gtctgctaca ccctgatgat cctgcgtctc aagagcgtcc ggctcctttc tggctcccga     900
gagaaagatc gcaacctgcg taggatcacc agactggtcc tggtggtggt ggcagtcttc     960
gtcgtctgct ggactcccat tcacatattc atcctggtgg aggctctggg gagcacctcc    1020
cacagcacag ctgctctctc cagctattac ttctgcatcg ccttaggcta taccaacagt    1080
agcctgaatc ccattctcta cgcctttctt gatgaaaact tcaagcggtg tttccgggac    1140
ttctgctttc cactgaagat gaggatggag cggcagagca ctagcagagt ccgaaataca    1200
gttcaggatc ctgcttacct gagggacatc gatgggatga ataaaccagt aggttacccc    1260
tacgacgtcc ccgactacgc ctga                                           1284

<210> SEQ ID NO 4
<211> LENGTH: 427
<212> TYPE: PRT
<213> ORGANISM: Artificial Sequence
<220> FEATURE:
<223> OTHER INFORMATION: modified KOR

<400> SEQUENCE: 4

Met Asp Ser Lys Gly Ser Ser Gln Lys Gly Ser Arg Leu Leu Leu Leu
  1               5                  10                  15

Leu Val Val Ser Asn Leu Leu Leu Cys Gln Gly Val Val Ser Asp Tyr
                 20                  25                  30

Lys Asp Asp Asp Val Asp Ser Pro Ile Gln Ile Phe Arg Gly Glu
             35                  40                  45

Pro Gly Pro Thr Cys Ala Pro Ser Ala Cys Leu Pro Pro Asn Ser Ser
         50                  55                  60

Ala Trp Phe Pro Gly Trp Ala Glu Pro Asp Ser Asn Gly Ser Ala Gly
 65                  70                  75                  80

Ser Glu Asp Ala Gln Leu Glu Pro Ala His Ile Ser Pro Ala Ile Pro
                 85                  90                  95

Val Ile Ile Thr Ala Val Tyr Ser Val Val Phe Val Val Gly Leu Val
            100                 105                 110

Gly Asn Ser Leu Val Met Phe Val Ile Ile Arg Tyr Thr Lys Met Lys
```

|     |     |     |     |     |     |     |     |     |     |     |
|-----|-----|-----|-----|-----|-----|-----|-----|-----|-----|-----|
|     | 115 |     |     |     | 120 |     |     |     | 125 |     |

Thr Ala Thr Asn Ile Tyr Ile Phe Asn Leu Ala Leu Ala Asp Ala Leu
                130               135               140

Val Thr Thr Thr Met Pro Phe Gln Ser Thr Val Tyr Leu Met Asn Ser
145               150               155               160

Trp Pro Phe Gly Asp Val Leu Cys Lys Ile Val Ile Ser Ile Asp Tyr
                165               170               175

Tyr Asn Met Phe Thr Ser Ile Phe Thr Leu Thr Met Met Ser Val Asp
                180               185               190

Arg Tyr Ile Ala Val Cys His Pro Val Lys Ala Leu Asp Phe Arg Thr
                195               200               205

Pro Leu Lys Ala Lys Ile Ile Asn Ile Cys Ile Trp Leu Leu Ser Ser
                210               215               220

Ser Val Gly Ile Ser Ala Ile Val Leu Gly Gly Thr Lys Val Arg Glu
225               230               235               240

Asp Val Asp Val Ile Glu Cys Ser Leu Gln Phe Pro Asp Asp Asp Tyr
                245               250               255

Ser Trp Trp Asp Leu Phe Met Lys Ile Cys Val Phe Ile Phe Ala Phe
                260               265               270

Val Ile Pro Val Leu Ile Ile Ile Val Cys Tyr Thr Leu Met Ile Leu
                275               280               285

Arg Leu Lys Ser Val Arg Leu Leu Ser Gly Ser Arg Glu Lys Asp Arg
290               295               300

Asn Leu Arg Arg Ile Thr Arg Leu Val Leu Val Val Ala Val Phe
305               310               315               320

Val Val Cys Trp Thr Pro Ile His Ile Phe Ile Leu Val Glu Ala Leu
                325               330               335

Gly Ser Thr Ser His Ser Thr Ala Ala Leu Ser Ser Tyr Tyr Phe Cys
                340               345               350

Ile Ala Leu Gly Tyr Thr Asn Ser Ser Leu Asn Pro Ile Leu Tyr Ala
                355               360               365

Phe Leu Asp Glu Asn Phe Lys Arg Cys Phe Arg Asp Phe Cys Phe Pro
                370               375               380

Leu Lys Met Arg Met Glu Arg Gln Ser Thr Ser Arg Val Arg Asn Thr
385               390               395               400

Val Gln Asp Pro Ala Tyr Leu Arg Asp Ile Asp Gly Met Asn Lys Pro
                405               410               415

Val Gly Tyr Pro Tyr Asp Val Pro Asp Tyr Ala
                420               425

<210> SEQ ID NO 5
<211> LENGTH: 1275
<212> TYPE: DNA
<213> ORGANISM: Artificial Sequence
<220> FEATURE:
<223> OTHER INFORMATION: RASSL OR1

<400> SEQUENCE: 5
atggacagca aaggttcgtc gcagaaaggg tcccgcctgc tcctgctgct ggtggtgtca     60
aatctactct tgtgccaggg tgtggtctcc gattacaaag atgatgatga tgtcgactcc    120
ccgatccaga tcttccgcgg ggagccgggc cctacctgcg ccccgagcgc ctgcctgccc    180
cccaacagca gcgcctggtt tcccggctgg gccgagcccg acagcaacgg cagcgccggc    240
tcggaggacg cgcagctgga gcccgcgcac atctcccccg ccatcccggt catcatcacg    300

-continued

```
gcggtctact ccgtagtgtt cgtcgtgggc ttggtgggca actcgctggt catgttcgtg    360
atcatccgat acacaaagat gaagacagca accaacattt acatatttaa cctggctttg    420
gcagatgctt tagttactac aaccatgccc tttcagagta cggtctactt gatgaattct    480
tggccttttg gagatgttct gtgcaagatt gtcatttcca ttgactacta acacatgttt    540
accagcatat tcaccttgac catgatgagt gtggaccgtt acattgccgt gtgccaccct    600
gtgaaagctt tggatttccg aacacctttg aaagcaaaga tcatcaacat ctgcatttgg    660
ctactggcat catctgttgg tatatcagcg atagtccttg gggtgaccca accccgggat    720
ggagcagtgg tatgcacgct ccagttcccc agccccagct ggtactggga cactgtgacc    780
aagatctgcg tcttcatctt tgccttcgtg atccctgtcc tcatcatcat cgtctgctac    840
accctgatga tcctgcgtct caagagcgtc cggctccttt ctggctcccg agagaaagat    900
cgcaacctgc gtaggatcac cagactggtc ctggtggtgg tggcagtctt cgtcgtctgc    960
tggactccca ttcacatatt catcctggtg gaggctctgg ggagcacctc ccacagcaca   1020
gctgctctct ccagctatta cttctgcatc gccttaggct ataccaacag tagcctgaat   1080
cccattctct acgcctttct tgatgaaaac ttcaagcggt gtttccggga cttctgcttt   1140
ccactgaaga tgaggatgga gcggcagagc actagcagag tccgaaatac agttcaggat   1200
cctgcttacc tgagggacat cgatgggatg aataaaccag taggttaccc ctacgacgtc   1260
cccgactacg cctga                                                    1275
```

<210> SEQ ID NO 6
<211> LENGTH: 424
<212> TYPE: PRT
<213> ORGANISM: Artificial Sequence
<220> FEATURE:
<223> OTHER INFORMATION: RASSL OR1

<400> SEQUENCE: 6

```
Met Asp Ser Lys Gly Ser Ser Gln Lys Gly Ser Arg Leu Leu Leu Leu
  1               5                  10                  15

Leu Val Val Ser Asn Leu Leu Leu Cys Gln Gly Val Val Ser Asp Tyr
             20                  25                  30

Lys Asp Asp Asp Asp Val Asp Ser Pro Ile Gln Ile Phe Arg Gly Glu
         35                  40                  45

Pro Gly Pro Thr Cys Ala Pro Ser Ala Cys Leu Pro Pro Asn Ser Ser
     50                  55                  60

Ala Trp Phe Pro Gly Trp Ala Glu Pro Asp Ser Asn Gly Ser Ala Gly
 65                  70                  75                  80

Ser Glu Asp Ala Gln Leu Glu Pro Ala His Ile Ser Pro Ala Ile Pro
                 85                  90                  95

Val Ile Ile Thr Ala Val Tyr Ser Val Val Phe Val Val Gly Leu Val
            100                 105                 110

Gly Asn Ser Leu Val Met Phe Val Ile Ile Arg Tyr Thr Lys Met Lys
        115                 120                 125

Thr Ala Thr Asn Ile Tyr Ile Phe Asn Leu Ala Leu Ala Asp Ala Leu
    130                 135                 140

Val Thr Thr Thr Met Pro Phe Gln Ser Thr Val Tyr Leu Met Asn Ser
145                 150                 155                 160

Trp Pro Phe Gly Asp Val Leu Cys Lys Ile Val Ile Ser Ile Asp Tyr
                165                 170                 175

Tyr Asn Met Phe Thr Ser Ile Phe Thr Leu Thr Met Met Ser Val Asp
            180                 185                 190
```

```
Arg Tyr Ile Ala Val Cys His Pro Val Lys Ala Leu Asp Phe Arg Thr
            195                 200                 205
Pro Leu Lys Ala Lys Ile Ile Asn Ile Cys Ile Trp Leu Leu Ala Ser
        210                 215                 220
Ser Val Gly Ile Ser Ala Ile Val Leu Gly Val Thr Gln Pro Arg Asp
225                 230                 235                 240
Gly Ala Val Val Cys Thr Leu Gln Phe Pro Ser Pro Ser Trp Tyr Trp
                245                 250                 255
Asp Thr Val Thr Lys Ile Cys Val Phe Ile Phe Ala Phe Val Ile Pro
            260                 265                 270
Val Leu Ile Ile Ile Val Cys Tyr Thr Leu Met Ile Leu Arg Leu Lys
        275                 280                 285
Ser Val Arg Leu Leu Ser Gly Ser Arg Glu Lys Asp Arg Asn Leu Arg
290                 295                 300
Arg Ile Thr Arg Leu Val Leu Val Val Val Ala Val Phe Val Val Cys
305                 310                 315                 320
Trp Thr Pro Ile His Ile Phe Ile Leu Val Glu Ala Leu Gly Ser Thr
                325                 330                 335
Ser His Ser Thr Ala Ala Leu Ser Ser Tyr Tyr Phe Cys Ile Ala Leu
            340                 345                 350
Gly Tyr Thr Asn Ser Ser Leu Asn Pro Ile Leu Tyr Ala Phe Leu Asp
        355                 360                 365
Glu Asn Phe Lys Arg Cys Phe Arg Asp Phe Cys Phe Pro Leu Lys Met
370                 375                 380
Arg Met Glu Arg Gln Ser Thr Ser Arg Val Arg Asn Thr Val Gln Asp
385                 390                 395                 400
Pro Ala Tyr Leu Arg Asp Ile Asp Gly Met Asn Lys Pro Val Gly Tyr
                405                 410                 415
Pro Tyr Asp Val Pro Asp Tyr Ala
            420

<210> SEQ ID NO 7
<211> LENGTH: 1275
<212> TYPE: DNA
<213> ORGANISM: Artificial Sequence
<220> FEATURE:
<223> OTHER INFORMATION: RASSL OR2

<400> SEQUENCE: 7
atggacagca aaggttcgtc gcagaaaggg tcccgcctgc tcctgctgct ggtggtgtca      60
aatctactct tgtgccaggg tgtggtctcc gattacaaag atgatgatga tgtcgactcc     120
ccgatccaga tcttccgcgg ggagccgggc cctacctgcg ccccgagcgc ctgcctgccc     180
cccaacagca gcgcctggtt tcccggctgg gccgagcccg acagcaacgg cagcgccggc     240
tcggaggacg cgcagctgga gcccgcgcac atctccccgg ccatcccggt catcatcacg     300
gcggtctact ccgtagtgtt cgtcgtgggc ttggtgggca actcgctggt catgttcgtg     360
atcatccgat acacaaagat gaagacagca accaacattt acatatttaa cctggctttg     420
gcagatgctt tagttactac aaccatgccc tttcagagta cggtctactt gatgaattct     480
tggccttttg gagatgttct gtgcaagatt gtcatttcca ttgactacta caacatgttt     540
accagcatat tcaccttgac catgatgagt gtggaccgtt acattgccgt gtgccaccct     600
gtgaaagctt tggatttccg aacacctttg aaagcaaaga tcatcaacat ctgcatttgg     660
ctactggcat catctgttgg tatatcagcg atagtccttg gggtgaccca accccgggat     720
```

```
ggagcagtgg tatgcacgct ccagttcccc agccccagct ggtactggga cactgtgacc    780
aagatctgcg tcttcatctt tgccttcgtg atccctgtcc tcatcatcat cgtctgctac    840
accctgatga tcctgcgtct caagagcgtc cggctccttt ctggctcccg agagaaagat    900
cgcaacctgc gtaggatcac cagactggtc ctggtggtgg tggcagtctt cgtcgtctgc    960
tggactccca ttcacatatt catcctagtt caggctctgg ggagcacctc ccacagcaca   1020
gctgctctct ccagctatta cttctgcatc gccttaggct ataccaacag tagcctgaat   1080
cccattctct acgcctttct tgatgaaaac ttcaagcggt gtttccggga cttctgcttt   1140
ccactgaaga tgaggatgga gcggcagagc actagcagag tccgaaatac agttcaggat   1200
cctgcttacc tgagggacat cgatgggatg aataaaccag taggttaccc ctacgacgtc   1260
cccgactacg cctga                                                   1275
```

<210> SEQ ID NO 8
<211> LENGTH: 424
<212> TYPE: PRT
<213> ORGANISM: Artificial Sequence
<220> FEATURE:
<223> OTHER INFORMATION: RASSL OR2

<400> SEQUENCE: 8

```
Met Asp Ser Lys Gly Ser Ser Gln Lys Gly Ser Arg Leu Leu Leu Leu
  1               5                  10                  15

Leu Val Ser Asn Leu Leu Cys Gln Gly Val Val Ser Asp Tyr
             20                  25                  30

Lys Asp Asp Asp Val Asp Ser Pro Ile Gln Ile Phe Arg Gly Glu
             35                  40                  45

Pro Gly Pro Thr Cys Ala Pro Ser Ala Cys Leu Pro Pro Asn Ser Ser
 50                  55                  60

Ala Trp Phe Pro Gly Trp Ala Glu Pro Asp Ser Asn Gly Ser Ala Gly
 65                  70                  75                  80

Ser Glu Asp Ala Gln Leu Glu Pro Ala His Ile Ser Pro Ala Ile Pro
             85                  90                  95

Val Ile Ile Thr Ala Val Tyr Ser Val Val Phe Val Val Gly Leu Val
            100                 105                 110

Gly Asn Ser Leu Val Met Phe Val Ile Ile Arg Tyr Thr Lys Met Lys
            115                 120                 125

Thr Ala Thr Asn Ile Tyr Ile Phe Asn Leu Ala Leu Ala Asp Ala Leu
            130                 135                 140

Val Thr Thr Thr Met Pro Phe Gln Ser Thr Val Tyr Leu Met Asn Ser
145                 150                 155                 160

Trp Pro Phe Gly Asp Val Leu Cys Lys Ile Val Ile Ser Ile Asp Tyr
                165                 170                 175

Tyr Asn Met Phe Thr Ser Ile Phe Thr Leu Thr Met Met Ser Val Asp
            180                 185                 190

Arg Tyr Ile Ala Val Cys His Pro Val Lys Ala Leu Asp Phe Arg Thr
            195                 200                 205

Pro Leu Lys Ala Lys Ile Ile Asn Ile Cys Ile Trp Leu Leu Ala Ser
            210                 215                 220

Ser Val Gly Ile Ser Ala Ile Val Leu Gly Val Thr Gln Pro Arg Asp
225                 230                 235                 240

Gly Ala Val Val Cys Thr Leu Gln Phe Pro Ser Pro Ser Trp Tyr Trp
                245                 250                 255
```

```
Asp Thr Val Thr Lys Ile Cys Val Phe Ile Phe Ala Phe Val Ile Pro
            260                 265                 270

Val Leu Ile Ile Ile Val Cys Tyr Thr Leu Met Ile Leu Arg Leu Lys
            275                 280                 285

Ser Val Arg Leu Leu Ser Gly Ser Arg Glu Lys Asp Arg Asn Leu Arg
    290                 295                 300

Arg Ile Thr Arg Leu Val Leu Val Val Ala Val Phe Val Val Cys
305                 310                 315                 320

Trp Thr Pro Ile His Ile Phe Ile Leu Val Gln Ala Leu Gly Ser Thr
                325                 330                 335

Ser His Ser Thr Ala Ala Leu Ser Ser Tyr Tyr Phe Cys Ile Ala Leu
            340                 345                 350

Gly Tyr Thr Asn Ser Ser Leu Asn Pro Ile Leu Tyr Ala Phe Leu Asp
            355                 360                 365

Glu Asn Phe Lys Arg Cys Phe Arg Asp Phe Cys Phe Pro Leu Lys Met
        370                 375                 380

Arg Met Glu Arg Gln Ser Thr Ser Arg Val Arg Asn Thr Val Gln Asp
385                 390                 395                 400

Pro Ala Tyr Leu Arg Asp Ile Asp Gly Met Asn Lys Pro Val Gly Tyr
                405                 410                 415

Pro Tyr Asp Val Pro Asp Tyr Ala
            420

<210> SEQ ID NO 9
<211> LENGTH: 423
<212> TYPE: PRT
<213> ORGANISM: Homo sapiens

<400> SEQUENCE: 9

Met Gly Gln Pro Gly Asn Gly Ser Ala Phe Leu Leu Ala Pro Asn Arg
1               5                   10                  15

Ser His Ala Pro Asp His Asp Val Thr Gln Gln Arg Asp Glu Val Trp
            20                  25                  30

Val Val Gly Met Gly Ile Val Met Ser Leu Ile Val Leu Ala Ile Val
        35                  40                  45

Phe Gly Asn Val Leu Val Ile Thr Ala Ile Ala Lys Phe Glu Arg Leu
    50                  55                  60

Gln Thr Val Thr Asn Tyr Phe Ile Thr Ser Leu Ala Cys Ala Asp Leu
65                  70                  75                  80

Val Met Gly Leu Ala Val Val Pro Phe Gly Ala Ala His Ile Leu Met
                85                  90                  95

Lys Met Trp Thr Phe Gly Asn Phe Trp Cys Glu Phe Trp Thr Ser Ile
            100                 105                 110

Asp Val Leu Cys Val Thr Ala Ser Ile Glu Thr Leu Cys Val Ile Ala
        115                 120                 125

Val Asp Arg Tyr Phe Ala Ile Thr Ser Pro Phe Lys Tyr Gln Ser Leu
    130                 135                 140

Leu Thr Lys Asn Lys Ala Arg Val Ile Ile Leu Met Val Trp Ile Val
145                 150                 155                 160

Ser Gly Leu Thr Ser Phe Leu Pro Ile Gln Met His Trp Tyr Arg Ala
                165                 170                 175

Thr His Gln Glu Ala Ile Asn Cys Tyr Ala Asn Glu Thr Cys Cys Asp
            180                 185                 190

Phe Phe Thr Asn Gln Ala Tyr Ala Ile Ala Ser Ser Ile Val Ser Phe
        195                 200                 205
```

```
Tyr Val Pro Leu Val Ile Met Val Phe Val Tyr Ser Arg Val Phe Gln
    210                 215                 220
Glu Ala Lys Arg Gln Leu Gln Lys Ile Asp Lys Ser Glu Gly Arg Phe
225                 230                 235                 240
His Val Gln Asn Leu Ser Gln Val Glu Gln Asp Gly Arg Thr Gly His
                245                 250                 255
Gly Leu Arg Arg Ser Ser Lys Phe Cys Leu Lys Glu His Lys Ala Leu
            260                 265                 270
Lys Thr Leu Gly Ile Ile Met Gly Thr Phe Thr Leu Cys Trp Leu Pro
        275                 280                 285
Phe Phe Ile Val Asn Ile Val His Val Ile Gln Asp Asn Leu Ile Arg
    290                 295                 300
Lys Glu Val Tyr Ile Leu Leu Asn Trp Ile Gly Tyr Val Asn Ser Gly
305                 310                 315                 320
Phe Asn Pro Leu Ile Tyr Cys Arg Ser Pro Asp Phe Arg Ile Ala Phe
                325                 330                 335
Gln Glu Leu Leu Cys Leu Arg Arg Ser Ser Leu Lys Ala Tyr Gly Asn
            340                 345                 350
Gly Tyr Ser Ser Asn Gly Asn Thr Gly Glu Gln Ser Gly Tyr His Val
        355                 360                 365
Glu Gln Glu Lys Glu Asn Lys Leu Leu Cys Glu Asp Leu Pro Gly Thr
    370                 375                 380
Glu Asp Phe Val Gly His Gln Gly Thr Val Pro Ser Asp Asn Ile Asp
385                 390                 395                 400
Ser Gln Gly Arg Asn Cys Ser Thr Asn Asp Ser Leu Leu Glu Glu Glu
                405                 410                 415
Glu Tyr Met Pro Met Glu Glx
            420

<210> SEQ ID NO 10
<211> LENGTH: 422
<212> TYPE: PRT
<213> ORGANISM: Homo sapiens

<400> SEQUENCE: 10

Met Asp Val Leu Ser Pro Gly Gln Gly Asn Asn Thr Thr Ser Pro Pro
1               5                   10                  15
Ala Pro Phe Glu Thr Gly Gly Asn Thr Thr Gly Ile Ser Asp Val Thr
            20                  25                  30
Val Ser Tyr Gln Val Ile Thr Ser Leu Leu Leu Gly Thr Leu Ile Phe
        35                  40                  45
Cys Ala Val Leu Gly Asn Ala Cys Val Val Ala Ala Ile Ala Leu Glu
    50                  55                  60
Arg Ser Leu Gln Asn Val Ala Asn Tyr Leu Ile Gly Ser Leu Ala Val
65                  70                  75                  80
Thr Asp Leu Met Val Ser Val Leu Val Leu Pro Met Ala Ala Leu Tyr
                85                  90                  95
Gln Val Leu Asn Lys Trp Thr Leu Gly Gln Val Thr Cys Asp Leu Phe
            100                 105                 110
Ile Ala Leu Asp Val Leu Cys Cys Thr Ser Ser Ile Leu His Leu Cys
        115                 120                 125
Ala Ile Ala Leu Asp Arg Tyr Trp Ala Ile Thr Asp Pro Ile Asp Tyr
    130                 135                 140
Val Asn Lys Arg Thr Pro Arg Arg Ala Ala Ala Leu Ile Ser Leu Thr
```

-continued

```
         145                 150                 155                 160
Trp Leu Ile Gly Phe Leu Ile Ser Ile Pro Pro Met Leu Gly Trp Arg
                165                 170                 175

Thr Pro Glu Asp Arg Ser Asp Pro Asp Ala Cys Thr Ile Ser Lys Asp
            180                 185                 190

His Gly Tyr Thr Ile Tyr Ser Thr Phe Gly Ala Phe Tyr Ile Pro Leu
        195                 200                 205

Leu Leu Met Leu Val Leu Tyr Gly Arg Ile Phe Arg Ala Ala Arg Phe
    210                 215                 220

Arg Ile Arg Lys Thr Val Lys Lys Val Glu Lys Thr Gly Ala Asp Thr
225                 230                 235                 240

Arg His Gly Ala Ser Pro Ala Pro Gln Pro Lys Lys Ser Val Asn Gly
                245                 250                 255

Glu Ser Gly Ser Arg Asn Trp Arg Leu Gly Val Glu Ser Lys Ala Gly
            260                 265                 270

Gly Ala Leu Cys Ala Asn Gly Ala Val Arg Gln Gly Asp Asp Gly Ala
        275                 280                 285

Ala Leu Glu Val Ile Glu Val His Arg Val Gly Asn Ser Lys Glu His
    290                 295                 300

Leu Pro Leu Pro Ser Glu Ala Gly Pro Thr Pro Cys Ala Pro Ala Ser
305                 310                 315                 320

Phe Glu Arg Lys Asn Glu Arg Asn Ala Glu Ala Lys Arg Lys Met Ala
                325                 330                 335

Leu Ala Arg Glu Arg Lys Thr Val Lys Thr Leu Gly Ile Ile Met Gly
            340                 345                 350

Thr Phe Ile Leu Cys Trp Leu Pro Phe Phe Ile Val Ala Leu Val Leu
        355                 360                 365

Pro Phe Cys Glu Ser Ser Cys His Met Pro Thr Leu Leu Gly Ala Ile
    370                 375                 380

Ile Asn Trp Leu Gly Tyr Ser Asn Ser Leu Leu Asn Pro Val Ile Tyr
385                 390                 395                 400

Ala Tyr Phe Asn Lys Asp Phe Gln Asn Ala Phe Lys Lys Ile Ile Lys
                405                 410                 415

Cys Lys Phe Cys Arg Gln
            420
```

<210> SEQ ID NO 11
<211> LENGTH: 458
<212> TYPE: PRT
<213> ORGANISM: Homo sapiens

<400> SEQUENCE: 11

```
Met Val Asn Leu Arg Asn Ala Val His Ser Phe Leu Val His Leu Ile
 1               5                  10                  15

Gly Leu Leu Val Trp Gln Cys Asp Ile Ser Val Ser Pro Val Ala Ala
                20                  25                  30

Ile Val Thr Asp Ile Phe Asn Thr Ser Asp Gly Gly Arg Phe Lys Phe
            35                  40                  45

Pro Asp Gly Val Gln Asn Trp Pro Ala Leu Ser Ile Val Ile Ile Ile
        50                  55                  60

Ile Met Thr Ile Gly Gly Asn Ile Leu Val Ile Met Ala Val Ser Met
65                  70                  75                  80

Glu Lys Lys Leu His Asn Ala Thr Asn Tyr Phe Leu Met Ser Leu Ala
                85                  90                  95
```

```
Ile Ala Asp Met Leu Val Gly Leu Leu Val Met Pro Leu Ser Leu Leu
            100                 105                 110
Ala Ile Leu Tyr Asp Tyr Val Trp Pro Leu Pro Arg Tyr Leu Cys Pro
        115                 120                 125
Val Trp Ile Ser Leu Asp Val Leu Phe Ser Thr Ala Ser Ile Met His
    130                 135                 140
Leu Cys Ala Ile Ser Leu Asp Arg Tyr Val Ala Ile Arg Asn Pro Ile
145                 150                 155                 160
Glu His Ser Arg Phe Asn Ser Arg Thr Lys Ala Ile Met Lys Ile Ala
                165                 170                 175
Ile Val Trp Ala Ile Ser Ile Gly Val Ser Val Pro Ile Pro Val Ile
            180                 185                 190
Gly Leu Arg Asp Glu Glu Lys Val Phe Val Asn Asn Thr Thr Cys Val
        195                 200                 205
Leu Asn Asp Pro Asn Phe Val Leu Ile Gly Ser Phe Val Ala Phe Phe
    210                 215                 220
Ile Pro Leu Thr Ile Met Val Ile Thr Tyr Cys Leu Thr Ile Tyr Val
225                 230                 235                 240
Leu Arg Arg Gln Ala Leu Met Leu Leu His Gly His Thr Glu Glu Pro
                245                 250                 255
Pro Gly Leu Ser Leu Asp Phe Leu Lys Cys Cys Lys Arg Asn Thr Ala
            260                 265                 270
Glu Glu Glu Asn Ser Ala Asn Pro Asn Gln Asp Gln Asn Ala Arg Arg
        275                 280                 285
Arg Lys Lys Lys Glu Arg Arg Pro Arg Gly Thr Met Gln Ala Ile Asn
    290                 295                 300
Asn Glu Arg Lys Ala Ser Lys Val Leu Gly Ile Val Phe Phe Val Phe
305                 310                 315                 320
Leu Ile Met Trp Cys Pro Phe Phe Ile Thr Asn Ile Leu Ser Val Leu
                325                 330                 335
Cys Glu Lys Ser Cys Asn Gln Lys Leu Met Glu Lys Leu Leu Asn Val
            340                 345                 350
Phe Val Trp Ile Gly Tyr Val Cys Ser Gly Ile Asn Pro Leu Val Tyr
        355                 360                 365
Thr Leu Phe Asn Lys Ile Tyr Arg Arg Ala Phe Ser Asn Tyr Leu Arg
    370                 375                 380
Cys Asn Tyr Lys Val Glu Lys Lys Pro Pro Val Arg Gln Ile Pro Arg
385                 390                 395                 400
Val Ala Ala Thr Ala Leu Ser Gly Arg Glu Leu Asn Val Asn Ile Tyr
                405                 410                 415
Arg His Thr Asn Glu Pro Val Ile Glu Lys Ala Ser Asp Asn Glu Pro
            420                 425                 430
Gly Ile Glu Met Gln Val Glu Asn Leu Glu Leu Pro Val Asn Pro Ser
        435                 440                 445
Ser Val Val Ser Glu Arg Ile Ser Ser Val
    450                 455

<210> SEQ ID NO 12
<211> LENGTH: 9
<212> TYPE: PRT
<213> ORGANISM: Artificial Sequence
<220> FEATURE:
<223> OTHER INFORMATION: sequence encoding epitope for anti-HA
      monoclonal antibody

<400> SEQUENCE: 12
```

```
-continued

Tyr Pro Tyr Asp Val Pro Asp Tyr Ala
 1               5
```